United States Patent
Congreve et al.

(10) Patent No.: US 11,034,704 B2
(45) Date of Patent: *Jun. 15, 2021

(54) MUSCARINIC RECEPTOR AGONISTS

(71) Applicant: Heptares Therapeutics Limited, Cambridge (GB)

(72) Inventors: Miles Stuart Congreve, Cambridge (GB); Giles Albert Brown, Cambridge (GB); Benjamin Gerald Tehan, Cambridge (GB); Mark Pickworth, Cambridge (GB); Julie Elaine Cansfield, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/584,185

(22) Filed: Sep. 26, 2019

(65) Prior Publication Data

US 2020/0017530 A1     Jan. 16, 2020

Related U.S. Application Data

(63) Continuation of application No. 15/987,506, filed on May 23, 2018, now Pat. No. 10,428,088, which is a continuation of application No. 15/126,935, filed as application No. PCT/GB2015/050807 on Mar. 19, 2015, now Pat. No. 10,030,035.

(30) Foreign Application Priority Data

Mar. 19, 2014 (GB) ..................... 1404922

(51) Int. Cl.

| C07D 519/00 | (2006.01) |
| C07D 471/10 | (2006.01) |
| C07D 498/10 | (2006.01) |
| A61K 31/438 | (2006.01) |
| A61K 31/439 | (2006.01) |

(52) U.S. Cl.
CPC .......... *C07D 519/00* (2013.01); *A61K 31/438* (2013.01); *A61K 31/439* (2013.01); *C07D 471/10* (2013.01); *C07D 498/10* (2013.01)

(58) Field of Classification Search
CPC ... C07D 519/00; C07D 471/10; A61K 31/438
USPC ....................................................... 514/212
See application file for complete search history.

(56) References Cited

U.S. PATENT DOCUMENTS

| 9,669,013 B2 | 6/2017 | Brown et al. |
| 9,670,183 B2 | 6/2017 | Brown et al. |
| 9,907,805 B2 | 3/2018 | Congreve et al. |
| 10,030,035 B2 | 7/2018 | Congreve et al. |
| 10,196,380 B2 | 2/2019 | Brown et al. |
| 10,428,088 B2 | 10/2019 | Congreve et al. |
| 10,501,483 B2 * | 12/2019 | Dinh ............... C07D 519/00 |
| 2005/0176703 A1 | 8/2005 | Gabriel et al. |

FOREIGN PATENT DOCUMENTS

| CN | 101374519 A | 2/2009 |
| WO | 1999/32479 A1 | 7/1999 |
| WO | 1999/32489 A1 | 7/1999 |
| WO | 2006/058303 A2 | 6/2006 |
| WO | 2007/067504 A2 | 6/2007 |
| WO | 2007/076070 A2 | 7/2007 |
| WO | 2007/100670 A1 | 9/2007 |
| WO | 2008/021375 A2 | 2/2008 |
| WO | 2015/118342 A1 | 8/2015 |

OTHER PUBLICATIONS

Yang Cao et al Synthesis and Biological and Characterstzation of 1-methyl-1,2,5,6-tetrahydropyridy-1,2,5-thiadiazole Deriratives as Muscarinic agonists for treatment of Neurological Disorders (Year: 2003).*
Allan Levey, muscarine acetylcholine receptor expression in memory circuits: Implications for treatment of Alzheimer disease. (Year : 1996).*
U.S. Appl. No. 15/126,935, filed Sep. 16, 2016, U.S. Pat. No. 10,030,035, Issued.
U.S. Appl. No. 15/987,506, filed May 23, 2018, U.S. Pat. No. 10,428,088, Issued.
Levey, Muscarinic acetylcholine receptor expression in memory circuits: implications for treatment of Alzheimer disease. Proc Natl Acad Sci U S A. Nov. 26, 1996;93(24):13541-6.
Great Britain Search Report for Application No. 1404922.5 Search Report, dated Oct. 20, 2014.
International Preliminary Examination Report for Application No. PCT/GB2015/050807, dated Sep. 20, 2016.

* cited by examiner

*Primary Examiner* — Rita J Desai
(74) *Attorney, Agent, or Firm* — McCarter & English, LLP; Steven G. Davis; Mei Bai

(57) ABSTRACT

This invention relates to compounds that are agonists of the muscarinic $M_1$ receptor and which are useful in the treatment of muscarinic $M_1$ receptor mediated diseases. Also provided are pharmaceutical compositions containing the compounds and the therapeutic uses of the compounds. Compounds provided are of formula

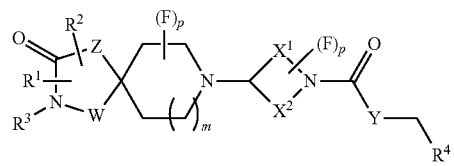

where m, p, q, W, Z, Y, $X^1$, $X^2$, $R^1$, $R^2$, $R^3$ and $R^4$ are as defined herein.

13 Claims, 1 Drawing Sheet

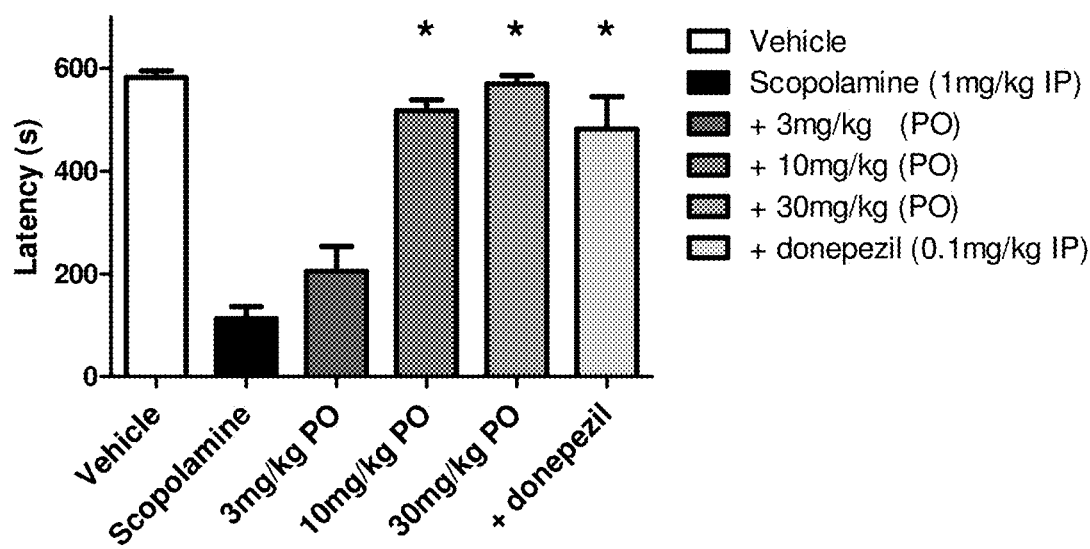
* P<0.05 versus vehicle/scopolamine
Mann-Whitney u-test

MUSCARINIC RECEPTOR AGONISTS

RELATED APPLICATION INFORMATION

This application is a continuation of U.S. application Ser. No. 15/987,506, filed May 23, 2018, which is a continuation of U.S. application Ser. No. 15/126,935, filed Sep. 16, 2016, now U.S. Pat. No. 10,030,035, which is a 371 U.S. national stage of International Application No.: PCT/GB2015/050807, filed Mar. 19, 2015, which claims priority from GB Application Serial No.: 1404922.5, filed Mar. 19, 2014. The entire contents of these applications are incorporated herein by reference in their entirety.

This invention relates to a class of novel bridged bicyclic compounds, their salts, pharmaceutical compositions containing them and their use in therapy of the human body. In particular, the invention is directed to a class of compounds, which are agonists of the muscarinic $M_1$ receptor and/or $M_4$ receptor, and hence are useful in the treatment of Alzheimer's Disease, schizophrenia, cognitive disorders and other diseases mediated by the muscarinic $M_1/M_4$ receptors, as well as the treatment or alleviation of pain.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 *Science*). In schizophrenia, which is also characterised by cognitive impairments, mAChR density is reduced in the pre-frontal cortex, hippocampus and caudate putamen of schizophrenic subjects (Dean et al., 2002 *Mol Psychiatry*). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting (www.drugs.com/pro/donepezil.html; www.drugs.com/pro/rivastigmine.html).

Further discovery efforts have targeted the identification of direct $M_1$ mAChR agonists to target increases in cognitive function. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, non-amyloidgenic and amyloidgenic. Cleavage of APP by γ-secretase is common to both pathways, but in the former APP is cleaved by an α-secretase to yield soluble APPα. The cleavage site is within the Aβ sequence, thereby precluding its formation. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 *Neuron*). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*). Muscarinic receptors have also been implicated in the neurobiology of addiction. The reinforcing effects of cocaine and other addictive substances are mediated by the mesolimbic dopamine system where behavioral and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al *Psychopharmacology* (2011) August; 216(3): 367-78). Furthermore xanomeline has been demonstrated to block the effects of cocaine in these models.

Muscarinic receptors are also involved in the control of movement and potentially represent novel treatments for movement disorders such as Parkinson's disease, ADHD, Huntingdon's disease, tourette's syndrome and other syndromes associated with dopaminergic dysfunction as an underlying pathogenetic factor driving disease.

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neurol). This compound was also assessed in a small Phase II study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic side effects, including nausea, gastrointestinal pain, diarrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage however management of post-surgical pain is required.

Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 Bioorg Med Chem Lett; Johnson et al., 2010 Bioorg Med Chem Lett; Budzik et al., 2010 ACS Med Chem Lett). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

BRIEF DESCRIPTION OF THE DRAWINGS

FIG. 1 shows the latencies observed in the passive avoidance test of Example B.

THE INVENTION

The present invention provides compounds having activity as muscarinic $M_1$ or $M_1$ and $M_4$ receptor agonists. More particularly, the invention provides compounds that exhibit selectivity for the $M_1$, receptor relative to the $M_2$ and $M_3$ receptor subtypes.

Accordingly, in a first embodiment (Embodiment 1.1), the invention provides a compound of the formula (1) or formula (1a):

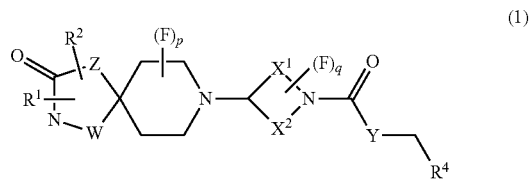

(1)

or a salt thereof, wherein:

p is 0, 1 or 2;

q is 0, 1 or 2;

W is C or N;

Z is $CH_2$, N, O or S;

Y is N, O, S or $CH_2$;

$X^1$ and $X^2$ are saturated hydrocarbon groups which together contain a total of five to nine carbon atoms and which link together such that the moiety:

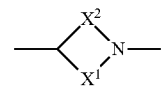

forms a bridged bicyclic ring system;

$R^1$ can be H, halo, CN, OH, $C_{1-3}$ alkoxy, $NH_2$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{3-6}$ cycloalkenyl, $CH_2$—$W^a$ where $W^a$ is an optionally substituted 5 or 6 membered cycloalkyl, heterocycloalkyl, aryl or heteroaryl ring, $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$; $SO_3R^5$;

$R^2$ can be independently H, halo, CN, OH, $C_{1-3}$alkoxy, $NH_2$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{3-6}$ cycloalkenyl, $CH_2$—$W^a$ where $W^a$ is an optionally substituted 5 or 6 membered cycloalkyl, heterocycloalkyl, aryl or heteroaryl ring, $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$; or $R^1$ and $R^2$ together form an optionally substituted cycloalkyl or heterocycloalkyl ring;

$R^4$ can be H, optionally substituted $C_{1-5}$ alkyl, optionally substituted $C_{1-5}$ alkenyl, optionally substituted $C_{1-5}$ alkynyl, optionally substituted $C_{2-6}$ cycloalkyl, optionally substituted $C_{2-6}$ cycloalkenyl;

$R^5$, $R^6$ and $R^7$ can be independently H, $C_{1-6}$ alkyl.
or formula (1a)

(1a)

or a salt thereof, wherein:
m is 1 or 2
p is 0, 1 or 2;
q is 0, 1 or 2;
W is C or N;
Z is $CH_2$, N, O or S;
Y is N, O, S or $CH_2$;
$X^1$ and $X^2$ are saturated hydrocarbon groups which together contain a total of five to nine carbon atoms and which link together such that the moiety:

forms a bridged bicyclic ring system;
$R^1$ can be H, halo, CN, OH, $C_{1-3}$ alkoxy, $NH_2$, an optionally substituted $C_{1-6}$ non-aromatic hydrocarbon group where one or more carbon atoms is optionally replaced with a heteroatom selected from O, N or S, $W^a$ or $CH_2$—$W^a$ where $W^a$ is an optionally substituted 5 or 6 membered cycloalkyl, heterocycloalkyl, aryl or heteroaryl ring, $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$; $SO_3R^5$;
$R^2$ can be independently H, halo, CN, OH, $C_{1-3}$ alkoxy, $NH_2$, an optionally substituted $C_{1-6}$ non-aromatic hydrocarbon group where one or more carbon atoms is optionally replaced with a heteroatom selected from O, N or S, $W^a$ or $CH_2$—$W^a$ where $W^a$ is an optionally substituted 5 or 6 membered cycloalkyl, heterocycloalkyl, aryl or heteroaryl ring, $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$; or $R^1$ and $R^2$ or $R^3$ and $R^2$ together form an optionally substituted cycloalkyl or heterocycloalkyl ring;
$R^3$ can be independently H, OH, an optionally substituted $C_{1-6}$ non-aromatic hydrocarbon group where one or more carbon atoms is optionally replaced with a heteroatom selected from O, N or S, $W^a$ or $CH_2$—$W^a$ where $W^a$ is an optionally substituted 5 or 6 membered cycloalkyl, heterocycloalkyl, aryl or heteroaryl ring; or $R^3$ and $R^2$ together form an optionally substituted cycloalkyl or heterocycloalkyl ring;
$R^4$ can be H, optionally substituted $C_{1-5}$ alkyl, optionally substituted $C_{1-5}$ alkenyl, optionally substituted $C_{1-5}$alkynyl, optionally substituted $C_{2-6}$ cycloalkyl, optionally substituted $C_{2-6}$ cycloalkenyl;
$R^5$, $R^6$ and $R^7$ can be independently H, $C_{1-6}$ alkyl.

Particular and preferred compounds of the formula (1) or formula (1a) are as defined in the following Embodiments 1.2 to 1.66:

1.2 A compound according to Embodiment 1.1 wherein $R^1$ is H or a $C_{1-6}$ non-aromatic hydrocarbon group containing 0, 1 or 2 carbon-carbon multiple bonds, wherein the hydrocarbon group is optionally substituted with one to six fluorine atoms and wherein one or two, but not all, carbon atoms of the hydrocarbon group may optionally be replaced by a heteroatom selected from O, N and S and oxidised forms thereof.

1.3 A compound according to either of Embodiments 1.1 and 1.2 wherein $R^1$ is selected from H; $C_{1-6}$ alkyl; $C_{2-6}$ alkenyl; $C_{2-6}$ alkynyl; and $C_{1-6}$ non-aromatic hydrocarbon groups consisting of or containing a $C_{3-6}$ cycloalkyl or $C_{5-6}$ cycloalkenyl group; each of the said alkyl, alkenyl, alkynyl and non-aromatic hydrocarbon groups being optionally substituted with one to six fluorine atoms and wherein one or two, but not all, carbon atoms of each of the alkyl, alkenyl, alkynyl and non-aromatic hydrocarbon groups may optionally be replaced by a heteroatom selected from O, N and S and oxidised forms thereof.

1.4 A compound according to Embodiment 1.1 wherein $R^1$ is a group $W^a$ or $CH_2$—$W^a$ where $W^a$ is an optionally substituted 5 or 6 membered cycloalkyl, heterocycloalkyl, aryl or heteroaryl ring, or $R^1$ and $R^2$ are joined together to form a ring, which may be fused or spirocyclic.

1.5 A compound according to Embodiment 1.1 wherein $R^1$ is $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$ where $R^5$, $R^6$ and $R^7$ can be independently H, $C_{1-6}$ alkyl.

1.6 A compound according to any one of Embodiments 1.1 to 1.5 wherein $R^1$ is selected from:
H;
Halogen;
Cyano;
OH;
$C_{1-3}$ alkoxy;
$NH_2$;
$C_{1-6}$ alkyl optionally substituted with 1 to 6 fluorine atoms;
$C_{3-6}$ alkyl optionally substituted with 1 heteroatom atom selected from O, N or S;
$C_{2-6}$ alkenyl;
$C_{2-6}$ alkynyl;
$C_{3-6}$ cycloalkyl;
$CH_2$—$C_{3-6}$ cycloalkyl;
$C_{5-6}$ cycloalkenyl;
$CH_2$-aryl;
$CH_2$-heteroaryl
aryl
heteroaryl
$NR^5R^6$, where $R^5$ and $R^6$ are independently H, $C_{1-6}$ alkyl;
$COOR^5$, where $R^5$ is H, $C_{1-6}$ alkyl;
$CONR^5R^6$ where $R^5$ and $R^6$ are independently H, $C_{1-6}$ alkyl;
$NR^7CONR^5R^6$, where $R^5$, $R^6$ and $R^7$ are independently H, $C_{1-6}$ alkyl;
$NR^7COOR^5$, where $R^5$ and $R^7$ are independently H, $C_{1-6}$ alkyl;
$OCONR^5R^6$, where $R^5$ and $R^6$ are independently H, $C_{1-6}$ alkyl;
$SR^5$, where $R^5$ is H, $C_{1-6}$ alkyl;
$SOR^5$, where $R^5$ is H, $C_{1-6}$ alkyl;
$SO_2R^5$, where $R^5$ is H, $C_{1-6}$ alkyl;
$SO_3R^5$, where $R^5$ is H, $C_{1-6}$ alkyl;
a spirocycle of formula $(CH_2)n$ where n is 2, 3, 4, 5 or 6.

1.7 A compound according to Embodiment 1.6 wherein $R^1$ is H or $C_{1-6}$ alkyl optionally substituted with 1 to 6 fluorine atoms.

1.8 A compound according to Embodiment 1.5 wherein $R^1$ is H or $C_{1-5}$ alkyl.

1.9 A compound according to any one of Embodiments 1.1 to 1.8 wherein $R^2$ is H or a $C_{1-6}$ non-aromatic hydrocarbon group containing 0, 1 or 2 carbon-carbon multiple bonds, wherein the hydrocarbon group is optionally substituted with one to six fluorine atoms and wherein one or two, but not all, carbon atoms of the hydrocarbon group may optionally be replaced by a heteroatom selected from O, N and S and oxidised forms thereof.

1.10 A compound according to any one of Embodiments 1.1 to 1.9 wherein $R^2$ is selected from H; $C_{1-6}$ alkyl; $C_{2-6}$ alkenyl; $C_{2-6}$ alkynyl; and $C_{1-6}$ non-aromatic hydrocarbon groups consisting of or containing a $C_{3-6}$cycloalkyl or $C_{5-6}$ cycloalkenyl group; each of the said alkyl, alkenyl, alkynyl and non-aromatic hydrocarbon groups being optionally substituted with one to six fluorine atoms and wherein one or two, but not all, carbon atoms of each of the alkyl, alkenyl, alkynyl and non-aromatic hydrocarbon groups may optionally be replaced by a heteroatom selected from O, N and S and oxidised forms thereof.

1.11 A compound according to any one of Embodiments 1.1 to 1.8 wherein $R^2$ is a group $CH_2$—$W^a$ where $W^a$ is an optionally substituted 5 or 6 membered cycloalkyl, heterocycloalkyl, aryl or heteroaryl ring, or $R^1$ and $R^2$ are joined together to form a ring, which may be fused or spirocyclic.

1.12 A compound according to any one of Embodiments 1.1 to 1.8 wherein $R^2$ is $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$ where $R^5$, $R^6$ and $R^7$ can be independently H, $C_{1-6}$ alkyl.

1.13 A compound according to any one of Embodiments 1.1 to 1.12 wherein $R^2$ is selected from:
H;
Halogen;
Cyano;
OH;
$C_{1-3}$ alkoxy;
$NH_2$;
$C_{1-6}$ alkyl optionally substituted with 1 to 6 fluorine atoms;
$C_{2-6}$ alkenyl;
$C_{2-6}$ alkynyl;
$C_{3-6}$ cycloalkyl;
$C_{5-6}$ cycloalkenyl;
$CH_2$-aryl
$CH_2$-heteroaryl
$NR^5R^6$, where $R^5$ and $R^6$ are independently H, $C_{1-6}$ alkyl;
$COOR^5$, where $R^5$ is H, $C_{1-6}$ alkyl;
$CONR^5R^6$ where $R^5$ and $R^6$ are independently H, $C_{1-6}$ alkyl;
$NR^7CONR^5R^6$, where $R^5$, $R^6$ and $R^7$ are independently H, $C_{1-6}$ alkyl;
$NR^7COOR^5$, where $R^5$ and $R^7$ are independently H, $C_{1-6}$ alkyl;
$OCONR^5R^6$, where $R^5$ and $R^6$ are independently H, $C_{1-6}$ alkyl;
$SR^5$, where $R^5$ is H, $C_{1-6}$ alkyl;
$SOR^5$, where $R^5$ is H, $C_{1-6}$ alkyl;
$SO_2R^5$, where $R^5$ is H, $C_{1-6}$ alkyl;
$SO_3R^5$, where $R^5$ is H, $C_{1-6}$ alkyl.

1.13 A compound according to Embodiment 1.12 wherein $R^2$ is H or $C_{1-6}$ alkyl optionally substituted with 1 to 6 fluorine atoms.

1.14 A compound according to Embodiment 1.13 wherein $R^2$ is H or $C_{1-6}$ alkyl.

1.15 A compound according to any one of Embodiments 1.1 to 1.14 wherein $R^1$ and $R^2$ are selected from hydrogen and $C_{1-6}$ alkyl.

1.16 A compound according to Embodiments 1.15 wherein $R^1$ and $R^2$ are independently H, methyl, ethyl, propyl, isopropyl or benzyl.

1.17 A compound according to Embodiment 1.1 wherein $R^1$ and $R^2$ together or the $R^3$ and $R^2$ together form an optionally substituted cycloalkyl or heterocycloalkyl ring. The ring can replace the $R^3$ group atom on the nitrogen. The ring may be fused or spirocyclic.

1.18 A compound according to Embodiment 1.17 wherein $R^1$ and $R^2$ together form a cycloalkyl ring optionally incorporating a maximum of 2 heteroatoms selected from O, S or N, and optionally substituted by a maximum of 6 atoms of F.

1.19 A compound according to Embodiment 1.1 wherein $R^3$ is H, OH or a $C_{1-6}$ non-aromatic hydrocarbon group containing 0, 1 or 2 carbon-carbon multiple bonds, wherein the hydrocarbon group is optionally substituted with one to six fluorine atoms and wherein one or two, but not all, carbon atoms of the hydrocarbon group may optionally be replaced by a heteroatom selected from O, N and S and oxidised forms thereof.

1.20 A compound according to either of Embodiment 1, 19 wherein $R^3$ is selected from H; OH, $C_{1-6}$ alkyl; $C_{2-5}$ alkenyl; $C_{2-6}$ alkynyl; and $C_{1-6}$ non-aromatic hydrocarbon groups consisting of or containing a $C_{3-6}$cycloalkyl or $C_{5-6}$ cycloalkenyl group; each of the said alkyl, alkenyl, alkynyl and non-aromatic hydrocarbon groups being optionally substituted with one to six fluorine atoms and wherein one or two, but not all, carbon atoms of each of the alkyl, alkenyl, alkynyl and non-aromatic hydrocarbon groups may optionally be replaced by a heteroatom selected from O, N and S and oxidised forms thereof.

1.21 A compound according to Embodiment 1.19 wherein $R^3$ is a group $W^a$ or $CH_2$—$W^a$ where $W^a$ is an optionally substituted 5 or 6 membered cycloalkyl, heterocycloalkyl, aryl or heteroaryl ring, or $R^1$ and $R_2$ are joined together to form a ring, which may be fused or spirocyclic.

1.22 A compound according to any one of Embodiments 1.19 to 1.21 wherein $R^3$ is selected from:
H;
OH
$C_{1-6}$ alkyl optionally substituted with 1 to 6 fluorine atoms;
$C_{3-6}$ alkyl optionally substituted with 1 heteroatom atom selected from O, N or S;
$C_{2-6}$ alkenyl;
$C_{2-6}$ alkynyl;
$C_{3-6}$ cycloalkyl;
$CH_2$—$C_{3-6}$ cycloalkyl;
$C_{5-6}$ cycloalkenyl;
$CH_2$-aryl
$CH_2$-heteroaryl
aryl
heteroaryl 1.23 A compound according to Embodiment 1.22 wherein $R^3$ is H or $C_{1-6}$ alkyl optionally substituted with 1 to 6 fluorine atoms.

1.24 A compound according to Embodiment 1.5 wherein $R^3$ is H or $C_{1-5}$ alkyl.

1.25 A compound according to any one of Embodiments 1.1 to 1.24 wherein Z is $CH_2$, N, O or S.

1.26 A compound according to Embodiment 1.25 wherein Z is $CH_2N$ or O.

1.27 A compound according to Embodiment 1.25 wherein Z is $CH_2$.

1.28 A compound according to Embodiment 1.25 wherein Z is N.

1.29 A compound according to Embodiment 1.25 wherein Z is O. When Z is O, $R^3$ can be specified as being H. Alternatively when Z is O, m can be specified as being 2. Alternatively when Z is O, either $R^3$ is H or m is 2.

1.30 A compound according to any one of Embodiments 1.1 to 1.29 wherein $R^4$ is H or an acyclic $C_{1-4}$ hydrocarbon group optionally substituted with one or more fluorine atoms.

1.31 A compound according to Embodiment 1.30 wherein $R^4$ is H or an acyclic $C_{1-3}$ hydrocarbon group optionally substituted with one or more fluorine atoms.

1.32 A compound according to Embodiment 1.31 wherein $R^4$ is H or a $C_{1-3}$ alkyl group or a $C_{1-2}$ alkynyl group.

1.33 A compound according to Embodiment 1.32 wherein $R^4$ is selected from H, methyl, fluoromethyl, ethyl, ethynyl and 1-propynyl.

1.34 A compound according to Embodiment 1.33 wherein $R^4$ is methyl.

1.35 A compound according to any one of Embodiments 1.1 to 1.34 wherein p is 0 or 1.

1.36 A compound according to Embodiment 1.35 wherein p is 0.

1.37 A compound according to Embodiment 1.35 wherein q is 0 or 1.

1.38 A compound according to any one of Embodiments 1.1 to 1.37 wherein m is 0.

1.39 A compound according to any one of Embodiments 1.1 to 1.37 wherein m is 1.

1.40 A compound according to any one of Embodiments 1.1 to 1.39 wherein Y is N, O, or $CH_2$.

1.41 A compound according to Embodiment 1.40 wherein Y is N.

1.42 A compound according to Embodiment 1.40 wherein Y is O.

1.43 A compound according to any one of Embodiments 1.1 to 1.40 wherein W is C.

1.44 A compound according to Embodiments 1.1 to 1.43 wherein the bridged bicyclic ring system is an azabicyclo-heptane, azabicyclo-octane or azabicyclo-nonane ring system.

1.45 A compound according to Embodiment 1.44 wherein the bridged bicyclic ring system is selected from ring systems BA to BH below which may be substituted with 0-2 optional fluorine atoms:

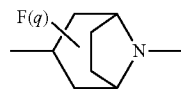
BA

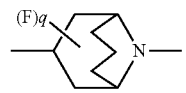
BB

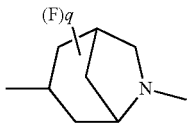
BC

BD

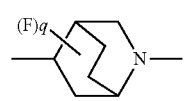
BE

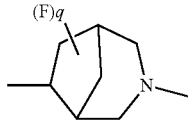
BF

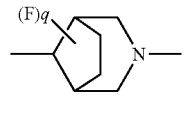
BG

BH 1.46 A compound according to Embodiment 1.45 wherein q is 0 or 1.

1.47 A compound according to any one of Embodiments 1.1 to 1.46 wherein $R^5$ is H or $C_{1-6}$ alkyl.

1.48 A compound according to Embodiment 1.47 wherein $R^5$ is H.

1.49 A compound according to Embodiment 1.47 wherein $R^5$ is $C_{1-3}$ alkyl.

1.50 A compound according to any one of Embodiments 1.1 to 1.49 wherein $R^6$ is H or $C_{1-5}$ alkyl.

1.51 A compound according to Embodiment 1.50 wherein $R^6$ is H.

1.52 A compound according to Embodiment 1.50 wherein $R^6$ is $C_{1-3}$ alkyl.

1.53 A compound according to any one of Embodiments 1.1 to 1.52 wherein $R^7$ is H or $C_{1-5}$ alkyl.

1.54 A compound according to Embodiment 1.53 wherein $R^7$ is H.

1.55 A compound according to Embodiment 1.53 wherein $R^7$ is $C_{1-3}$ alkyl.

1.56 A compound according to Embodiment 1.1 having the formula (2) or formula (2a):

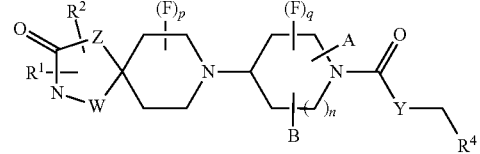
(2)

wherein n is 1 or 2;

A and B are linked together to form a carbon bridge of 1-3 atoms where n is 1, or 1-2 carbon atoms where n is 2 and p, q, W, Z, Y, $R^1$, $R^2$ and $R^4$ are as defined in any one of Embodiments 1.1 to 1.43; or

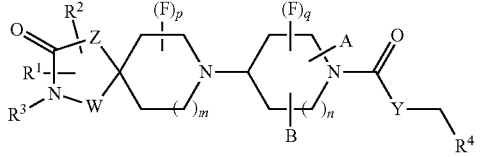
(2a)

wherein n is 1 or 2;

A and B are linked together to form a carbon bridge of 1-3 atoms where n is 1, or 1-2 carbon atoms where n is 2 and m, p, q, W, Z, Y, $R^1$, $R^2$, $R^3$ and $R^4$ are as defined in any one of Embodiments 1.1 to 1.43.

1.57 A compound according to Embodiment 1.1 having the formula (3) or formula (3a):

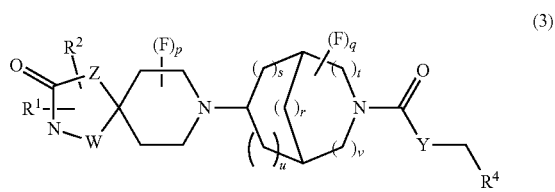

(3)

wherein r is 1, 2 or 3 and each of s, t u and v is 0 or 1, provided that the total of r, s, t, u and v is 3, 4 or 5, and p, q, W, Z, Y, $R^1$, $R^2$ and $R^4$ are as defined in any one of Embodiments 1.1 to 1.43; or

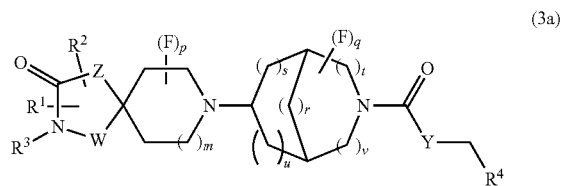

(3a)

wherein r is 1, 2 or 3 and each of s, t u and v is 0 or 1, provided that the total of r, s, t, u and v is 3, 4 or 5, and m, p, q, W, Z, Y, $R^1$, $R^2$, $R^3$ and $R^4$ are as defined in any one of Embodiments 1.1 to 1.43.

1.58 A compound according to Embodiment 1.1 having the formula (4) or formula (4a):

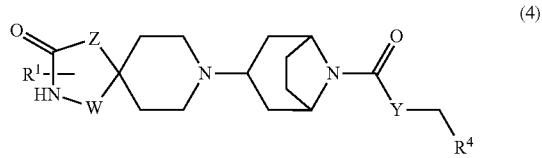

(4)

wherein $R^1$, W, Z, Y and $R^4$ are as defined in any one of Embodiments 1.1 to 1.43; or

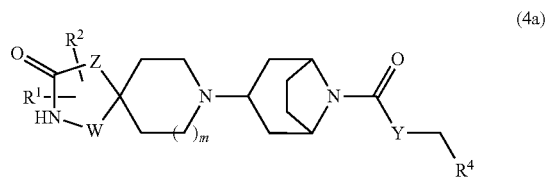

(4a)

wherein m, $R^1$, $R^2$, W, Z, Y and $R^4$ are as defined in any one of Embodiments 1.1 to 1.43.

1.59 A compound according to any one of Embodiments 1.56 to 1.58 wherein Z is $CH_2N$ or O.

1.60 A compound according to any one of Embodiments 1.56 to 1.59 wherein $R^4$ is selected from H, methyl, ethyl, ethynyl and 1-propynyl.

1.61 A compound according to Embodiment 1.60 wherein $R^4$ is selected from H or methyl.

1.62 A compound according to Embodiment 1.1 which is as defined in any one of Examples 1-1 to 9-2.

1.63 A compound according to any one of Embodiments 1.1 to 1.61 having a molecular weight of less than 550, for example less than 500, or less than 450.

1.64 A compound according to any one of Embodiments 1.1 to 1.63 which is in the form of a salt.

1.65 A compound according to Embodiment 1.64 wherein the salt is an acid addition salt.

1.66 A compound according to Embodiment 1.64 or Embodiment 1.65 wherein the salt is a pharmaceutically acceptable salt.

Definitions

In this application, the following definitions apply, unless indicated otherwise.

The term "treatment", in relation to the uses of the compounds of the formula (1) or formula (1a), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" (as in "$C_{1-5}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl $CH_2$-cycloalkyl and so on.

The terms "alkyl", "alkenyl", "alkynyl", "cycloalkyl" and "cycloalkenyl" are used in their conventional sense (e.g. as defined in the IUPAC Gold Book) unless indicated otherwise.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^2$, $R^3$ and $R^4$ above, where stated, one or two but not all, carbon atoms of the non-aromatic hydrocarbon group may optionally be replaced by a heteroatom selected from O, N and S and oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—S(O)$_2$—$CH_2$—, replacement of a carbon atom in a —$CH_2$—$CH_2$—$CH_2$-chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1) or formula (1a) can exist in the form of salts, for example acid addition salts or, in certain cases salts of organic and inorganic bases such as carboxylate, sulfonate and phosphate salts. All such salts are within the scope of this invention, and references to compounds of the formula (1) or formula (1a) include the salt forms of the compounds as defined in Embodiments 1.64 to 1.66.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.65) may be formed with a wide variety of acids, both inorganic and organic. Examples of acid addition salts falling within Embodiment 1.65 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) or formula (1a) contain an amine function, these may form quaternary ammonium salts, for example by reaction with an alkylating agent according to methods well known to the skilled person. Such quaternary ammonium compounds are within the scope of formula (1) or formula (1a).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.67), the invention provides a geometric isomer of a compound according to any one of Embodiments 1.1 to 1.66.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.68) the invention provides a compound according to any one of Embodiments 1.1 to 1.67 which contains a chiral centre.

The optical isomers may be characterised and identified by their optical activity (i.e. as + and − isomers, or d and/isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.69), the invention provides compositions containing a compound according to Embodiment 1.68 having one or more chiral centres, wherein at least 55% (e.g. at least 60%, 65%, 70%, 75%, 80%, 85%, 90% or 95%) of the compound of Embodiment 1.65 is present as a single optical isomer (e.g. enantiomer or diastereoisomer).

In one general embodiment (Embodiment 1.70), 99% or more (e.g. substantially all) of the total amount of the compound (or compound for use) of Embodiment 1.68 is present as a single optical isomer.

For example, in one embodiment (Embodiment 1.71) the compound is present as a single enantiomer.

In another embodiment (Embodiment 1.72), the compound is present as a single diastereoisomer.

The invention also provides mixtures of optical isomers, which may be racemic or non-racemic. Thus, the invention provides:

1.73 A compound according to Embodiment 1.68 which is in the form of a racemic mixture of optical isomers.

1.74 A compound according to Embodiment 1.68 which is in the form of a non-racemic mixture of optical isomers.

Isotopes

The compounds of the invention as defined in any one of Embodiments 1.1 to 1.74 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.75), the compound of any one of Embodiments 1.1 to 1.74 contains no radioactive isotopes. Such compounds are preferred for therapeutic use.

In another embodiment (Embodiment 1.76), however, the compound of any one of Embodiments 1.1 to 1.74 may contain one or more radioisotopes. Compounds containing such radioisotopes may be useful in a diagnostic context.

Solvates

Compounds of the formula (1) or formula (1a) as defined in any one of Embodiments 1.1 to 1.76 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.77 and 1.78, the invention provides:

1.77 A compound according to any one of Embodiments 1.1 to 1.76 in the form of a solvate.

1.78 A compound according to Embodiment 1.77 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.79), the invention provides a compound as defined in any one of Embodiments 1.1 to 1.76 in an anhydrous form (e.g. anhydrous crystalline form).

Crystalline and Amorphous Forms

The compounds of any one of Embodiments 1.1 to 1.79 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.80 A compound according to any one of Embodiments 1.1 to 1.79 in a crystalline form.

1.781 A compound according to any one of Embodiments 1.1 to 1.79 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.82 A compound according to any one of Embodiments 1.1 to 1.79 which is in an amorphous form.

Prodrugs

The compounds of the formula (1) or formula (1a) as defined in any one of Embodiments 1.1 to 1.76 may be presented in the form of a pro-drug. By "prodrugs" is meant for example any compound that is converted in vivo into a biologically active compound of the formula (1) or formula (1a), as defined in any one of Embodiments 1.1 to 1.76.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.83), the invention provides a pro-drug of a compound as defined in any one of Embodiments 1.1 to 1.76 wherein the compound contains a functional group which is convertible under physiological conditions to form a hydroxyl group or amino group.

Complexes and Clathrates

Also encompassed by formula (1) or formula (1a) in Embodiments 1.1 to 1.83 are complexes (e.g. inclusion complexes or clathrates with compounds such as cyclodextrins, or complexes with metals) of the compounds of Embodiments 1.1 to 1.83.

Accordingly, in another embodiment (Embodiment 1.84), the invention provides a compound according to any one of Embodiments 1.1 to 1.83 in the form of a complex or clathrate.

Biological Activity and Therapeutic Uses

The compounds of the present invention have activity as muscarinic $M_1$ receptor agonists. The muscarinic activity of the compounds can be determined using the Phospho-ERK1/2 assay described in Example A below.

A significant advantage of compounds of the invention is that they are highly selective for the $M_1$ receptor relative to the $M_2$ and $M_3$ receptor subtypes. Compounds of the invention are neither agonists nor antagonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 95) against the $M_1$ receptor in the functional assay described in Example A, they may have $pEC_{50}$ values of less than 5 and $E_{max}$ values of less than 20% when tested against the $M_2$ and $M_3$ subtypes in the functional assay of Example A.

Some compounds of the invention have activity at both the $M_1$ and $M_4$ receptors.

Accordingly, in Embodiments 2.1 to 2.9, the invention provides:

2.1 A compound according to any one of Embodiments 1.1 to 1.84 for use in medicine.

2.2 A compound according to any one of Embodiments 1.1 to 1.84 for use as a muscarinic $M_1$ or $M_1$ and $M_4$ receptor agonist.

2.3 A compound according to any one of Embodiments 1.1 to 1.84 which is a muscarinic $M_1$ receptor agonist having a $pEC_{50}$ greater than 6.9 and an $E_{max}$ of at least 80 against the $M_1$ receptor in the assay of Example A herein or an assay substantially similar thereto.

2.4 A compound according to Embodiment 2.3 which is a muscarinic $M_1$ receptor agonist having a $pEC_{50}$ greater than 7.0.

2.5 A compound according to Embodiment 2.3 or Embodiment 2.4 having an $E_{max}$ of at least 90 against the $M_1$ receptor.

2.6 A compound according to any one of Embodiments 1.1 to 1.84 which is a muscarinic $M_1$ and $M_4$ receptor agonist having a $pEC_{50}$ in the range from 6.0 to 8.7 and an $E_{max}$ of at least 60 against the $M_4$ receptor in the assay of Example A herein or an assay substantially similar thereto.

2.7 A compound according to any one of Embodiments 1.1 to 1.84 which is a muscarinic $M_1$ and $M_4$ receptor agonist having a $pEC_{50}$ in the range from 6.0 to 8.1 and an $E_{max}$ of at least 90 against the $M_4$ receptor in the assay of Example A herein or an assay substantially similar thereto.

2.8 A compound according to Embodiment 2.6 which is a muscarinic $M_4$ receptor agonist having a $pEC_{50}$ in the range from 7.5 to 8.7.

2.9 A compound according to Embodiment 2.7 which is a muscarinic $M_4$ receptor agonist having a $pEC_{50}$ in the range from 6.5 to 7.5.

2.10 A compound according to Embodiment 2.6 or Embodiment 2.8 having an $E_{max}$ of at least 75 against the $M_4$ receptor.

2.11 A compound according to Embodiment 2.7 or Embodiment 2.9 having an $E_{max}$ of at least 95 against the $M_4$ receptor.

2.12 A compound according to any one of Embodiments 2.3 to 2.11 which is selective for the $M_1$ and $M_4$ receptor compared to the muscarinic $M_2$ and $M_3$ receptors.

2.13 A compound according to Embodiment 2.12 which is selective for the $M_1$ receptor compared to the muscarinic $M_2$ and $M_3$ receptors.

2.14 A compound according to any one of Embodiments 2.3 to 2.5 which is selective for the $M_1$ receptor compared to the muscarinic $M_2$, $M_3$ and $M_4$ receptors.

2.15 A compound according to any one of Embodiments 2.3 to 2.14 which has a $pEC_{50}$ of less than 5 and an $E_{max}$ of less than 50 against the muscarinic $M_2$ and $M_3$ receptor subtypes.

2.16 A compound according to Embodiment 2.15 which has a $pEC_{50}$ of less than 4.5 and/or an $E_{max}$ of less than 30 against the muscarinic $M_2$ and $M_3$ receptor subtypes.

2.17 A compound according to any one of Embodiments 1.1 to 1.84 and Embodiments 2.3 to 2.16 for use in the treatment of a disease or condition mediated by the muscarinic $M_1$ receptor.

By virtue of their muscarinic $M_1$ or $M_1$ and $M_4$ receptor agonist activity, compounds of the invention can be used in the treatment of Alzheimer's disease, schizophrenia and other psychotic disorders, cognitive disorders and other diseases mediated by the muscarinic $M_1$ or $M_1$ and $M_4$ receptor, and can also be used in the treatment of various types of pain.

Accordingly, in Embodiments 2.16 to 2.39, the invention provides:

2.18 A compound according to any one of Embodiments 1.1 to 1.84 for use in the treatment of a cognitive disorder or psychotic disorder.

2.19 A compound for use in according to Embodiment 2.18 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as multi-infarct dementia, alcoholic dementia, hypothyroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and schizo-affective disorder.

2.20 A compound according to any one of Embodiments 1.1 to 1.84 for use in the treatment of Alzheimer's disease.

2.21 A compound according to any one of Embodiments 1.1 to 1.84 for use in the treatment of Schizophrenia.

2.22 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.84.

2.23 A method according to Embodiment 2.22 wherein the cognitive disorder comprises, arises from or is associated with a condition as defined in Embodiment 2.17.

2.24 A method according to Embodiment 2.23 wherein the cognitive disorder arises from or is associated with Alzheimer's disease.

2.25 A method according to Embodiment 2.23 wherein the cognitive disorder is Schizophrenia.

2.26 The use of a compound according to any one of Embodiments 1.1 to 1.84 for the manufacture of a medicament for the treatment of a cognitive disorder.

2.27 The use according to Embodiment 2.26 wherein the cognitive disorder comprises, arises from or is associated with a condition as defined in Embodiment 2.19.

2.28 The use according to Embodiment 2.27 wherein the cognitive disorder arises from or is associated with Alzheimer's disease.

2.29 The use according to Embodiment 2.28 wherein the cognitive disorder is Schizophrenia.

2.30 A compound according to any one of Embodiments 1.1 to 1.84 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.31 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.84.

2.32 A compound according to any one of Embodiments 1.1 to 1.84 for the treatment of peripheral disorders such as reduction of intra ocular pressure in Glaucoma and treatment of dry eyes and dry mouth including Sjogren's Syndrome.

2.33 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.84.

2.34 The use of a compound according to any one of Embodiments 1.1 to 1.84 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.35 The use of a compound according to any one of Embodiments 1.1 to 1.84 for the use in the treatment of skin lesions for example due to pemphigus vulgaris, dermatitis herpetiformis, pemphigoid and other blistering skin conditions.

2.36 The use of a compound according to any one of Embodiments 1.1 to 1.84 for the use in treating, preventing, ameliorating or reversing conditions associated with altered gastro-intestinal function and motility such as functional dyspepsia, irritable bowel syndrome, gastroesophageal acid reflux (GER) and esophageal dysmotility, symptoms of gastroparesis and chronic diarrhea.

2.37 The use of a compound according to any one of Embodiments 1.1 to 1.84 for the use in the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

2.38 The use of a compound according to any one of Embodiments 1.1 to 1.84 for the treatment of addiction.

2.39 The use of a compound according to any one of Embodiments 1.1 to 1.84 for the treatment of movement disorders such as Parkinson's disease, ADHD, Huntingdon's disease, tourette's syndrome and other syndromes associated with dopaminergic dysfunction as an underlying pathogenetic factor driving disease.

Methods for the Preparation of Compounds of the Formula (1) or Formula (1a)

Compounds of the formula (1) or formula (1a) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.84, which process comprises:

(A) the reaction of a compound of the formula (10)

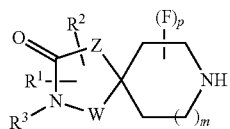
(10)

with a compound of the formula (11):

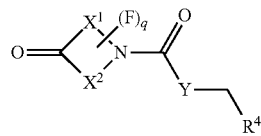
(11)

under reductive amination conditions; wherein $R^1$, $R^2$, $R^3$, $R^4$, $X^1$, $X^2$, W, Y, Z, m, p and q are as defined in any one of Embodiments 1.1 to 1.84; or (B) the reaction of a compound of the formula (12):

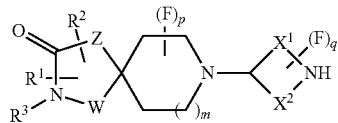
(12)

with a compound of the formula $Cl\text{—}C(\!=\!O)\text{—}CH_2\text{—}R^4$, in the presence of a base; or (C) the reaction of a compound of the formula (10)

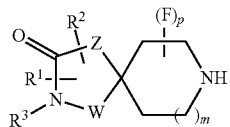
(10)

with a compound of the formula (13):

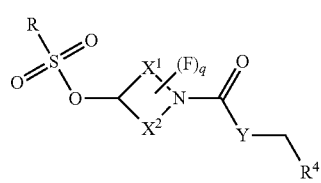
(13)

under nucleophilic substitution conditions; wherein $R^1$, $R^2$, $R^3$, $R^4$, $X^1$, $X^2$, W, Y, Z, m, p and q are as defined in any one of Embodiments 1.1 to 1.84; and optionally:

(D) converting one compound of the formula (1) or formula (1a) to another compound of the formula (1) or formula (1a).

In process variant (A), the piperidine heterocycle (10) is reacted with the substituted ketone (11) under reductive amination conditions. The reductive amination reaction is typically carried out at ambient temperature using a borohydride reducing agent such as sodium triacetoxy-borohydride in a solvent such as dichloromethane or dichloroethane containing acetic acid.

In process variant (C), the piperidine heterocycle (10) is reacted with the sulfonic ester (13, R=methyl or 4-methylbenzyl) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide Intermediate compounds of the formula (12) can be prepared by the series of reactions shown in Scheme 1 below.

Scheme 1

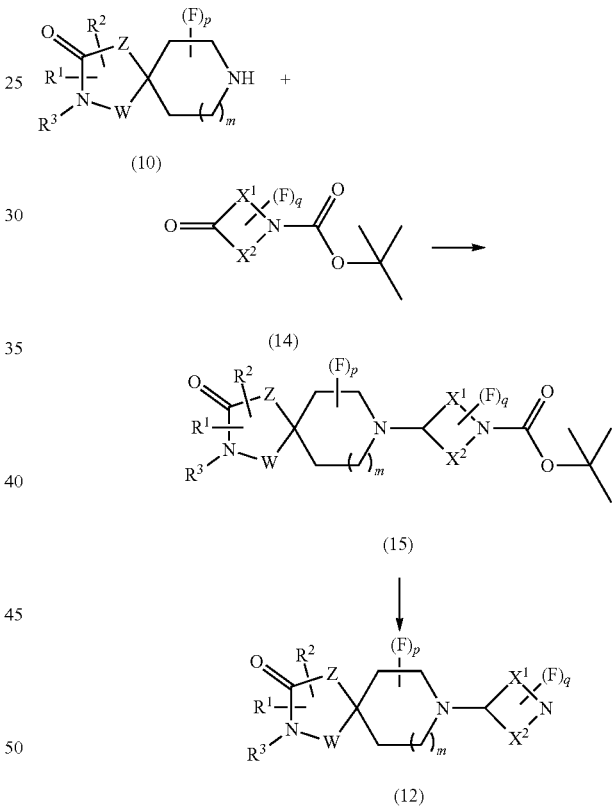

In reaction Scheme 1, the piperidine heterocycle (10) is reacted with the Boc-protected ketone (14) under reductive amination conditions. The reductive amination reaction is typically carried out with mild heating (e.g. to a temperature of from about 40° C. to about 70° C.) in the presence of either sodium cyanoborohydride in combination with zinc chloride or sodium triacetoxyborohydride in combination with titanium isopropoxide in a solvent such as dichloromethane or dichloroethane containing acetic acid to give an intermediate piperidine compound (15) which is then deprotected by removal of the Boc group by treatment with acid (e.g. trifluoroacetic acid in dichloromethane) to give the compound (12).

Compounds of the formula (12) can also be prepared by the sequence of reactions shown in Scheme 2 below.

Scheme 2

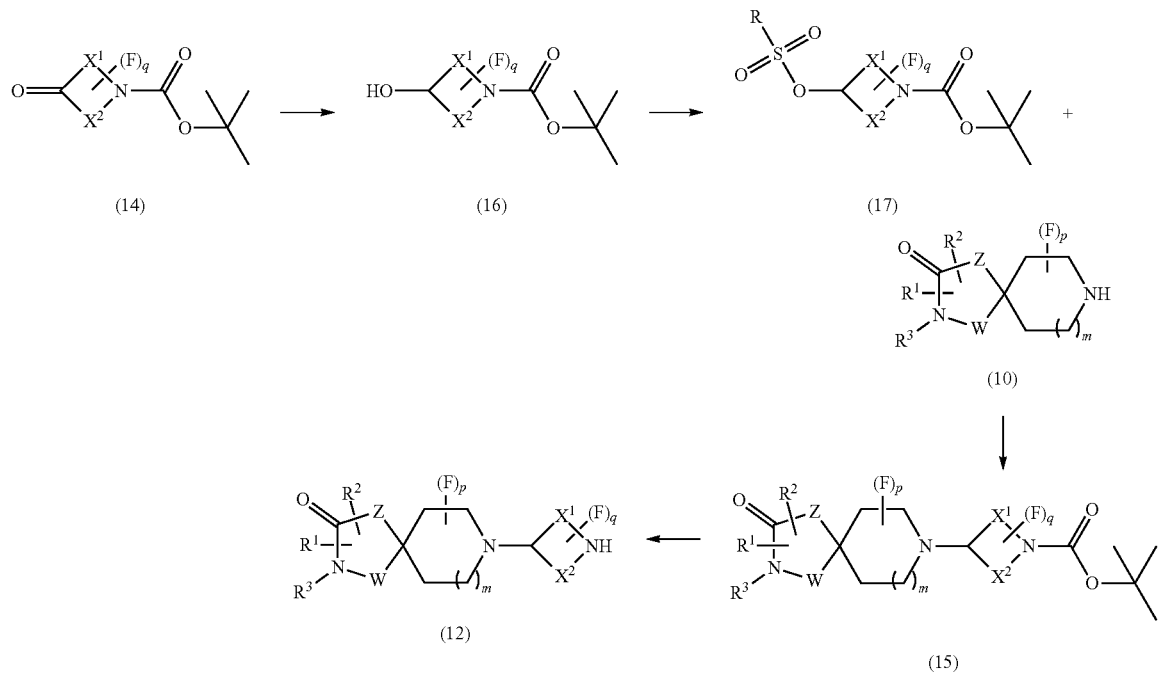

In Scheme 2, the Boc-protected ketone (14) is reduced to the alcohol (16) using sodium borohydride in methanol. The alcohol (16) is then activated as the sulfonic ester (17, R=methyl or 4-methylbenzyl) using the corresponding sulfonyl chloride in dichloromethane in the presence of a tertiary amine such as triethylamine or N,N-diisopropylethylamine. The sulfonic ester (17) is reacted with the piperidine heterocycle (10) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide to give compound (15), which is then deprotected by removal of the Boc group by treatment with acid (e.g. trifluoroacetic acid in dichloromethane) to give the compound (12).

Once formed, one compound of the formula (1) or formula (1a), or a protected derivative thereof, can be converted into another compound of the formula (1) or formula (1a) by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) or formula (1a) as defined in any one of Embodiments 1.1 to 1.84 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) or formula (1a) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) or formula (1a) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 9-2

The compounds of Examples 1-1 to 9-2 shown in Table 1 below have been prepared. Their NMR and LCMS properties and the methods used to prepare them are set out in Table 3. The starting materials for each of the Examples are listed in Table 2.

TABLE 1

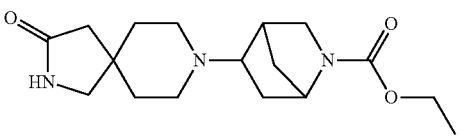 [SMILES: CCOC(=O)N1CC2CC1CC2N1CCC2(CC1)CNC(=O)C2]

Example 1-1

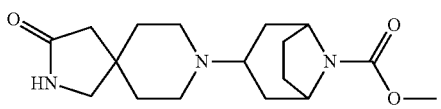 [SMILES: COC(=O)N1C2CCC1CC(N1CCC3(CC1)CNC(=O)C3)C2]

Example 2-1

TABLE 1-continued
| | |
|---|---|
| 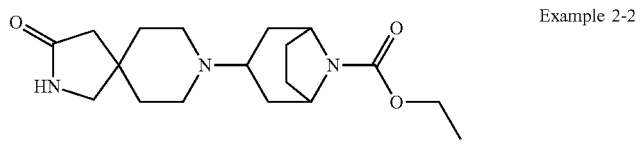 | Example 2-2 |
| 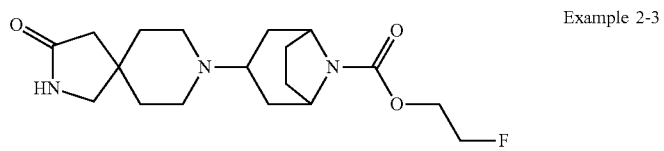 | Example 2-3 |
| 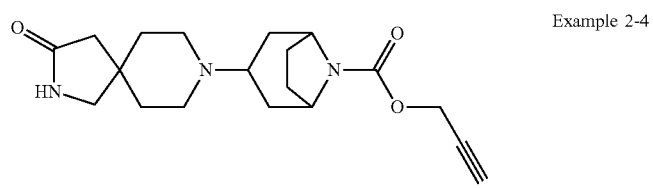 | Example 2-4 |
| 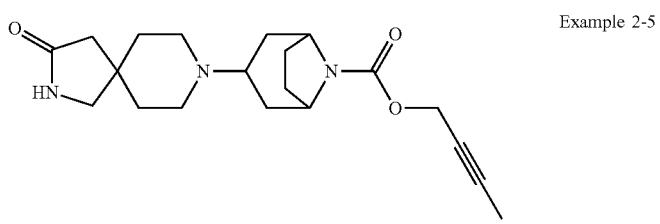 | Example 2-5 |
| 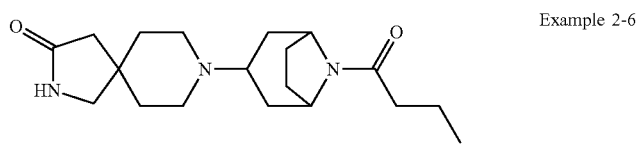 | Example 2-6 |
| 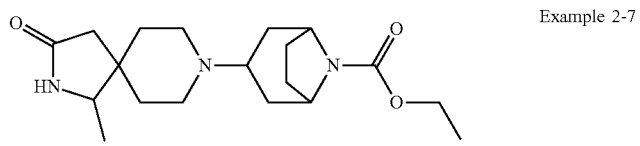 | Example 2-7 |
| 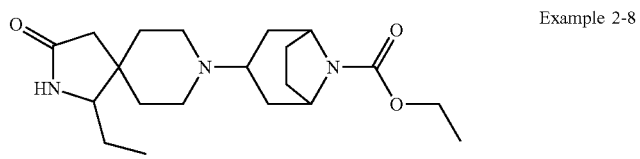 | Example 2-8 |
| 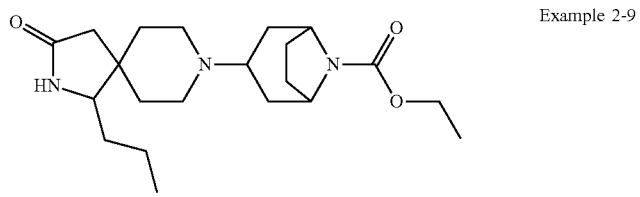 | Example 2-9 |

TABLE 1-continued
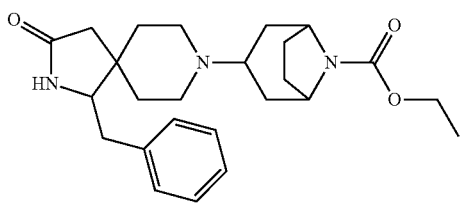 [SMILES: CCOC(=O)N1C2CCC1CC(N1CCC3(CC1)CC(=O)NC3Cc1ccccc1)C2] Example 2-10
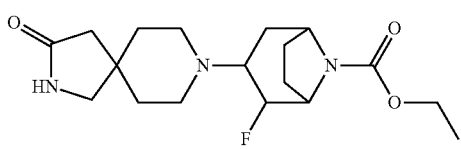 [SMILES: CCOC(=O)N1C2CCC1C(F)C(N1CCC3(CC1)CNC(=O)C3)C2] Example 2-11
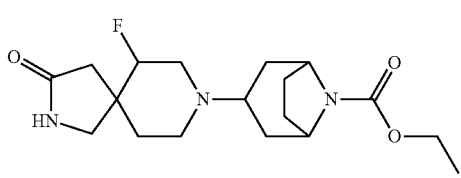 [SMILES: CCOC(=O)N1C2CCC1CC(N1CCC3(CNC(=O)C3)C(F)C1)C2] Example 2-12
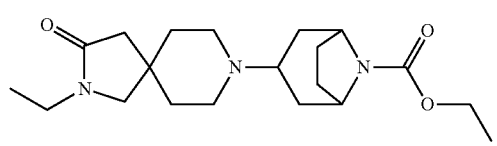 [SMILES: CCOC(=O)N1C2CCC1CC(N1CCC3(CC1)CC(=O)N(CC)C3)C2] Example 2-13
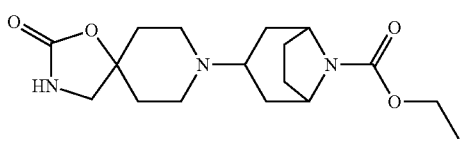 Example 2-14
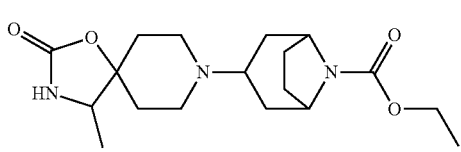 [SMILES: CCOC(=O)N1C2CCC1CC(N1CCC3(CC1)OC(=O)NC3C)C2] Example 2-15
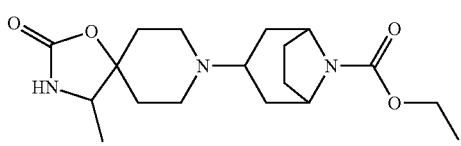 [SMILES: CCOC(=O)N1C2CCC1CC(N1CCC3(CC1)OC(=O)NC3C)C2] Example 2-15
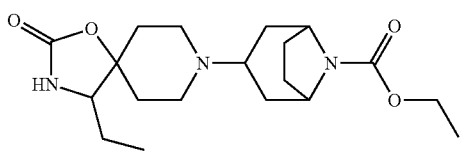 [SMILES: CCOC(=O)N1C2CCC1CC(N1CCC3(CC1)OC(=O)NC3CC)C2] Example 2-16
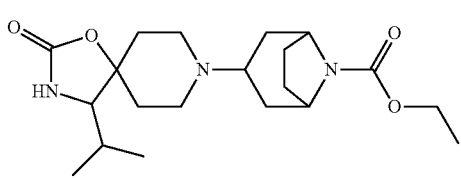 [SMILES: CCOC(=O)N1C2CCC1CC(N1CCC3(CC1)OC(=O)NC3C(C)C)C2] Example 2-17

TABLE 1-continued
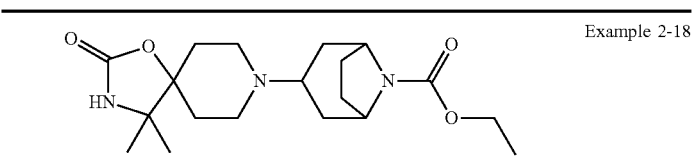 Example 2-18
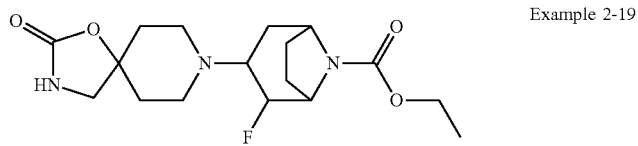 Example 2-19
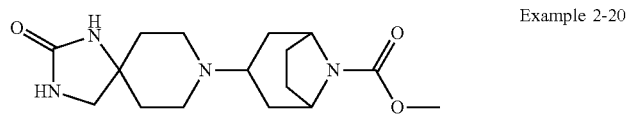 Example 2-20
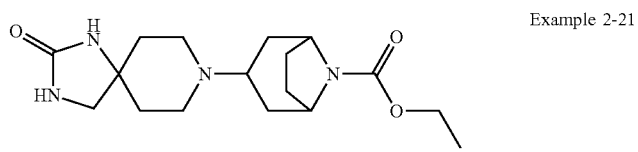 Example 2-21
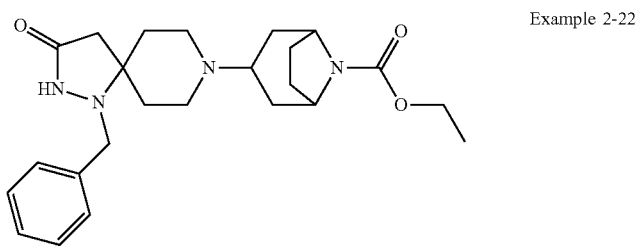 Example 2-22
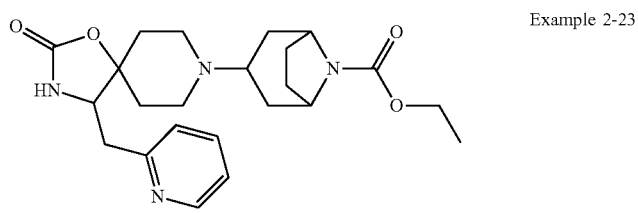 Example 2-23
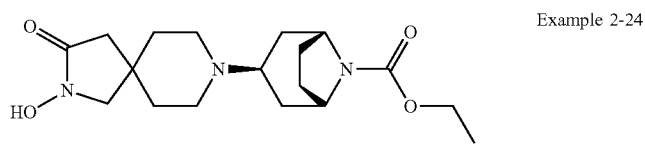 Example 2-24
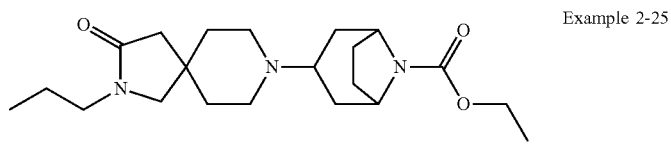 Example 2-25
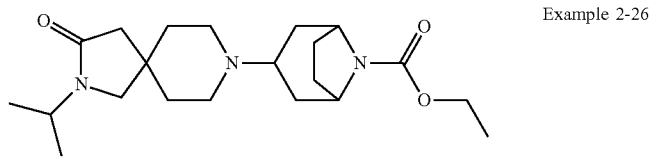 Example 2-26

TABLE 1-continued
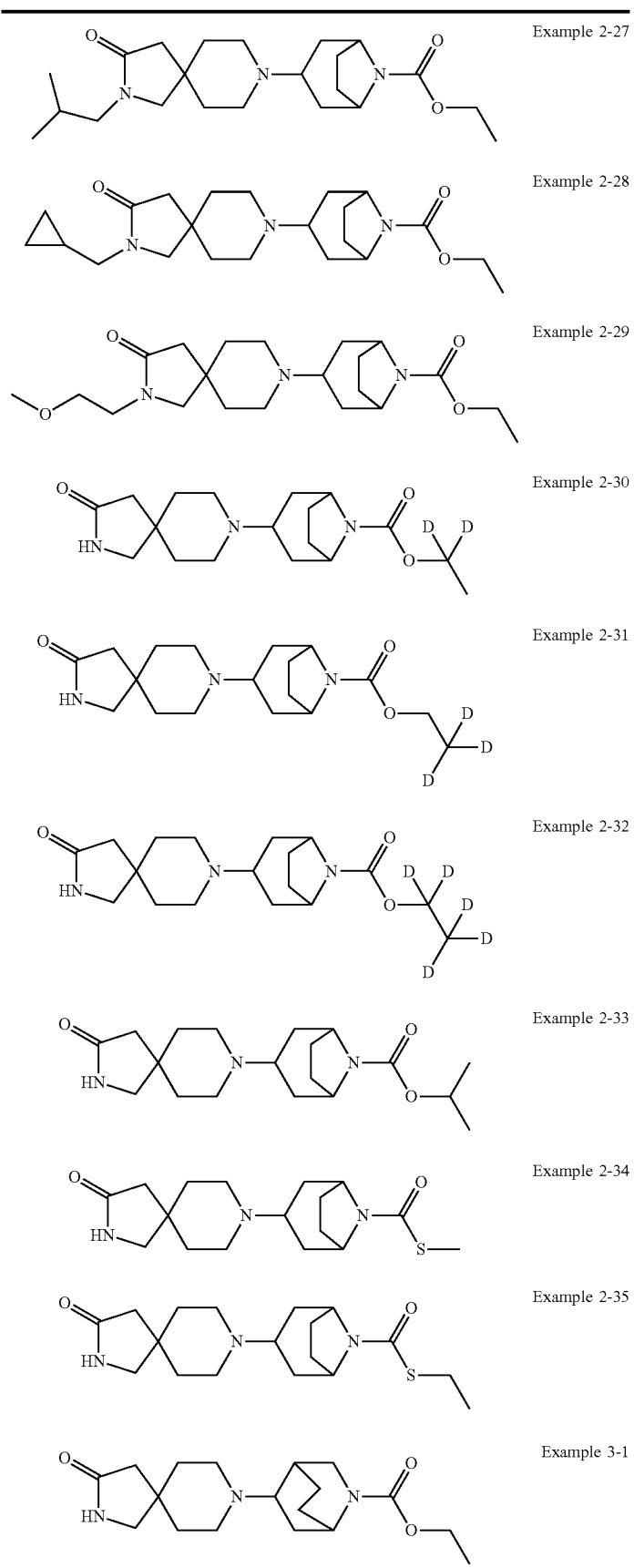
Example 2-27
Example 2-28
Example 2-29
Example 2-30
Example 2-31
Example 2-32
Example 2-33
Example 2-34
Example 2-35
Example 3-1

TABLE 1-continued
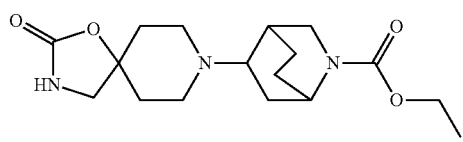 [SMILES: CCOC(=O)N1CC2CCC1CC2N1CCC2(CC1)CNC(=O)O2] Example 3-2
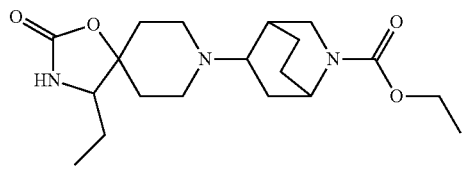 [SMILES: CCOC(=O)N1CC2CCC1CC2N1CCC2(CC1)OC(=O)NC2CC] Example 3-3
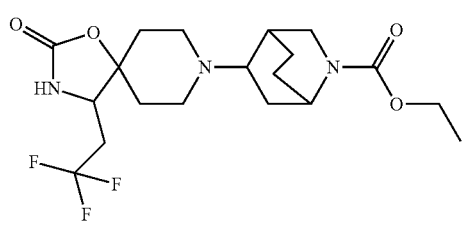 [SMILES: CCOC(=O)N1CC2CCC1CC2N1CCC2(CC1)OC(=O)NC2CC(F)(F)F] Example 3-4
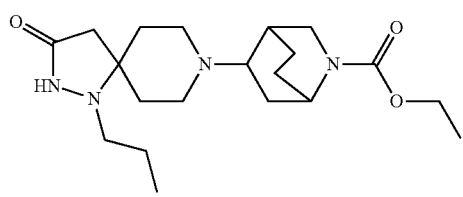 [SMILES: CCCN1NC(=O)CC12CCN(C1CC3CCC1CN3C(=O)OCC)CC2] Example 3-5
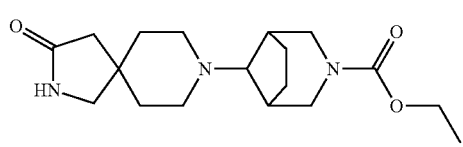 [SMILES: CCOC(=O)N1CC2CCC(C1)C2N1CCC2(CC1)CNC(=O)C2] Example 4-1
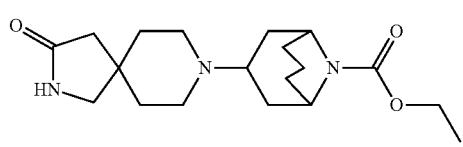 [SMILES: CCOC(=O)N1C2CCCC1CC(N1CCC3(CC1)CNC(=O)C3)C2] Example 5-1
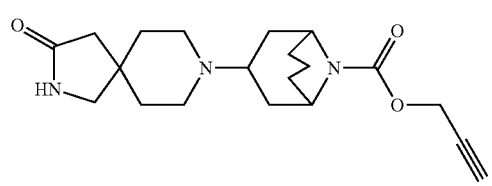 [SMILES: C#CCOC(=O)N1C2CCCC1CC(N1CCC3(CC1)CNC(=O)C3)C2] Example 5-2
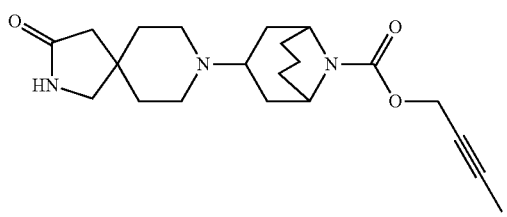 [SMILES: CC#CCOC(=O)N1C2CCCC1CC(N1CCC3(CC1)CNC(=O)C3)C2] Example 5-3

TABLE 1-continued
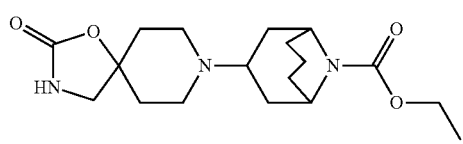 [SMILES: CCOC(=O)N1C2CCCC1CC(N1CCC3(CC1)CNC(=O)O3)C2] Example 5-4
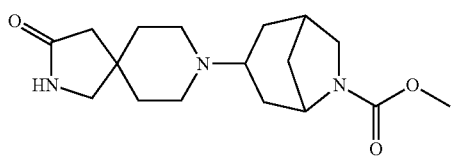 [SMILES: COC(=O)N1CC2CC(N3CCC4(CC3)CNC(=O)C4)CC1C2] Example 6-1
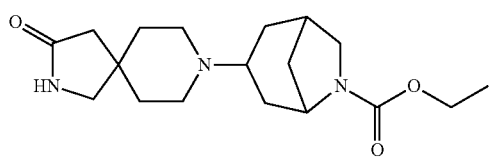 [SMILES: CCOC(=O)N1CC2CC(N3CCC4(CC3)CNC(=O)C4)CC1C2] Example 6-2
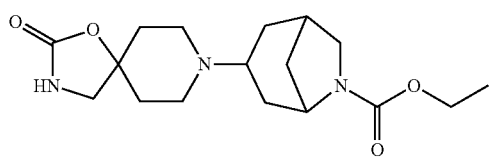 [SMILES: CCOC(=O)N1CC2CC(N3CCC4(CC3)CNC(=O)O4)CC1C2] Example 6-3
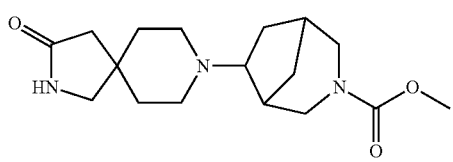 [SMILES: COC(=O)N1CC2CC(C1)C(N1CCC3(CC1)CNC(=O)C3)C2] Example 7-1
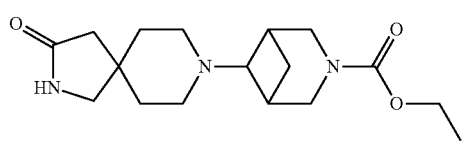 [SMILES: CCOC(=O)N1CC2CC(C1)C2N1CCC2(CC1)CNC(=O)C2] Example 8-1
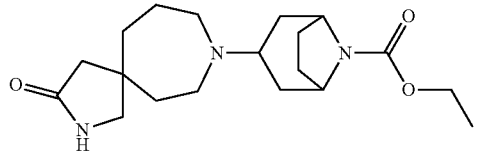 [SMILES: CCOC(=O)N1C2CCC1CC(N1CCCC3(CC1)CNC(=O)O3)C2] Example 9-1
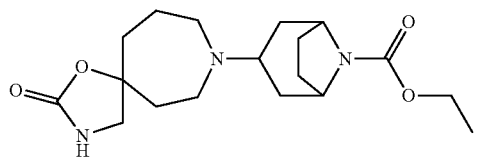 Example 9-2
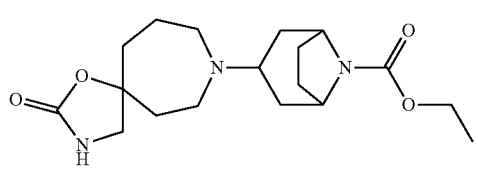 [SMILES: CCOC(=O)N1C2CCC1CC(N1CCCC3(CC1)CNC(=O)O3)C2] Example 9-2

General Procedures

Where no preparative routes are included, the relevant intermediate is commercially available. Commercial reagents were utilized without further purification. Room temperature (rt) refers to approximately 20-27° C. $^1$H NMR spectra were recorded at 300 or 400 MHz on either a Bruker or Varian instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and Silica gel F254 (Merck) as a stationary phase. Microwave-mediated reactions were performed in Biotage Initiator or CEM Discover microwave reactors.

LCMS experiments were typically carried out using electrospray conditions as specified for each compound under the following conditions:

LCMS Methods A and B

Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method A: 0.00/2, 0.10/2, 2.50/95, 3.50/95, 3.55/2, 4.00/2 or Method B: 0.00/2, 0.10/2, 8.40/95, 9.40/95, 9.50/2, 10.00/2; Solvents: solvent C=2.5 L H$_2$O+2.5 mL ammonia solution; solvent D=2.5 L MeCN+135 mL H$_2$O+2.5 mL ammonia solution); Injection volume 3 μL; UV detection 230 to 400 nM; column temperature 45° C.; Flow rate 1.5 mL/min.

LCMS Method C

Instruments: Agilent 1260 Infinity LC with Diode Array Detector, Agilent 6120B Single Quadrupole MS with API-ES Source; Column: Phenomenex Gemini-NX C-18, 3 micron, 2.0×30 mm; Gradient [time (min)/solvent B in A (%)]: Method: 0.00/5, 2.00/95, 2.50/95, 2.60/5, 3.00/5; Solvents: solvent A=2.5 L H$_2$O+2.5 mL of (28% NH3 in H$_2$O); solvent B=2.5 L MeCN+129 mL H$_2$O+2.7 mL of (28% NH3 in H$_2$O); Injection volume 0.5 μL; UV detection 190 to 400 nM; column temperature 40° C.; Flow rate 1.5 m L/m in.

LCMS Methods D and E

Instruments: HP 1100 with G1315A DAD, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method D: 0.00/2, 0.10/2, 2.50/95, 3.50/95, 3.55/2, 4.00/2 or Method E: 0.00/2, 0.10/2, 8.40/95, 9.40/95, 9.50/2, 10.00/2; Solvents: solvent C=2.5 L H$_2$O+2.5 mL 28% ammonia in H$_2$O solution; solvent D=2.5 L MeCN+135 mL H$_2$O+2.5 mL 28% ammonia in H$_2$O solution); Injection volume 1 μL; UV detection 230 to 400 nM; Mass detection 130 to 800 AMU (+ve and −ve electrospray); column temperature 45° C.; Flow rate 1.5 mL/min.

LCMS Method F:

Instruments: Waters Acquity H Class, Photo Diode Array, SQ Detector; Column: BEH C18, 1.7 micron, 2.1×50 mm; Gradient [time (min)/solvent B in A (%)]: 0.00/5, 0.40/5, 0.8/35, 1.20/55, 2.50/100, 3.30/100 4.00/5; Solvents: solvent A=5 mM ammonium acetate and 0.1% formic acid in H$_2$O; solvent B=0.1% formic acid in MeCN; Injection volume 2 μL; UV detection 200 to 400 nM; Mass detection 100 to 1200 AMU (+ve electrospray); column at ambient temperature; Flow rate 0.5 mL/min.

LCMS Method G:

Instruments: Waters 2695, Photo Diode Array, ZQ-2000 Detector; Column: X-Bridge C18, 5 micron, 150×4.6 mm; Gradient [time (min)/solvent B in A (%)]: 0.00/10, 5.00/90, 7.00/100, 11.00/100, 11.01/10 12.00/10; Solvents: solvent A=0.1% ammonia in H$_2$O; solvent B=0.1% ammonia in MeCN; Injection volume 10 μL; UV detection 200 to 400 nM; Mass detection 60 to 1000 AMU (+ve electrospray); column at ambient temperature; Flow rate 1.0 mL/min.

LCMS Method H:

Instruments: Waters 2695, Photo Diode Array, ZQ-2000 Detector; Column: X-Bridge C18, 5 micron, 150×4.6 mm; Gradient [time (min)/solvent B in A (%)]: 0.00/100, 7.00/50, 9.00/0, 11.00/0, 11.01/100, 12.00/100; Solvents: solvent A=0.1% ammonia in H$_2$O; solvent B=0.1% ammonia in MeCN; Injection volume 10 μL; UV detection 200 to 400 nM; Mass detection 60 to 1000 AMU (+ve electrospray); column at ambient temperature; Flow rate 1.0 mL/min.

LCMS Method I:

Instruments: Waters Acquity UPLC, Waters 3100 PDA Detector, SQD; Column: Acquity HSS-T3, 1.8 micron, 2.1×100 mm; Gradient [time (min)/solvent B in A (%)]: 0.00/10, 1.00/10, 2.00/15, 4.50/55, 6.00/90, 8.00/90, 9.00/10, 10.00/10; Solvents: solvent A=0.1% trifluoroacetic acid in water; solvent B=acetonitrile; Injection volume 14; Detection wavelength 214 nm; Column temperature 30° C.; Flow rate 0.3 mL per min.

LCMS Method J:

Instruments: Waters 2695, Photo Diode Array, ZQ-2000 Detector; Column: X-Bridge C18, 3.5 micron, 50×4.6 mm; Gradient [time (min)/solvent B in A (%)]: 0.01/0, 0.20/0, 5.00/90, 5.80/95, 7.20/95, 7.21/100, 10.00/100; Solvents: solvent A=0.1% ammonia in H$_2$O; solvent B=0.1% ammonia in MeCN; Injection volume 10 μL; UV detection 200 to 400 nM; Mass detection 60 to 1000 AMU (+ve electrospray); column at ambient temperature; Flow rate 1.0 mL/min.

LCMS data in the experimental section are given in the format: Mass ion, retention time, UV activity.

Abbreviations d=day(s)
DCE=dichloroethane
DCM=dichloromethane
DIPEA=diisopropylethylamine
DMF=dimethylformamide
DMSO=dimethylsulfoxide
DPPA=diphenylphosphorylazide
ES=electro spray ionisation
Et$_3$N=triethylamine
EtOAc=ethyl acetate
h=hour(s)
HPLC=high performance liquid chromatography
LC=liquid chromatography
LDA=Lithium diisopropylamide
LiHMDS=Lithium bis(trimethylsilyl)amide
MeCN=acetonitrile
MeOH=methanol
min=minute(s)
MS=mass spectrometry
N$_2$=nitrogen NaCNBH$_3$=sodium cyanoborohydride
NMR=nuclear magnetic resonance
rt=room temperature
sat.=saturated
sol.=solution
SFC=supercritical fluid chromatography
STAB=sodium triacetoxyborohydride
TBAF=tetra butyl ammonium fluoride
THF=tetrahydrofuran
TLC=thin layer chromatography Prefixes n-, s-, i-, t- and tert- have their usual meanings: normal, secondary, iso, and tertiary.

Synthesis of Intermediates:
Route 1

Typical Procedure for the Preparation of Piperidines, as Exemplified by the Preparation of Intermediate 3, 1-ethyl-2,8-diazaspiro[4.5]decan-3-one.HCl

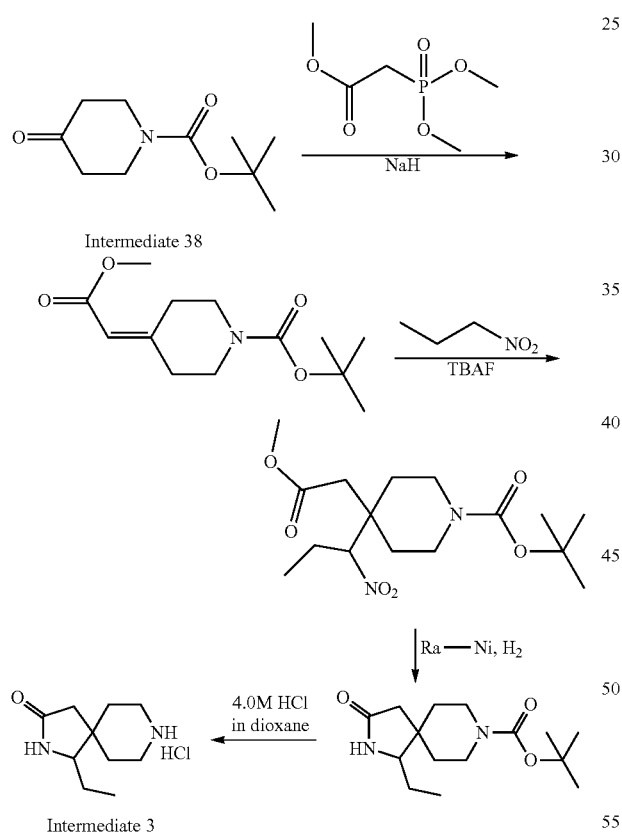

Intermediate 3

Sodium hydride in mineral oil (60%, 11.9 g, 297 mmol) was dissolved in DMF (200 mL) and methyl 2-(dimethoxyphosphoryl)acetate (52.0 g, 286 mmol) was added drop wise at 0° C. The reaction mixture was stirred at 0° C. for 20 min then tert-butyl 4-oxopiperidine-1-carboxylate (45.5 g, 228 mmol) in DMF (100 mL) was added drop wise at 0° C. The reaction mixture was stirred at rt for 2 h, then diluted with ice water (20 mL), filtered and the solvents were removed in vacuo to give tert-butyl 4-(2-methoxy-2-oxoethylidene)piperidine-1-carboxylate (42.5 g, 72.9%) as a yellow solid.

LCMS (Method F): m/z 256 (M+H)$^+$ (ES$^+$), at 2.47 min, UV active tert-Butyl 4-(2-methoxy-2-oxoethylidene)piperidine-1-carboxylate (5.0 g, 19.60 mmol) was dissolved in THF (50.0 mL) then 1.0M TBAF in THF (25.5 mL, 25.5 mmol) was added drop wise to reaction mixture followed by 1-nitro propane (2.62 g, 29.4 mmol), the reaction mixture was heated to 70° C. for 24 h. Reaction mixture was poured onto ice cold water (150 mL), extracted by EtOAc (500 mL), aqueous layer was further extracted with EtOAc (2×250 mL), organic layers were combined, dried (Na$_2$SO$_4$). Solvents were removed in vacuo and the residue was purified by column chromatography (normal phase silica, 0 to 6% EtOAc in Hexane) to give tert-butyl 4-(2-methoxy-2-oxoethyl)-4-(1-nitropropyl) piperidine-1-carboxylate (1.1 g, 40.9%) as yellow oil.

LCMS (Method F): m/z 345 (M+H)$^+$ (ES$^+$), at 2.43 min, UV inactive tert-Butyl 4-(2-methoxy-2-oxoethyl)-4-(1-nitropropyl)piperidine-1-carboxylate (0.7 g, 2.03 mmol) was dissolved in MeOH (15 mL) and Raney®-Nickel (140.0 mg, 20% w/w) was added. The reaction mixture was purged with H$_2$ gas and then stirred at rt for 16 h. The reaction mixture was filtered through celite and solvents were removed in vacuo to give tert-butyl 1-ethyl-3-oxo-2,8-diazaspiro[4.5]decane-8-carboxylate (0.28 g, 48.0%) as white solid.

LCMS (Method F): m/z 283 (M+H)$^+$ (ES$^+$), at 1.95 min, UV inactive tert-Butyl 1-ethyl-3-oxo-2,8-diazaspiro[4.5]decane-8-carboxylate (0.27 g, 0.96 mmol) was dissolved 4.0 M HCl in 1,4-dioxane (5.0 mL) at room temperature. The reaction mixture was stirred at rt for 16 h and then solvents were removed in vacuo. Residue was triturated with diethyl ether to give 1-ethyl-2,8-diazaspiro[4.5]decan-3-one.HCl, Intermediate 3 (0.15 g, 84.7%) as white solid.

The data for the title compound are in Table 2

Route 2

Typical Procedure for the Preparation of Ketones, as Exemplified by the Preparation of Intermediate 6, 6-fluoro-2,8-diazaspiro[4.5]decan-3-one.HCl

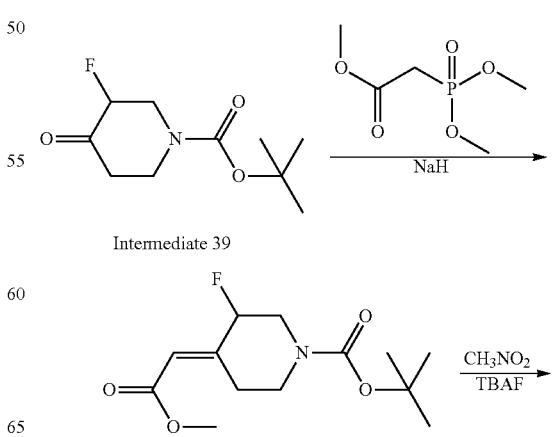

Intermediate 39

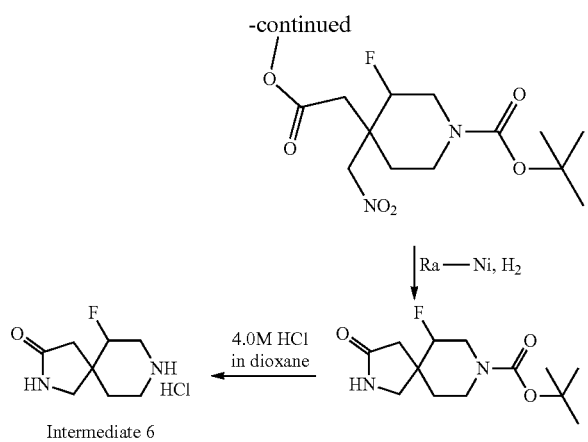

Sodium hydride in mineral oil (60%, 0.18 g, 4.6 mmol) was suspended in THF (12 mL) and methyl 2-(dimethoxyphosphoryl)acetate (0.84 g, 4.6 mmol) was added drop wise at 0° C. The reaction mixture was stirred at 0° C. for 1 h then tert-butyl-3-fluoro-4-oxo-piperidine-1-carboxylate (1.0 g, 4.6 mmol) in THF (5 mL) was added drop wise at 0° C. The reaction mixture was stirred at rt for 16 h, then quenched with water (10 mL). The reaction mixture was extracted with EtOAc (3×20 mL), the organic layers were combined and washed with sat. NaHCO₃ sol. (20 mL) and brine (20 mL) then dried (Na₂SO₄). The solvents were removed in vacuo and the residue was purified by column chromatography (normal phase, [Biotage SNAP cartridge KP-sil 25 g, 40-63 μm, 60 Å, 25 mL per min, gradient 0% to 35% EtOAc in Isohexane]) to give tert-butyl 3-fluoro-4-(2-methoxy-2-oxoethylidene)piperidine-1-carboxylate (0.94 g, 75%).

¹H NMR: (400 MHz, DMSO-d₆) δ: 1.39 (d, J=2.5 Hz, 9H), 2.20-2.35 (m, 1H), 2.74-2.96 (m, 2H), 3.64 (d, J=2.0 Hz, 3H), 4.02-4.20 (m, 1H), 4.22-4.43 (m, 1H), 5.05 (ddd, J=47.5, 4.5, 3.5 Hz, 1H), 5.98 (s, 1H), 6.19 (s, 0.5H), 6.31 (s, 0.5H)

tert-Butyl 3-fluoro-4-(2-methoxy-2-oxoethylidene)piperidine-1-carboxylate (0.94 g, 3.5 mmol) and nitromethane (0.32 g, 5.2 mmol) were dissolved in 1.0 M TBAF in THF (10 mL), the reaction mixture was heated at 50° C. under N₂ for 2 d. The solvents were removed in vacuo and the residue was purified by column chromatography (normal phase, [Biotage SNAP cartridge KP-sil 25 g, 40-63 μm, 60 Å, 25 mL per min, gradient 0% to 40% EtOAc in Isohexane]) to give tert-butyl 3-fluoro-4-(2-methoxy-2-oxoethyl)-4-(nitromethyl)piperidine-1-carboxylate (0.47 g, 41%).

¹H NMR: (400 MHz, DMSO-d₆) δ: 1.37 (s, 9H), 1.59-1.74 (m, 2H), 2.62-2.71 (m, 1H), 2.71-2.83 (m, 1H), 2.94-3.08 (m, 1H), 3.16-3.28 (m, 1H), 3.60 (s, 3H), 3.66-3.84 (m, 1H), 3.94-4.07 (m, 1H), 4.64-4.71 (m, 1H), 4.71-4.86 (m, 2H)

tert-Butyl 3-fluoro-4-(2-methoxy-2-oxoethyl)-4-(nitromethyl)piperidine-1-carboxylate (0.47 g, 1.41 mmol) was dissolved in EtOH (50 mL) and passed three times through an H-Cube® fitted with a ThalesNano CatCart® catalyst cartridge system, 70 mm Raney®-Nickel (THS01132) at 40 Bar and 50° C. The solvents were removed in vacuo to give tert-butyl 6-fluoro-3-oxo-2,8-diazaspiro[4.5]decane-8-carboxylate (0.35 g, 85%) as a white solid which was used without further purification.

¹H NMR: (400 MHz, DMSO-d₆) δ: 1.37 (s, 9H), 1.42-1.56 (m, 1H), 1.56-1.74 (m, 1H), 2.12 (s, 2H), 2.84-2.92 (m, 1H), 2.94-3.06 (m, 1H), 3.06-3.21 (m, 1H), 3.28 (d, J=9.5 Hz, 1H), 3.71-3.83 (m, 1H), 3.83-4.02 (m, 1H), 4.41-4.60 (m, 1H), 7.58-7.70 (m, 1H)

tert-butyl 6-fluoro-3-oxo-2,8-diazaspiro[4.5]decane-8-carboxylate (0.35 g, 1.27 mmol) was suspended in 4 M HCl in 1,4-dioxane (10 mL) and stirred at rt for 16 h. The solvents were removed in vacuo to give 6-fluoro-2,8-diazaspiro[4.5]decan-3-one.HCl, Intermediate 6 (0.27 g, assume 100%) as a white solid which was used without further purification.

The data for the title compound are in Table 2

Route 3

For the Preparation of Intermediate 7, 2-ethyl-2,8-diazaspiro[4.5]decan-3-one.HCl

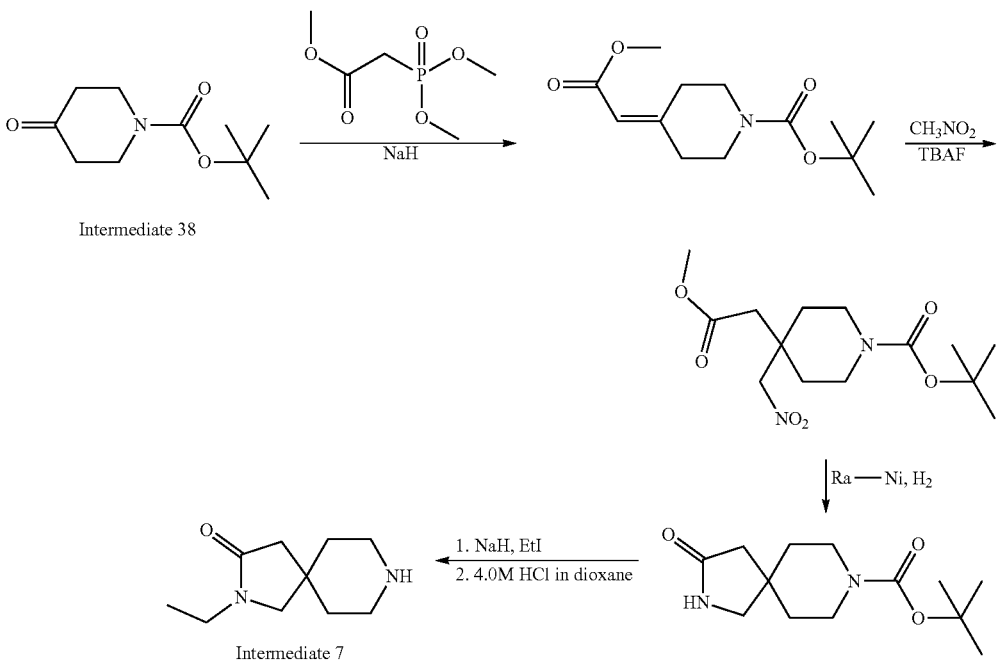

Sodium hydride in mineral oil (60%, 11.9 g, 297 mmol) was dissolved in DMF (200 mL) and methyl 2-(dimethoxyphosphoryl)acetate (52.0 g, 286 mmol) was added drop wise at 0° C. The reaction mixture was stirred at 0° C. for 20 min then tert-butyl 4-oxopiperidine-1-carboxylate (45.5 g, 228 mmol) in DMF (100 mL) was added drop wise at 0° C. The reaction mixture was stirred at rt for 2 h, then diluted with ice water (20 mL), filtered and the solvents were removed in vacuo to give tert-butyl 4-(2-methoxy-2-oxoethylidene)piperidine-1-carboxylate (42.5 g, 72.9%) as a yellow solid.

LCMS (Method F): m/z 256 (M+H)$^+$ (ES$^+$), at 2.47 min, UV active tert-Butyl 4-(2-methoxy-2-oxoethylidene)piperidine-1-carboxylate (42.5 g, 166 mmol) and nitro methane (11.2 g, 183 mmol) were dissolved in THF (200 mL), 1.0 M solution of TBAF in THF (250 mL, 250 mmol) was added drop wise at 0° C. The reaction mixture was refluxed at 70° C. for 16 h. The reaction mixture was partitioned between H$_2$O (150 mL) and EtOAc (90 mL), the aqueous layer was further extracted with EtOAc (2×90 mL); the organic layers were combined and dried (Na$_2$SO$_4$). The solvent was removed in vacuo and the residue was purified by column chromatography (normal-phase silica, 0 to 30% EtOAc in Hexanes) to give tert-butyl 4-(2-methoxy-2-oxoethyl)-4-(nitromethyl)piperidine-1-carboxylate (40.3 g, 76.5%) as a white solid.

LCMS (Method F): m/z 261 (M+H-56)$^+$ (ES$^+$), at 2.30 min, UV inactive tert-Butyl 4-(2-methoxy-2-oxoethyl)-4-(nitromethyl) piperidine-1-carboxylate (40.0 g, 126 mmol) and Raney-Nickel (40.0 g) were dissolved in EtOH (800 mL) and the reaction mixture was purged with H$_2$ gas for 16 hrs. The reaction mixture was filtered through celite, washed with MeOH and the solvent was removed in vacuo. The residue was purified by column chromatography (normal-phase silica, 0 to 4% MeOH in DCM) to give tert-butyl 3-oxo-2,8-diazaspiro[4.5]decane-8-carboxylate (22.9 g, 71.2%) as a white solid.

LCMS (Method F): m/z 255 (M+H)$^+$ (ES$^+$), at 1.81 min, UV inactive

60% NaH (0.63 g, 15.7 mmol) was dissolved in DMF (15.0 mL) and tert-butyl 3-oxo-2,8-diazaspiro[4.5]decane-8-carboxylate (1.00 g, 3.92 mmol) in DMF (5 mL) was added drop wise at 0° C. The reaction mixture was stirred at 0° C. for 30 min, then ethyl iodide (0.48 mL, 5.88 mmol) was added drop wise and the reaction mixture was allowed to warm to rt and stirred for 1 h. The reaction mixture was partitioned between H$_2$O (30 mL) and EtOAc (25 mL), the aqueous layer was further extracted with EtOAc (2×25 mL), the organic layers were combined and dried (Na$_2$SO$_4$). The solvent was removed in vacuo and the residue was purified by column chromatography (normal-phase silica, 0 to 3% MeOH in DCM) to give tert-butyl 2-ethyl-3-oxo-2,8-diazaspiro[4.5]decane-8-carboxylate (1.0 g, 90.3%) as a white solid.

LCMS (Method F): m/z 283 (M+H)$^+$ (ES$^+$), at 2.00 min, UV inactive tert-Butyl 2-ethyl-3-oxo-2,8-diazaspiro[4.5]decane-8-carboxylate (1.00 g, 3.54 mmol) was dissolved in 4.0 M HCl in 1,4-dioxane (15.0 mL) and reaction mixture was stirred at rt for 5 h. The solvent was removed in vacuo and the residue was triturated with acetone (3×10 mL) to give 2-ethyl-2,8-diazaspiro[4.5]decan-3-one.HCl, Intermediate 7 (0.55 g, 71.2%) as a white solid.

The data for the title compound are in Table 2

Route 4

Typical Procedure for the Preparation of Piperidines, as Exemplified by the Preparation of Intermediate 12, 4,4-dimethyl-1-oxa-3,8-diazaspiro[4.5]decan-2-one

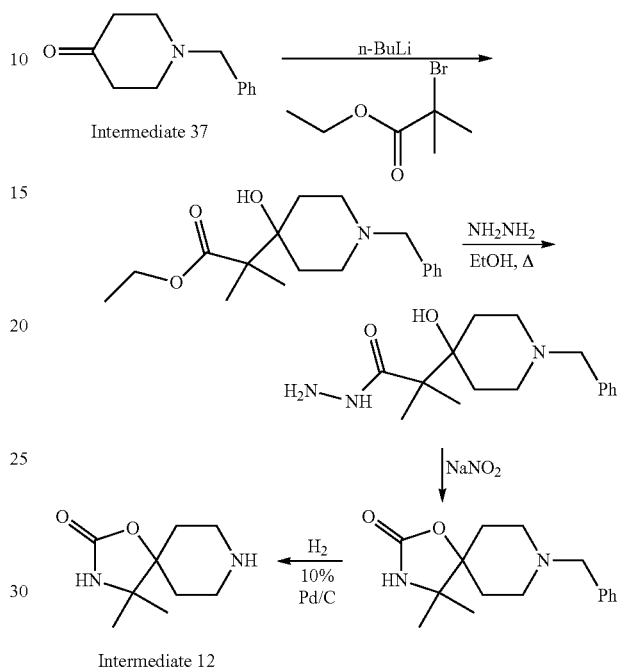

Intermediate 12

2-Bromo-2-methylpropionic acid ethyl ester (15.4 g, 79.2 mmol) was dissolved in Et$_2$O (100 mL) and cooled to −78° C. under N$_2$. n-Butyl lithium (99 mL, 158 mmol) was added drop wise and the reaction mixture was stirred at −78° C. for 1 h. N-benzyl-4-piperidone (10 g, 52.8 mmol) in Et$_2$O (100 mL) was added drop wise and the reaction mixture was stirred at −60° C. for 2 h. The reaction mixture was quenched with sat. NH$_4$Cl sol. (200 mL) and then diluted with water (500 mL). The reaction mixture was extracted with EtOAc (3×200 mL), the organic layers were combined and dried (Na$_2$SO$_4$). The solvent was removed in vacuo and the residue was purified by column chromatography (normal phase, neutral silica gel, 60-120 mesh, 0 to 15% EtOAc in Hexane) to give ethyl 2-(1-benzyl-4-hydroxypiperidin-4-yl)-2-methylpropanoate (12.0 g, 74.3%) as a yellow gum LCMS (Method F): m/z 306 (M+H)$^+$ (ES$^+$), at 1.79 min, UV active Ethyl 2-(1-benzyl-4-hydroxypiperidin-4-yl)-2-methylpropanoate (12.0 g, 39.3 mmol) and 85% hydrazine hydrate (80 mL) were dissolved in EtOH (30 mL). The reaction mixture was refluxed at 100° C. for 120 h. The solvent was removed in vacuo to give 2-(1-benzyl-4-hydroxypiperidin-4-yl)-2-methylpropanohydrazide (15.0 g, 131%) as a yellow gum, which was used crude in the next step.

LCMS (Method F): m/z 292 (M+H)$^+$ (ES$^+$), at 1.37 min, UV active 2-(1-benzyl-4-hydroxypiperidin-4-yl)-2-methylpropanohydrazide (15 g, assumed 39.3 mmol) was dissolved in water (60 mL) and then acidified with conc HCl (5 mL), the reaction mixture was cooled to 5° C. NaNO$_2$ (4.2 g, 61.8 mmol) in water (8 mL) was added at 0° C. and the reaction mixture was warmed to 60° C. for 1 h. The reaction mixture was basified with 20% NaOH solution and diluted with water (500 mL), extracted with EtOAc (3×200 mL), the organic layers were combined and dried (Na$_2$SO$_4$). The solvent was removed in vacuo and the residue was purified by column chromatography (normal phase, neutral silica gel, 60-120 mesh, 0 to 2% MeOH in DCM) to give 8-benzyl-4,4-dimethyl-1-oxa-3,8-diazaspiro[4.5]decan-2-one (5.0 g, 46.4%[over two steps]) as a yellow solid.

LCMS (Method F): m/z 275 (M+H)+ (ES+), at 1.50 min, UV active

8-Benzyl-4,4-dimethyl-1-oxa-3,8-diazaspiro[4.5]decan-2-one (5.0 g, 18.2 mmol) was dissolved in MeOH (30 mL). 10% Pd/C (0.5 g) was added and the reaction mixture was stirred under H₂ atmosphere (1 atm) at 50° C. for 2 h. The reaction mixture was filtered through celite and the solvents was removed in vacuo. The residue was triturated with Et₂O to give 4,4-dimethyl-1-oxa-3,8-diazaspiro[4.5]decan-2-one, Intermediate 12 (1.5 g, 45.4%) as a yellow solid.

The data for the title compound are in Table 2

Route 5

Typical Procedure for the Preparation of Ketones, as Exemplified by the Preparation of Intermediate 16, methyl 3-oxo-8-azabicyclo[3.2.1]octane-8-carboxylate

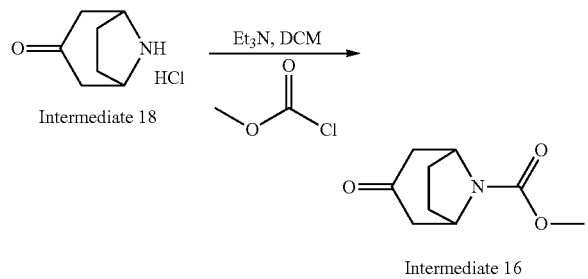

Intermediate 16

Nortropinone. HCl (1.00 g, 6.1 mmol) was suspended in DCM (20 mL) and cooled to 0° C. under N₂, triethylamine (1.25 g, 12.4 mmol) and methyl chloroformate (0.64 g, 6.8 mmol) were added and the reaction mixture was stirred at rt for 16 h. The reaction mixture was diluted with DCM (20 mL) and washed with sat. NaHCO₃ sol. (20 mL) and brine (20 mL) then dried (MgSO₄), the solvents were removed in vacuo. The residue was purified by column chromatography (normal phase, [Biotage SNAP cartridge KP-sil 25 g, 40-63 µm, 60 Å, 25 mL per min, gradient 0% to 6% MeOH in DCM]) to give methyl 3-oxo-8-azabicyclo[3.2.1]octane-8-carboxylate, Intermediate 16 (0.88 g, 77.6%) as a pale yellow gum.

The data for the title compound are in Table 2

Route 6

Typical Procedure for the Preparation of Ketones, as Exemplified by the Preparation of Intermediate 34, ethyl 3-oxo-6-azabicyclo[3.2.1]octane-6-carboxylate

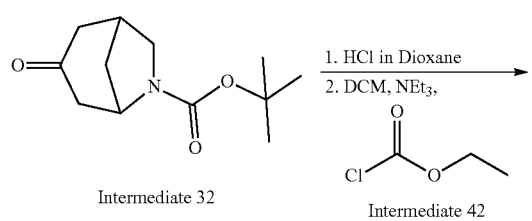

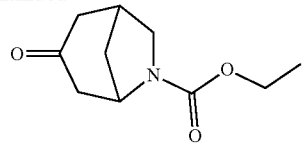

Intermediate 34 tert-Butyl 3-oxo-6-azabicyclo[3.2.1]octane-6-carboxylate (0.60 g, 2.7 mmol) was added portionwise to 4.0 M HCl in 1,4-Dioxane (10 mL, 40 mmol), the reaction mixture was stirred at rt for 24 h and then the solvents were removed in vacuo. The residue was dissolved in DCM (10 mL) and Et₃N (0.75 mL, 5.4 mmol) and cooled to 0° C. Ethyl chloroformate (0.28 mL, 3.0 mmol) was added drop wise and the reaction mixture was stirred at rt for 18 h. The reaction mixture was partitioned between DCM (10 mL) and sat. NaHCO₃ sol. (10 mL), the aqueous layer was extracted with DCM (2×10 mL). The organic layers were combined and washed with brine (10 mL), dried over (MgSO₄), and the solvents were removed in vacuo to give ethyl 3-oxo-6-azabicyclo[3.2.1]octane-6-carboxylate, Intermediate 34 (0.43 g, 81%) as an yellow gum.

The data for the title compound are in Table 2

Route 7

Typical Procedure for the Preparation of Activated Carbamates, as Exemplified by the Preparation of Intermediate 58, 4-nitrophenyl 3-(3-oxo-2,8-diazaspiro[4.5]dec-8-yl)-8-azabicyclo[3.2.1]octane-8-carboxylate

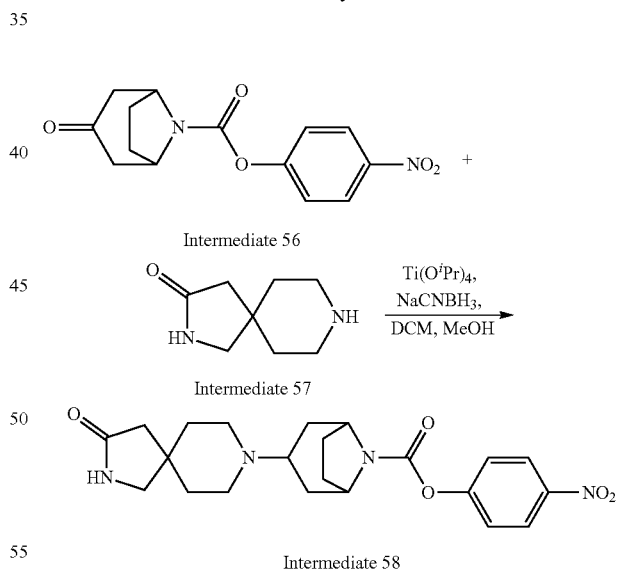

2,8-Diazaspiro[4.5]decan-3-one (1.12 g, 7.24 mmol) and 4-nitrophenyl 3-oxo-8-azabicyclo[3.2.1]octane-8-carboxylate (2.10 g, 7.24 mmol) were dissolved in DCM (10 mL), treated with titanium (IV) isopropoxide (2.57 g, 9.05 mmol), then stirred at rt under nitrogen overnight. The reaction mixture was diluted with MeOH (30 mL) and NaCNBH₃ (0.91 g, 14.48 mmol) was added and the reaction mixture was stirred at rt under nitrogen overnight. Water (10 mL) and DCM (10 mL) were added and the solution was passed through a celite pad to remove solids. The filtrate was separated and the aqueous phase was extracted with DCM (3×25 mL). The organic phases were combined and washed with sat. NaHCO$_3$ sol. (25 ml) and dried by passing down a Biotage Phase Separator cartridge. The solvents were removed in vacuo, and the residue was purified by column chromatography (normal phase, [Biotage SNAP cartridge KP-sil 10 g, 40-63 μm, 60 Å, 10 mL per min, gradient 0% to 10% MeOH in DCM]) to give 4-nitrophenyl 3-(3-oxo-2,8-diazaspiro[4.5]dec-8-yl)-8-azabicyclo[3.2.1]octane-8-carboxylate, Intermediate 58 as a mixture of diastereoisomers, (204 mg, 6.6%) as a yellow glassy solid.

The data for the title compound are in Table 2

Route 8

Typical Procedure for the Preparation of Piperidines, as Exemplified by the Preparation of Intermediate 67, 1-benzyl-1,2,8-triazaspiro[4.5]decan-3-one HCl

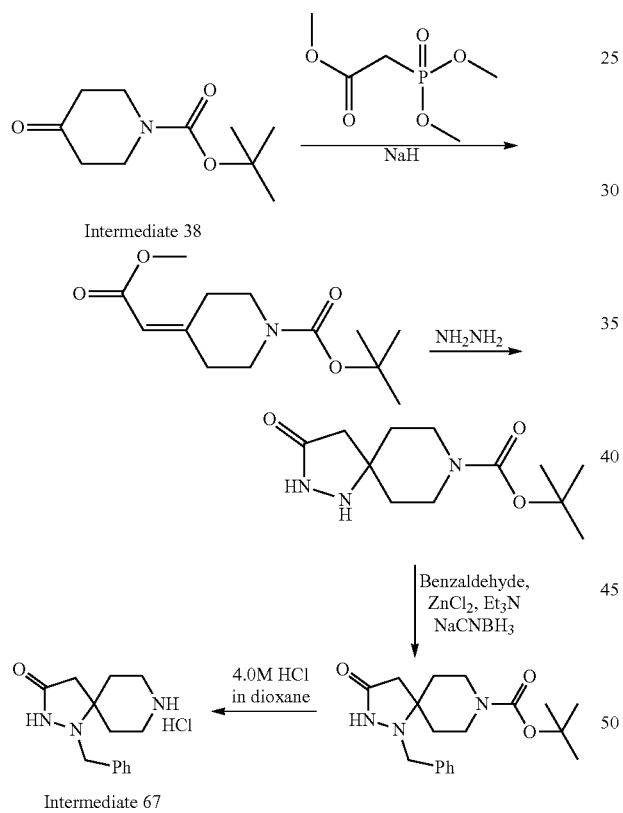

Sodium hydride in mineral oil (60%, 11.9 g, 297 mmol) was dissolved in DMF (200 mL) and methyl 2-(dimethoxyphosphoryl)acetate (52.0 g, 286 mmol) was added drop wise at 0° C. The reaction mixture was stirred at 0° C. for 20 min then tert-butyl 4-oxopiperidine-1-carboxylate (45.5 g, 228 mmol) in DMF (100 mL) was added drop wise at 0° C. The reaction mixture was stirred at rt for 2 h, then diluted with ice water (20 mL), filtered and the solvents were removed in vacuo to give tert-butyl 4-(2-methoxy-2-oxoethylidene)piperidine-1-carboxylate (42.5 g, 72.9%) as a yellow solid.

LCMS (Method F): m/z 256 (M+H)$^+$ (ES$^+$), at 2.47 min, UV active

To tert-butyl 4-(2-methoxy-2-oxoethylidene)piperidine-1-carboxylate (3.0 g, 11.8 mmol) in EtOH (20 mL) was added hydrazine hydrate (1.1 mL, 23.5 mmol) and the reaction mixture was stirred at 80° C. for 8 h. The mixture was partitioned between water (150 mL) and EtOAc (120 mL), the aqueous layer was further extracted with EtOAc (2×120 mL), and combined organics were washed with brine (100 mL) and dried (Na$_2$SO$_4$). The solvents were removed in vacuo and the residue was purified by column chromatography (normal silica, mesh size: 60-120, 4.0% to 10.0% MeOH in DCM) to give tert-butyl 3-oxo-1, 2, 8-triazaspiro [4.5]decane-8-carboxylate (1.78 g, 59.3%) as white solid.

LCMS (Method F): m/z 256 (M+H)$^+$ (ES$^+$), at 1.70 min, UV inactive tert-Butyl 3-oxo-1,2,8-triazaspiro[4.5]decane-8-carboxylate (0.3 g, 1.18 mmol), benzaldehyde (0.12 mL, 1.29 mmol), ZnCl$_2$ (8.0 mg, 0.06 mmol) and Et$_3$N (0.80 mL, 5.89 mmol) were dissolved in MeOH (10 mL) and the reaction mixture stirred at 50° C. for 2 h. The mixture was then cooled to 0° C. before addition of NaCNBH$_3$ (222 mg, 3.52 mmol) portionwise and further stirring at 40° C. for 30 h. The mixture was partitioned between H$_2$O (60 mL) and EtOAc (40 mL), and the aqueous layer further extracted with EtOAc (2×40 mL). Combined organics were dried (Na$_2$SO$_4$), the solvent was removed in vacuo and the crude residue purified by trituration with hexane (3×3 mL) to give tert-butyl 1-benzyl-3-oxo-1,2,8-triazaspiro[4.5]decane-8-carboxylate (320 mg, 79.0%) as a yellow gum.

LCMS (Method G): m/z 346 (M+H)$^+$ (ES$^+$), at 5.91 min, UV active tert-Butyl 1-benzyl-3-oxo-1,2,8-triazaspiro[4.5]decane-8-carboxylate (0.3 g, 0.87 mmol) was dissolved in 1,4-dioxane (2 mL) and 4.0 M HCl in 1,4-dioxane (10 mL) was added drop wise, the reaction mixture was stirred at 30° C. for 16 h. The solvents were removed in vacuo and the residue was purified by triturating with Et$_2$O (3×3 mL) to give 1-benzyl-1,2,8-triazaspiro[4.5]decan-3-one, Intermediate 67 (0.21 g, 98.6%) as an off-white solid.

The data for the title compound are in Table 2

Route 9

Typical Procedure for the Preparation of Ketones as Exemplified by the Preparation of Intermediate 77, S-ethyl 3-oxo-8-azabicyclo[3.2.1]octane-8-carbothioate

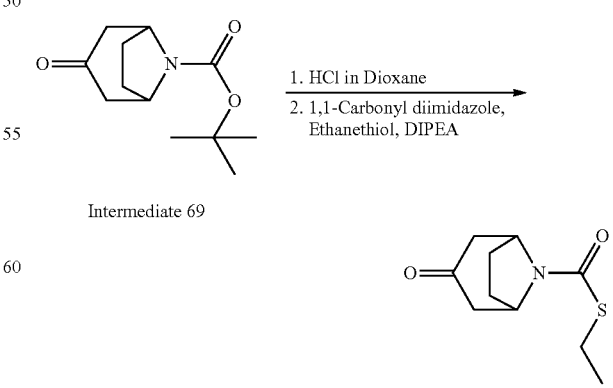

To tert-Butyl 3-oxo-8-azabicyclo[3.2.1]octane-8-carboxylate (1.00 g, 4.4 mmol) in 1,4-dioxane (3 mL) was added 4.0 M HCl in 1,4-dioxane (10 mL, 40 mmol), the reaction mixture was stirred at 30° C. for 7 h and then the solvents were removed in vacuo. To a portion of the residue (0.20 g, 1.3 mmol) in DCM (10 mL) was added DIPEA (0.40 mL, 2.5 mmol), ethanethiol (0.10 mL, 1.8 mmol) and 1,1-carbonyldiimidazole (0.29 g, 1.8 mmol) and the mixture stirred at rt for 18 h. The reaction mixture was partitioned between H$_2$O (100 mL) and EtOAc (70 mL) and the aqueous layer further extracted with EtOAc (2×70 mL). Combined organics were dried over Na$_2$SO$_4$ and the solvent was removed in vacuo. The residue was purified by column chromatography (Normal silica, mesh size: 60-120, 20% to 30% EtOAc in Hexane) to give S-ethyl 3-oxo-8-azabicyclo[3.2.1]octane-8-carbothioate, Intermediate 77 (120 mg, 45.1%) as a yellow oil.

The data for the title compound are in Table 2

Route 10

Typical Procedure for the Preparation of Intermediate 80, 1-oxa-3,8-diazaspiro[4.6]undecan-2-one the resulting mixture stirred at rt for 1 h. The reaction mixture was quenched with a saturated solution of NH$_4$Cl, diluted with water (500 mL), extracted with EtOAc (3×200 mL), and combined organics dried (Na$_2$SO$_4$) and the solvents were removed in vacuo. The crude residue was purified by column chromatography (Normal phase, Neutral silica gel, 60-120 mesh, 0 to 25% EtOAc in hexane) to give ethyl 2-(1-benzyl-4-hydroxyazepan-4-yl)acetate (17.5 g, 67.8%) as a yellow gum.

LCMS (Method F): m/z 293 (M+H)$^+$ (ES$^+$), at 1.60 min

Ethyl 2-(1-benzyl-4-hydroxyazepan-4-yl)acetate (17.5 g, 59.9 mmol) and hydrazine hydrate (100 mL) were stirred at 100° C. for 4 h. The reaction mixture was concentrated in vacuo to give 2-(1-benzyl-4-hydroxyazepan-4-yl)acetohydrazide (22 g crude) as a yellow gum, which was taken on directly to the next step.

LCMS (Method K): m/z 278 (M+H)$^+$ (ES$^+$), at 3.40 min 2-(1-Benzyl-4-hydroxypiperidin-4-yl)acetohydrazide (22.0 g, 79.0 mmol) was dissolved in H$_2$O (120 mL) and acidified with conc. HCl at 0° C. To the reaction mixture was added NaNO$_2$ (14.0 g, 197.6 mmol) in H$_2$O (30 mL) at 0° C. and stirring continued at 60° C. for 1 h. The reaction mixture was basified with 20% NaOH solution, diluted with

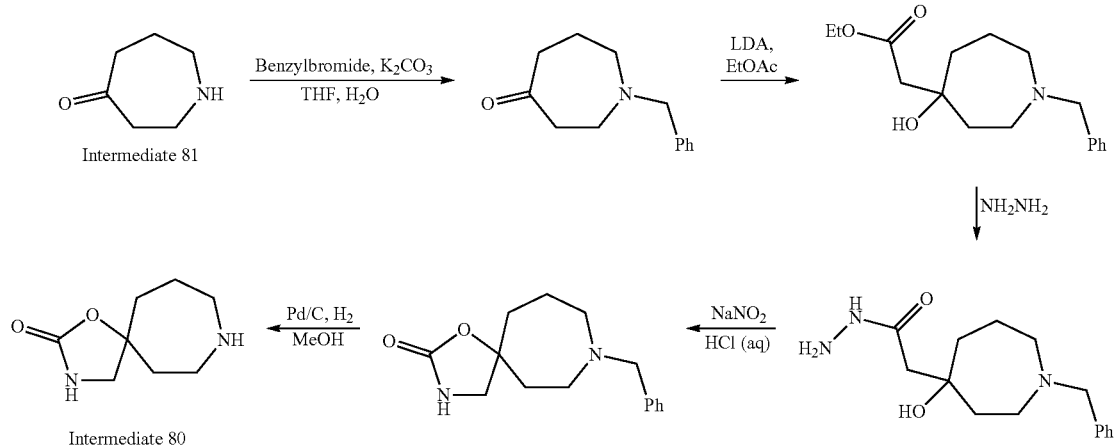

Azepan-4-one HCl (32 g, 214 mmol), benzyl bromide (40 g, 235 mmol), K$_2$CO$_3$ (36 g, 257 mmol) and water (40 mL) were dissolved in THF (160 mL) and stirred at 50° C. for 3 h. The reaction mixture was diluted with H$_2$O (500 mL), extracted with EtOAc (3×200 mL), and combined organics dried (Na$_2$SO$_4$) and the solvents were removed in vacuo. The crude residue was purified by column chromatography (Normal phase, Neutral silica gel, 60-120 mesh, 0 to 15% EtOAc in hexane) to give 1-benzoylazepan-4-one (18.0 g, 41.5%) as a yellow liquid.

LCMS (Method F): m/z 204 (M+H)$^+$ (ES$^+$), at 0.91 min

Diisopropyl amine (24.1 mL, 177.3 mmol) was dissolved in THF (100 mL), cooled to −78° C. under N$_2$, and 1.6 M N-Butyl lithium (89.0 mL, 142.0 mmol) added dropwise at −78° C. The reaction mixture was stirred at 0° C. for 40 min before addition of EtOAc (9.4 g, 160.4 mmol) at −78° C. and further stirring for 10 min. 1-Benzoylazepan-4-one (18 g, 88.6 mmol) in THF (160 mL) was then added at −78° C. and H$_2$O (500 mL), extracted with EtOAc (3×200 mL), and combined organics dried (Na$_2$SO$_4$) and the solvents were removed in vacuo. The crude product was purified by column chromatography (Normal phase, Neutral silica gel, 60-120 mesh, 0 to 8% MeOH in DCM) to give 8-benzyl-1-oxa-3,8-diazaspiro[4.6]undecan-2-one (8.5 g, 41.4%) as a yellow solid.

LCMS (Method F): m/z 261 (M+H)$^+$ (ES$^+$), at 1.44 min

To a solution of 8-benzyl-1-oxa-3,8-diazaspiro[4.6]undecan-2-one (8.5 g, 32.5 mmol) in MeOH (50 mL) was added 10% Pd/C (2.5 g) and the suspension stirred at 60° C. for 2 h at 1 atm H$_2$ pressure. The reaction mixture was filtered through celite and the solvents were removed in vacuo to give 1-oxa-3,8-diazaspiro[4.6]undecan-2-one, Intermediate 80 (5.3 g, 94.8%) as a light yellow solid.

The data for the title compound, are in Table 2

Route 11

Typical Procedure for the Preparation of Piperidines as Exemplified by the Preparation of Intermediate 82, 4-(pyridin-2-ylmethyl)-1-oxa-3,8-diazaspiro[4.5]decan-2-one

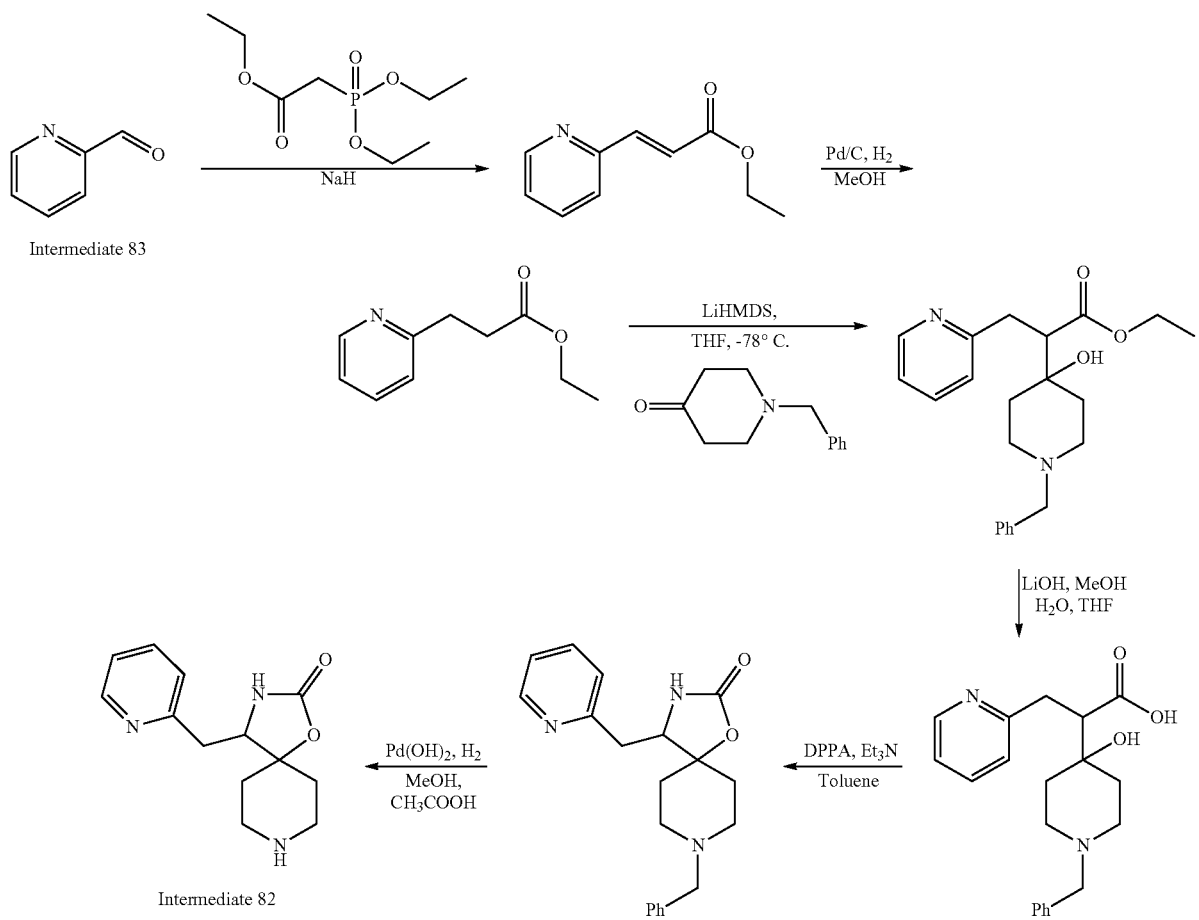

Intermediate 83

Intermediate 82

To a solution of NaH (8.96 g, 50% in mineral oil, 186.9 mmol) in THF (160 mL), triethylphosphonoacetate (20.5 mL, 102.7 mmol) was added at 0° C. After stirring for 1 h at 0° C., picolinaldehyde (10.00 g, 93.4 mmol) was slowly added at 0° C. and the reaction mixture was stirred at rt for 2 h. The reaction mixture was quenched with $H_2O$ (10 mL) and the aqueous layer was extracted with EtOAc (3×100 mL). The organic layers were combined, dried ($Na_2SO_4$) and the solvents were removed in vacuo. The crude residue was purified by flash column chromatography [normal phase, silica gel (100-200 mesh), gradient 10% to 30% EtOAc in hexane] to give ethyl (E)-3-(pyridin-2-yl)acrylate (7.90 g, 49%) as a liquid.

m/z ($ES^+$): 178 $(M+H)^+$

To a solution of ethyl (E)-3-(pyridin-2-yl)acrylate (7.9 g, 23.0 mmol) in MeOH (100 mL), 10% Pd/C (0.80 g, 50% wet) was added and the reaction mixture was stirred under $H_2$ (1 atm) at rt for 16 h. The reaction mixture was filtered through a pad of celite, thoroughly washed with MeOH and the solvents were removed in vacuo to give ethyl 3-(pyridin-2-yl)propanoate (7.8 g, 98%) as a liquid.

m/z ($ES^+$): 179 $(M+H)^+$

To a solution ethyl 3-(pyridin-2-yl)propanoate (2.90 g, 16.2 mmol) in THF (60 mL), LiHMDS (1 M, 48.6 mL, 48.6 mmol) was slowly added at −78° C. and stirred for 30 min, followed by addition of 1-benzylpiperidin-4-one (3.10 g, 16.2 mmol) at −78° C. and the reaction mixture was stirred at −78° C. for 4 h. After completion, the reaction mixture was quenched with sat $NH_4Cl$ solution (30 mL) and the aqueous layer was extracted with EtOAc (3×30 mL). The organic layers were combined, dried ($Na_2SO_4$) and the solvents were removed in vacuo. The crude residue was purified by flash column chromatography [normal phase, silica gel (100-200 mesh), gradient 10% to 30% EtOAc in hexane] to give ethyl 2-(1-benzyl-4-hydroxypiperidin-4-yl)-3-(pyridin-2-yl)propanoate (2.80 g, 50%) as a liquid.

m/z ($ES^+$): 369 $(M+H)^+$

To a solution of ethyl 2-(1-benzyl-4-hydroxypiperidin-4-yl)-3-(pyridin-2-yl)propanoate (2.80 g, 7.61 mmol) in MeOH:THF (1:1, 30 mL), $LiOH.H_2O$ (1.28 g, 30.4 mmol) in water (10 mL), was added at rt and the reaction mixture was stirred for 16 h. The reaction mixture was acidified with glacial acetic acid and extracted with EtOAc (3×20 mL). The organic layers were combined and washed with brine, dried ($Na_2SO_4$) and the solvents were removed in vacuo to give 2-(1-benzyl-4-hydroxypiperidin-4-yl)-3-(pyridin-2-yl)propanoic acid (2.16 g, 84%) as a pale yellow solid.

m/z (ES+): 339 (M+H)+

To a solution of 2-(1-benzyl-4-hydroxypiperidin-4-yl)-3-(pyridin-2-yl)propanoic acid (1.70 g, 5.11 mmol) in toluene (30 mL) was added DPPA (1.32 mL, 6.13 mmol) and Et$_3$N (0.84 mL, 6.13 mmol) and the reaction mixture was heated at 80° C. for 16 h. The reaction mixture was cooled to rt and the solvents were removed in vacuo. The residue was purified by flash column chromatography [normal phase, silica gel (100-200 mesh), gradient 1% to 30% EtOAc in hexane] to give 8-benzyl-4-(pyridin-2-ylmethyl)-1-oxa-3,8-diazaspiro[4.5]decan-2-one (1.25 g, 56%) as a white solid.

m/z (ES+): 338 (M+H)+

To a solution of 8-benzyl-4-(pyridin-2-ylmethyl)-1-oxa-3,8-diazaspiro[4.5]decan-2-one (0.80 g, 2.37 mmol) in MeOH (40 mL), after degassing under N$_2$, 10% Pd(OH)$_2$ on charcoal (0.15 g, 50% wet) was added. The reaction mixture was stirred under H$_2$ (1 atm) at rt for 16 h. After completion, the reaction mixture was filtered through a pad of celite, thoroughly washed with MeOH and the solvents were removed in vacuo to give 4-(pyridin-2-ylmethyl)-1-oxa-3,8-diazaspiro[4.5]decan-2-one, Intermediate 83 (0.58 g, 98%) as a liquid.

The data for the title compound, are in Table 2

Route 12

Typical Procedure for the Preparation of Piperidines as Exemplified by the Preparation of Intermediate 88, 4-(2,2,2-trifluoroethyl)-1-oxa-3,8-diazaspiro[4.5]decan-2-one

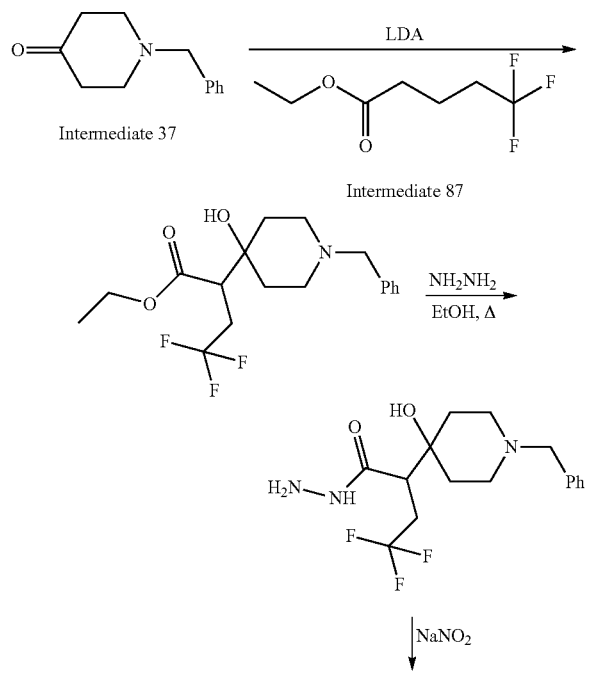

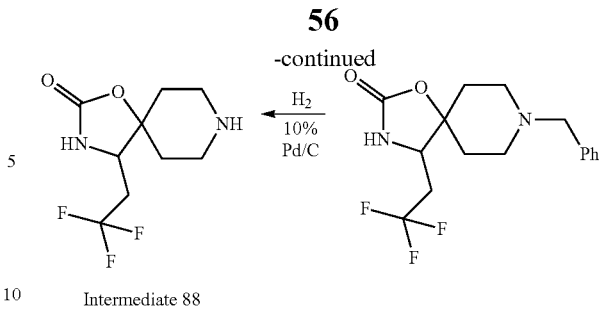

Intermediate 88

Diisopropyl amine (12.8 g, 126.98 mmol) was dissolved in THF (100 mL) and cooled to −78° C. under nitrogen. n-Butyl lithium (79.3 mL, 126.98 mmol, 1.6 M in THF) was added dropwise and the reaction mixture was stirred at −78° C. for 1 h. Ethyl 4,4,4-trifluorobutanoate (16.2 g, 95.23 mmol) was added over 30 min then the reaction mixture was stirred at −78° C. for 1 h. N-benzyl piperidone (15 g, 79.36 mmol) was added dropwise and the reaction mixture was stirred at −78° C. for 30 minutes. The reaction was quenched with a saturated solution of NH$_4$Cl (200 mL), diluted with water (500 mL) and extracted with EtOAc (3×200 mL), the combined organic layers were dried (Na$_2$SO$_4$) and the solvents were removed in vacuo. The residue was purified by column chromatography (Normal phase, Neutral silica gel, 60-120 mesh, 0 to 25% EtOAc in Hexane) to give ethyl 2-(1-benzyl-4-hydroxypiperidin-4-yl)-4,4,4-trifluorobutanoate (24.0 g, 84.2%) as a yellow gum.

LCMS (Method F): m/z 360 (M+H)+ (ES+), at 1.75 min, UV active

Ethyl 2-(1-benzyl-4-hydroxypiperidin-4-yl)-4,4,4-trifluorobutanoate (24.0 g, 66.85 mmol) and 85% hydrazine hydrate (200 mL) were dissolved in ethanol (100 mL). The reaction mixture was refluxed and allowed to stir at 100° C. for 72 h. The reaction mixture was concentrated in vacuo to give the crude product of 2-(1-benzyl-4-hydroxypiperidin-4-yl)-4,4,4-trifluorobutanehydrazide (28.0 g) as a yellow gum. The crude product was used in the next step without any purification.

LCMS (Method F): m/z 346 (M+H)+ (ES+), at 1.41 min, UV active

Crude 2-(1-benzyl-4-hydroxypiperidin-4-yl)-4,4,4-trifluorobutanehydrazide (28 g, 81.1 mmol) was dissolved in water (200 mL), acidified with conc HCl and cooled to 0° C. NaNO$_2$ (16.7 g, 243.2 mmol) in water (50 mL) was added at 0° C. and the reaction mixture was allowed to stir at 60° C. for 1 h. The reaction was basified with 20% NaOH solution, diluted with water (500 mL) and extracted with EtOAc (3×200 mL), the combined organic layers were dried (Na$_2$SO$_4$) and the solvents were removed in vacuo. The residue was purified by column chromatography (Normal phase, Neutral silica gel, 60-120 mesh, 0 to 3.0% MeOH in dichloromethane) to give 8-benzyl-4-(2,2,2-trifluoroethyl)-1-oxa-3,8-diazaspiro[4.5]decan-2-one (1.2 g, 4.5%) as a yellow solid.

LCMS (Method F): m/z 329 (M+H)+ (ES+), at 1.48 min, UV active

8-Benzyl-4-(2,2,2-trifluoroethyl)-1-oxa-3,8-diazaspiro[4.5]decan-2-one (1.2 g, 3.65 mmol) was dissolved in methanol (30 mL). Pd/C (300 mg, 10% Pd/C 50% moisture) was added and the reaction mixture was stirred under a hydrogen atmosphere (1 atm) at 50° C. for 2 h. The reaction mixture was filtered through celite and the solvents were removed in vacuo. The crude product was triturated with diethyl ether to give 4-(2,2,2-trifluoroethyl)-1-oxa-3,8-diazaspiro[4.5]decan-2-one, Intermediate 88 (0.75 g, 88.2%) as a yellow solid The data for the title compound are in Table 2.

Route 13

Typical Procedure for the Preparation of Piperidines, as Exemplified by the Preparation of Intermediate 88, 1-propyl-1,2,8-triazaspiro[4.5]decan-3-one.HCl

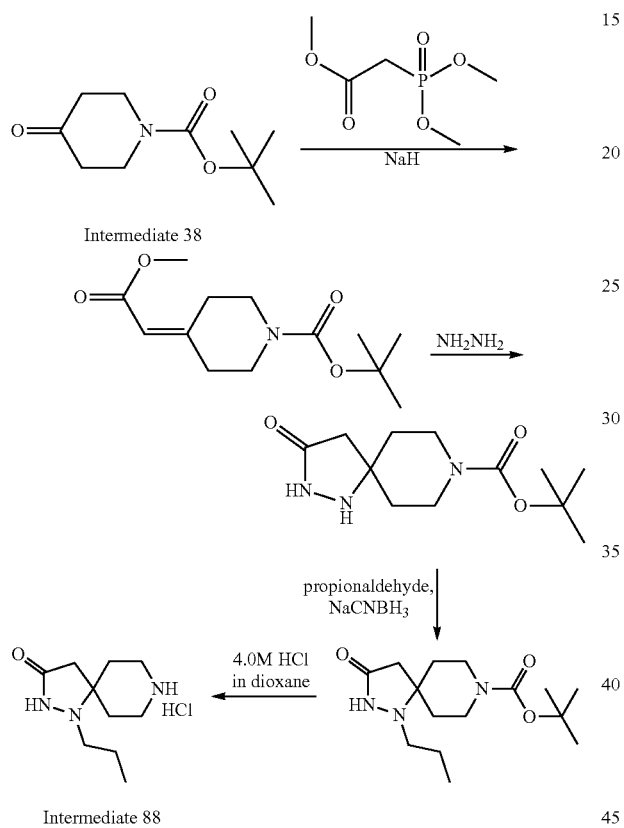

Intermediate 88

Sodium hydride in mineral oil (60%, 11.9 g, 297 mmol) was dissolved in DMF (200 mL) and methyl 2-(dimethoxyphosphoryl)acetate (52.0 g, 286 mmol) was added drop wise at 0° C. The reaction mixture was stirred at 0° C. for 20 min then tert-butyl 4-oxopiperidine-1-carboxylate (45.5 g, 228 mmol) in DMF (100 mL) was added drop wise at 0° C. The reaction mixture was stirred at rt for 2 h, then diluted with ice water (20 mL), filtered and the solvents were removed in vacuo to give tert-butyl 4-(2-methoxy-2-oxoethylidene)piperidine-1-carboxylate (42.5 g, 72.9%) as a yellow solid.

LCMS (Method F): m/z 256 (M+H)$^+$ (ES$^+$), at 2.47 min, UV active tert-Butyl 4-(2-methoxy-2-oxoethylidene)piperidine-1-carboxylate (3.0 g, 11.8 mmol) was dissolved in EtOH (20 mL) and hydrazine hydrate (1.1 mL, 23.5 mmol) was added and the reaction mixture was stirred at 80° C. for 8 h. The reaction mixture was partitioned between water (150 mL) and EtOAc (120 mL), aqueous layer was further extracted with EtOAc (2×120 mL), organic layers were combined washed with brine (100 mL) and dried (Na$_2$SO$_4$). The solvents were removed in vacuo and the residue was purified by column chromatography (normal silica, mesh size: 60-120, 4.0% to 10.0% MeOH in DCM) to give tert-butyl 3-oxo-1, 2, 8-triazaspiro[4.5]decane-8-carboxylate (1.78 g, 59.3%) as white solid.

LCMS (Method F): m/z 256 (M+H)$^+$ (ES$^+$), at 1.70 min, UV inactive tert-Butyl 3-oxo-1,2,8-triazaspiro[4.5]decane-8-carboxylate (500 mg, 1.96 mmol), was dissolved in MeOH (10 mL). Propionaldehyde (0.2 mL, 2.16 mmol) and triethylamine (0.8 mL, 5.88 mmol) were added, the reaction mixture was stirred at 45° C. for 3 h. NaCNBH$_3$ (370 mg, 5.88 mmol) was added portion wise and the reaction mixture was stirred at rt for 17 h. The solvents were removed in vacuo and the residue was partitioned between H$_2$O (100 mL) and EtOAc (80 mL), aqueous layer was extracted with EtOAc (2×80 mL), the organic layers were combined, washed with brine (100 mL) and dried (Na$_2$SO$_4$). The solvents were removed in vacuo and the residue was purified by triturating with Hexane (3×3 mL) to give tert-butyl 1-propyl-3-oxo-1,2,8-triazaspiro[4.5]decane-8-carboxylate (560 mg, 96.2%) as a yellow gum.

LCMS (Method E): m/z 298 (M+H)$^+$ (ES$^+$), at 3.72 min, UV inactive tert-Butyl 1-propyl-3-oxo-1,2,8-triazaspiro[4.5]decane-8-carboxylate (610 mg, 2.05 mmol) was dissolved in 1,4-dioxane (3 mL) and 4.0M HCl in dioxane (5 mL) was added drop wise, the reaction mixture was stirred at 25° C. for 16 h. The solvents were removed in vacuo and the residue was purified by triturating with Et$_2$O (3×3 mL) to give 1-propyl-1,2,8-triazaspiro[4.5]decan-3-one. HCl, Intermediate 88 (470 mg, 98.3%) as an off white solid.

The data for the title compound are in Table 2

General Synthetic Procedures:

Route a

Typical Procedure for the Preparation of Piperidines Via NaCNBH$_3$ Reductive Amination as Exemplified by the Preparation of Example 2-2, ethyl 3-(3-oxo-2,8-diazaspiro[4.5]dec-8-yl)-8-azabicyclo[3.2.1]octane-8-carboxylate

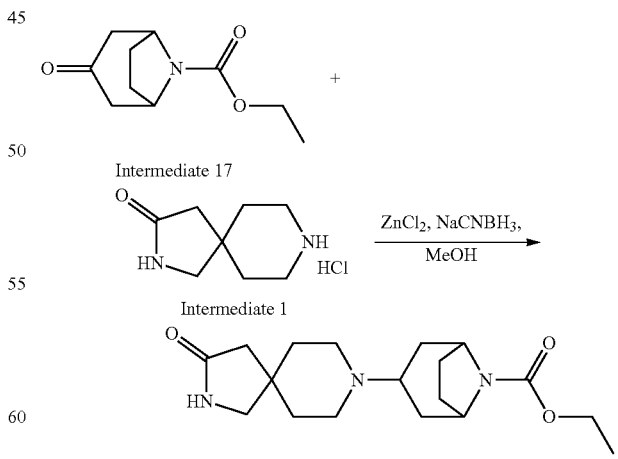

Example 2-2

2,8-Diazaspiro[4.5]decan-3-one.HCl (0.40 g, 1.78 mmol) was dissolved in MeOH (3 mL) and treated with K$_2$CO$_3$ (0.49 g, 3.55 mmol) in a minimum of water to de-salt. The mixture was concentrated in vacuo. The residue and ethyl 3-oxo-8-azabicyclo[3.2.1]octane-8-carboxylate (0.35 g, 1.78 mmol) were dissolved in MeOH (8 mL) and zinc chloride (0.73 g, 5.33 mmol) was added. The reaction mixture was stirred at 50° C., under a nitrogen atmosphere, for 2 h then cooled to rt and NaCNBH₃ (0.23 g, 3.55 mmol) was added. The reaction mixture was stirred at 50° C. under nitrogen for 16 h. The reaction mixture was cooled to rt and treated with sat. NaHCO₃ sol., the organic solvent was removed in vacuo and the aqueous layer was extracted with DCM (2×10 mL) the organic layers were combined and washed with brine (10 mL) and dried by passing through a Biotage Phase Separator cartridge. The solvents were removed in vacuo, and the residue was purified by column chromatography (normal phase, [Interchim cartridge Puriflash column 15 silica HP-silica 15µ 40 G, 30 mL per min, gradient 0% to 10% MeOH in DCM]) to give ethyl 3-(3-oxo-2,8-diazaspiro[4.5]dec-8-yl)-8-azabicyclo[3.2.1]octane-8-carboxylate Example 2-2 Isomer 1 (16 mg, 2.5%) as an off-white solid and ethyl 3-(3-oxo-2,8-diazaspiro[4.5]dec-8-yl)-8-azabicyclo[3.2.1]octane-8-carboxylate Example 2-2 Isomer 2 (10 mg, 1.7%) as an off-white solid.

The data for Isomers 1 and 2 are in Table 3.

Route b

Typical Procedure for the Preparation of Piperidines via NaCNBH₃ Reductive Amination as Exemplified by the Preparation of Example 2-8, ethyl 3-(1-ethyl-3-oxo-2,8-diazaspiro[4.5]decan-8-yl)-8-azabicyclo[3.2.1]octane-8-carboxylate

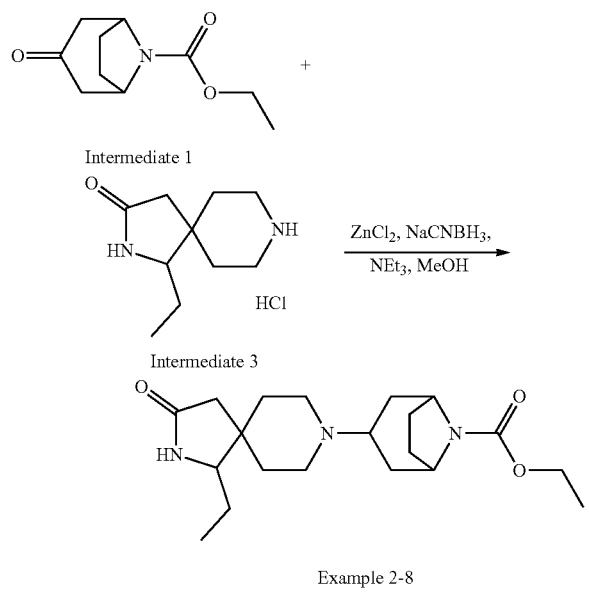

1-Ethyl-2,8-diazaspiro[4.5]decan-3-one.HCl (0.1 g, 0.55 mmol), ethyl 3-oxo-8-azabicyclo[3.2.1]octane-8-carboxylate (0.2 g, 0.60 mmol), Et₃N (0.38 mL, 2.74 mmol) and ZnCl₂ (0.04 g, 0.03 mmol) were dissolved in MeOH (5 mL) under N₂ and stirred at 60° C. for 16 h. Reaction mixture cooled to 0° C. and NaCNBH₃ (0.17 g, 2.74 mmol) was added portion wise, the reaction mixture was stirred under N₂ at 60° C. for 16 h. The solvents were removed in vacuo and the residue was partitioned between water (50 mL) and EtOAc (30 mL), the aqueous layer was further extracted with EtOAc (2×30 mL); the organic layers were combined and washed with brine, then dried (Na₂SO₄).

The solvents were removed in vacuo and the residue was purified by preparative reversed phase HPLC (Durashell, 250×21.2 mm, 5 um, 13 mL per min, gradient 30% to 100% (over 28 min), then 100% (3 min) Acetonitrile in 50% Acetonitrile/water (0.1% Ammonia)) to give ethyl 3-(1-ethyl-3-oxo-2,8-diazaspiro[4.5]decan-8-yl)-8-azabicyclo[3.2.1]octane-8-carboxylate Example 2-8 Isomer 1 (0.03 g, 15.1%) as a colourless solid and ethyl 3-(1-ethyl-3-oxo-2, 8-diazaspiro[4.5]decan-8-yl)-8-azabicyclo[3.2.1]octane-8-carboxylate Example 2-8 Isomer 2 (0.006 g, 3.1%) as a colourless solid.

The data for both isomers are in Table 3.

Route c

Typical Procedure for the Preparation of Piperidines Via Sodium Triacetoxyborohydride Reductive Amination in DMF as Exemplified by the Preparation of Example 3-2, ethyl 5-(2-oxo-1-oxa-3,8-diazaspiro[4.5]dec-8-yl)-2-azabicyclo[2.2.2]octane-2-carboxylate

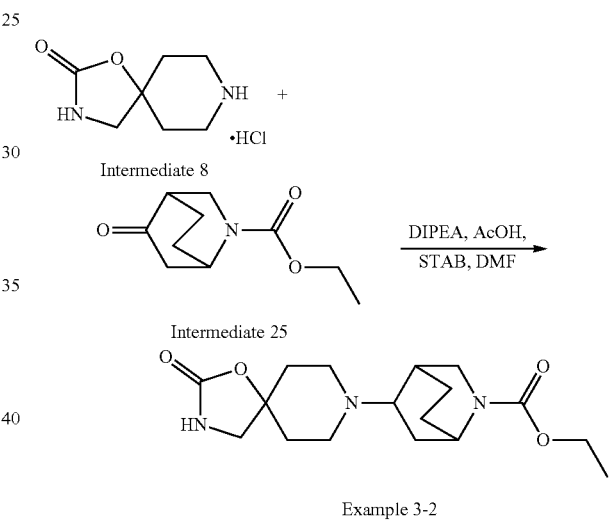

1-Oxa-3,8-diazaspiro[4.5]decan-2-one hydrochloride (0.10 g, 0.52 mmol) and ethyl 5-oxo-2-azabicyclo[2.2.2]octane-2-carboxylate (0.10 g, 0.51 mmol) were mixed in DMF (5 mL) at rt. DIPEA (0.18 mL, 1.0 mmol) and AcOH (0.044 mL, 0.77 mmol) were added, followed by STAB (0.32 g, 1.5 mmol). The reaction mixture was stirred under nitrogen at 45° C. for 3 d and at 60° C. for 1 d, the solvents were removed in vacuo. The residue was purified by column chromatography (normal phase, [Biotage SNAP cartridge KP-sil 25 g, 40-63 µm, 60 Å, 30 mL per min, gradient 0% to 10% Solvent A in DCM over 10 column volumes, then isocratic 10% Solvent A in DCM for 5 column volumes, where solvent A is 10% of (7 M NH₃/MeOH) in MeOH]) to give a mixture of diastereomers. This mixture was purified by preparative reversed phase HPLC (Phenomenex Gemini-NX 5 µm C18 110A Axia column, 100×30 mm, eluted with 15 to 55% MeCN/Solvent B over 14.4 min at 30 mL/min [where solvent B is 0.2% of (28% NH₃/H₂O) in H₂O] and collecting fractions by monitoring at 205 nm) to give ethyl 5-(2-oxo-1-oxa-3,8-diazaspiro[4.5]dec-8-yl)-2-azabicyclo[2.2.2]octane-2-carboxylate Example 3-2 Isomer 1 (0.074 g, 43%) as a colourless solid and ethyl 5-(2-oxo-1-oxa-3,8- diazaspiro[4.5]dec-8-yl)-2-azabicyclo[2.2.2]octane-2-carboxylate Example 3-2 Isomer 2 (0.023 g, 13%) as a colourless solid.

The data for Isomers 1 and 2 are in Table 3.

Route d

Typical Procedure for the Preparation of Piperidines Via Sodium Triacetoxyborohydride Reductive Amination as Exemplified by the Preparation of Example 5-2, prop-2-yn-1-yl 3-(3-oxo-2,8-diazaspiro[4.5]dec-8-yl)-9-azabicyclo[3.3.1]nonane-9-carboxylate

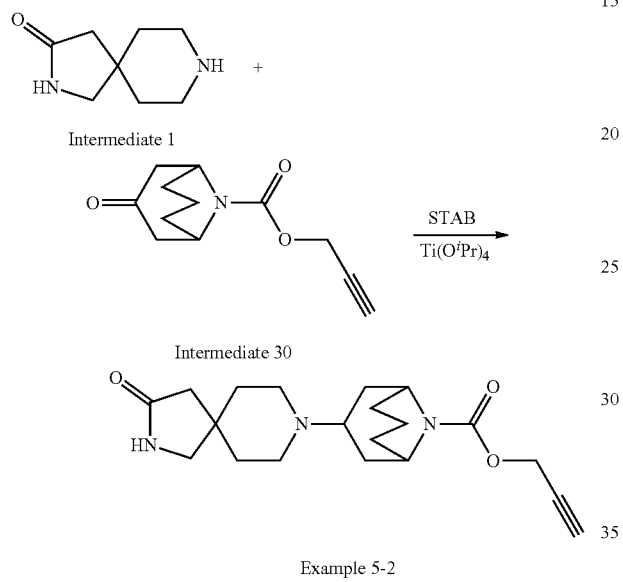

Route e

Typical Procedure for the Preparation of Piperidines Via Sodium Triacetoxyborohydride Reductive Amination, Boc-Deprotection and Ethylcarbamate Formation as Exemplified by the Preparation of Example 5-1, ethyl 3-(3-oxo-2,8-diazaspiro[4.5]dec-8-yl)-9-azabicyclo[3.3.1]nonane-9-carboxylate

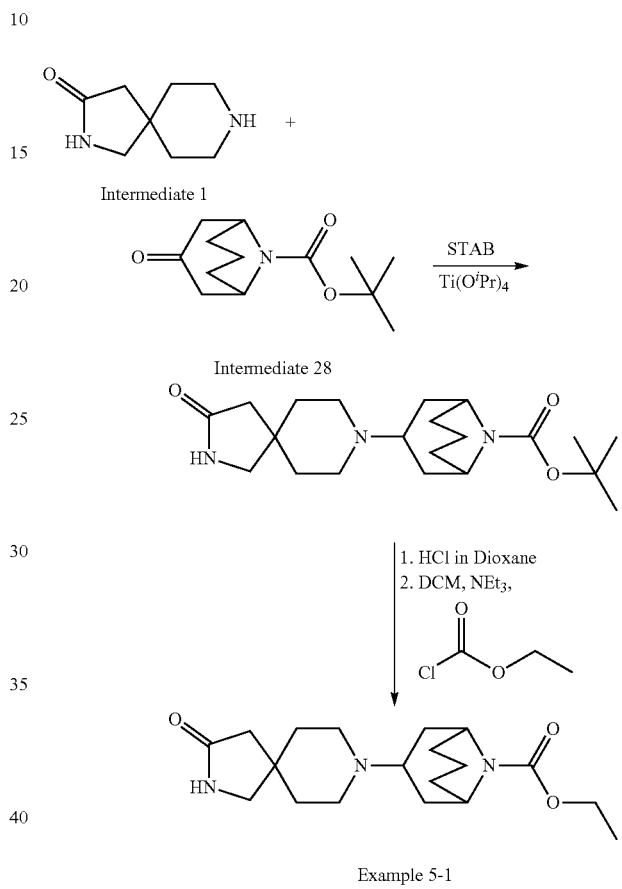

2,8-Diazaspiro[4.5]decan-3-one (0.12 g, 0.75 mmol) and prop-2-yn-1-yl 3-oxo-9-azabicyclo[3.3.1]nonane-9-carboxylate (0.17 g, 0.75 mmol) were dissolved in DCE (7.5 mL) at rt and titanium isopropoxide (0.66 mL, 2.25 mmol) was added. The reaction mixture was heated to reflux under $N_2$ for 16 h then cooled to rt. STAB (0.80 g, 3.75 mmol) was added, the reaction mixture again heated to reflux for 16 h then cooled to rt. The reaction mixture was quenched with the addition of sat. $NaHCO_3$ sol. (10 mL), diluted with DCM (10 mL) then filtered through a pad of celite. The layers were separated and the aqueous layer was extracted with DCM (4×20 mL). The organic layers were combined and washed with brine, then dried ($MgSO_4$). The solvents were removed in vacuo, and the residue was purified by column chromatography (normal phase, [Biotage SNAP cartridge KP-sil 25 g, 40-63 μm, 60 Å, 27 mL per min, gradient 1% to 10% MeOH in DCM]) to give an inseparable mixture of diastereomers This mixture was purified by preparative reversed phase HPLC (Phenomenex Gemini-NX 5 μm C18 110A Axia column, 100×30 mm, eluting with 15 to 35% MeCN/Solvent B over 14.4 min at 30 mL/min [where solvent B is 0.2% of (28% $NH_3/H_2O$) in $H_2O$] and collecting fractions by monitoring at 205 nm) to give prop-2-yn-1-yl 3-(3-oxo-2,8-diazaspiro[4.5]dec-8-yl)-9-azabicyclo[3.3.1]nonane-9-carboxylate Example 5-2 Isomer (0.02 g, 7%) as a colourless solid and prop-2-yn-1-yl 3-(3-oxo-2,8-diazaspiro[4.5]dec-8-yl)-9-azabicyclo[3.3.1]nonane-9-carboxylate Example 5-2 Isomer 2 (0.03 g, 11%) as a colourless solid.

The data for both isomers are in Table 3.

2,8-Diazaspiro[4.5]decan-3-one (0.15 g, 1.0 mmol) and tert-butyl 3-oxo-9-azabicyclo[3.3.1]nonane-9-carboxylate (0.25 g, 0.1.05 mmol) were dissolved in DCE (10.0 mL) at rt and titanium isopropoxide (0.89 mL, 3.0 mmol) was added. The reaction mixture was stirred overnight at reflux under $N_2$, then cooled to room temperature. STAB (1.06 g, 5.0 mmol) was added, the reaction mixture again heated to reflux, maintained overnight and then cooled to room temperature. The reaction mixture was quenched with the addition of sat. $NaHCO_3$ sol. (10 mL), diluted with DCM (10 mL) then filtered through a pad of celite. The layers were separated and the aqueous layer was extracted with DCM (4×20 mL). The organic layers were combined and washed with brine, then dried ($MgSO_4$). The solvents were removed in vacuo to give crude tea-butyl 3-(3-oxo-2,8-diazaspiro [4.5]dec-8-yl)-9-azabicyclo[3.3.1]nonane-9-carboxylate which was used without any purification.

LCMS (Method C): m/z 378 (M+H)$^+$ (ES$^+$), at 1.54 min, UV active.

tert-Butyl 3-(3-oxo-2,8-diazaspiro[4.5]dec-8-yl)-9-azabicyclo[3.3.1]nonane-9-carboxylate (0.38 g, 1.0 mmol assumed) was dissolved in DCM (10 mL), 4.0 M HCl in 1,4-dioxane (1.25 mL, 5.0 mmol) was added and the reaction mixture stirred at rt for 18 h. The volatiles were removed in vacuo, the residue dissolved in DCM (10 mL), Et₃N (0.70 mL, 5.0 mmol) and ethyl chloroformate (143 µL, 1.50 mmol) added dropwise and the solution stirred at rt for 18 h. The mixture was then poured into sat. NaHCO₃ sol. (20 mL), extracted with DCM (4×20 mL), the organic layers were combined and washed with brine, then dried (MgSO₄). The solvents were removed in vacuo and the residue was purified by column chromatography (normal phase, [Biotage SNAP cartridge KP-sil 25 g, 40-63 µm, 60 Å, 27 mL per min, gradient 1% to 10% MeOH in DCM]) to give an inseparable mixture of diastereomers. This mixture was purified by preparative reversed phase HPLC (Phenomenex Gemini-NX 5 µm C18 110A Axia column, 100×30 mm, eluting with 20 to 30% MeCN/Solvent B over 14.4 min at 30 mL/min [where solvent B is 0.2% of (28% NH₃/H₂O) in H₂O] and collecting fractions by monitoring at 205 nm) to give ethyl 3-(3-oxo-2,8-diazaspiro[4.5]dec-8-yl)-9-azabicyclo[3.3.1]nonane-9-carboxylate Example 5-1 Isomer 1 (0.02 g, 6%) as a colourless solid and ethyl 3-(3-oxo-2,8-diazaspiro[4.5]dec-8-yl)-9-azabicyclo[3.3.1]nonane-9-carboxylate Example 5-1 Isomer 2 (0.01 g, 3%) as a colourless solid.

The data for both isomers are in Table 3.

Route f

Typical Procedure for the Preparation of Piperidines Via NaCNBH₃ Reductive Amination, Boc-Deprotection and Ethylcarbamate Formation as Exemplified by the Preparation of Example 7-1, ethyl 6-(2-oxo-1-oxa-3,8-diazaspiro[4.5]dec-8-yl)-3-azabicyclo[3.2.1]octane-3-carboxylate

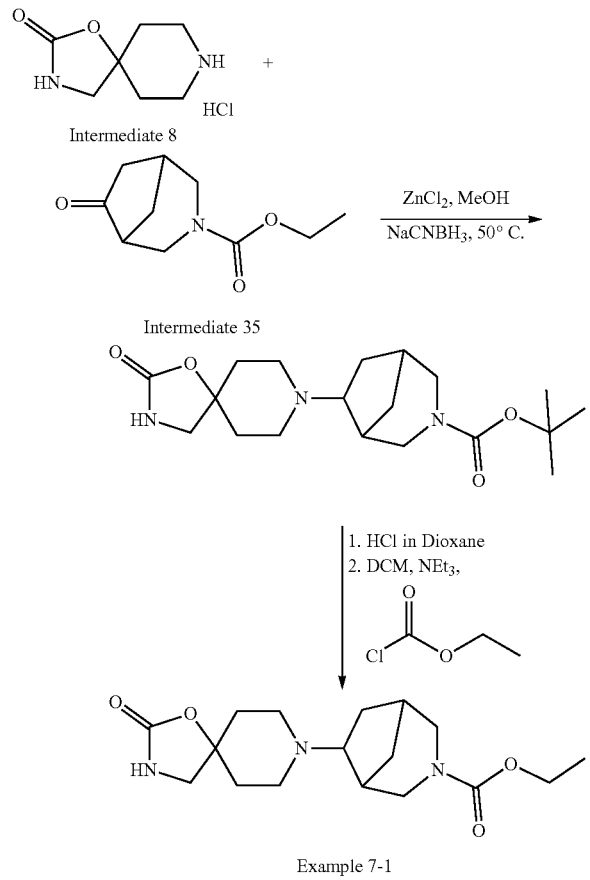

Example 7-1

1-Oxa-3,8-diazaspiro[4.5]decan-2-one. HCl (0.15 g, 0.76 mmol) was dissolved in MeOH (3 mL) and treated with K₂CO₃ (0.11 g, 0.76 mmol) in a minimum of water to de-salt. The solvents were removed in vacuo and the residue was dissolved in MeOH (8 mL) and ethyl-6-oxo-3-azabicyclo[3.2.1]octane-3-carboxylate (0.15 g, 0.76 mmol) and ZnCl₂ (0.31 g, 2.28 mmol) were added. The reaction mixture was stirred at 50° C. under a N₂ for 2 h then cooled to rt and NaCNBH₃ (0.10 g, 1.52 mmol) was added. The reaction mixture was stirred at 50° C. under a N₂ for 16 h then cooled to rt and quenched with sat. NaHCO₃ sol. (10 mL). The solvents were removed in vacuo and the aqueous layer was washed with DCM (2×10 mL) the organic layers were combined and washed with brine, then dried by passing through a Biotage Phase Separator cartridge. The solvents were removed in vacuo and the residue was purified by column chromatography (normal phase, [Biotage SNAP cartridge KP-sil 10 g, 40-63 µm, 60 Å, 12 mL per min, gradient 0% to 10% MeOH in DCM]) to tert-butyl 6-(2-oxo-1-oxa-3,8-diazaspiro[4.5]dec-8-yl)-3-azabicyclo[3.2.1]octane-3-carboxylate (6.0 mg, 2.2%) as a colourless gum LCMS (Method D): m/z 366 (M+H)⁺ (ES⁺), at 1.76 min, UV inactive.

tert-Butyl 6-(2-oxo-1-oxa-3,8-diazaspiro[4.5]dec-8-yl)-3-azabicyclo[3.2.1]octane-3-carboxylate (6.0 mg, 0.016 mmol) was diluted in 4.0 M HCl in 1,4-dioxane (3 mL) and stirred at rt under a N₂ for 16 h. The solvents were removed in vacuo and the residue was dissolved in DCM (4 mL) and cooled to 0° C. under N₂, Et₃N (5 mg, 0.048 mmol) and ethyl chloroformate (4 mg, 0.032 mmol) were added and the reaction mixture was stirred at rt under N₂ for 16 h. The reaction mixture was diluted with DCM (10 mL) and washed with sat. NaHCO₃ sol. (20 mL), the aqueous layer was extracted with DCM (2×15 mL), the organic layers were combined and washed with brine, then dried by passing through a Biotage phase separator cartridge. The solvents were removed in vacuo and the residue was purified by preparative reversed phase HPLC (Phenomenex Gemini-NX 5 µm C18 110 A Axia column, 100×30 mm, eluting with 20 to 50% MeCN/Solvent B over 14.4 min at 30 mL/min [where solvent B is 0.2% of (28% NH₃/H₂O) in H₂O] and collecting fractions by monitoring at 205 nm) to give ethyl 6-(2-oxo-1-oxa-3,8-diazaspiro[4.5]dec-8-yl)-3-azabicyclo[3.2.1]octane-3-carboxylate Example 7-1 Isomer 1 (0.84 mg, 15%) as a colourless gum.

The data for this compound are in Table 3.

Route g

Typical Procedure for the Preparation of Piperidines Via NaCNBH₃ Reductive Amination as Exemplified by the Preparation of Example 2-23, ethyl 3-(2-oxo-4-(pyridin-2-ylmethyl)-1-oxa-3,8-diazaspiro[4.5]decan-8-yl)-8-azabicyclo[3.2.1]octane-8-carboxylate

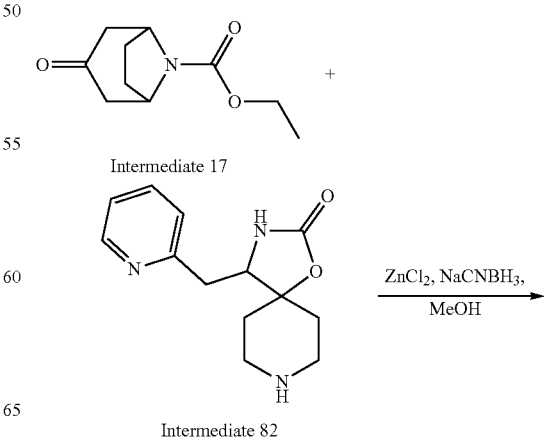

Intermediate 82

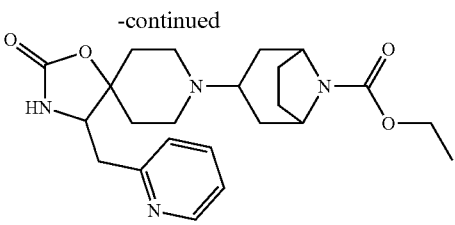

Example 2-23

To a solution of 4-(pyridin-2-ylmethyl)-1-oxa-3,8-diazaspiro[4.5]decan-2-one (0.10 g, 0.41 mmol) and ethyl 3-oxo-8-azabicyclo[3.2.1]octane-8-carboxylate (0.80 g, 0.41 mmol) in MeOH (5 mL), $ZnCl_2$ (0.17 g, 1.21 mmol) was added. The reaction mixture was stirred at 60° C., under a $N_2$ atmosphere, for 6 h then cooled to rt and $NaCNBH_3$ (0.08 g, 1.21 mmol) was added. The reaction mixture was stirred at 60° C. under nitrogen for 16 h. The reaction mixture was cooled to rt, the solvent was removed in vacuo and the residue partitioned between sat. $NaHCO_3$ sol. (10 mL) and DCM (10 mL), the aqueous layer was further washed with DCM (2×10 mL). The organic layers were combined and washed with brine, dried ($Na_2SO_4$) and the solvents were removed in vacuo. The residue was purified by column chromatography (normal phase, silica gel (100-200 mesh), gradient 2% to 5% MeOH in DCM] to give ethyl-3-(2-oxo-4-(pyridin-2-ylmethyl)-1-oxa-3,8-diazaspiro [4.5]decan-8-yl)-8-azabicyclo[3.2.1]octane-8-carboxylate as a mixture of diastereomers, Example 2-23 (32 mg, 20%) as a white solid.

The data for example 2-23 is in Table 3.

Route h

Procedure for the Preparation of Example 2-24, ethyl (3-endo)-3-(2-hydroxy-3-oxo-2,8-diazaspiro [4.5]dec-8-yl)-8-azabicyclo[3.2.1]octane-8-carboxylate

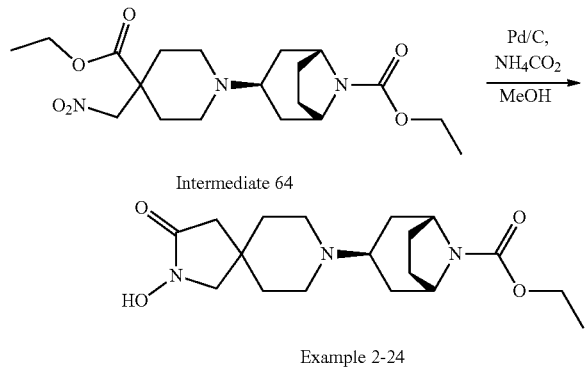

Example 2-24

A solution of ethyl (3-endo)-3-[4-(2-ethoxy-2-oxoethyl)-4-(nitromethyl)piperidin-1-yl]-8-azabicyclo[3.2.1]octane-8-carboxylate (2.00 g, 4.87 mmol) in anhydrous MeOH (30 mL) was divided equally between 4×20 mL microwave vials. The solutions were degassed with nitrogen and then 10% palladium on carbon (0.13 mg, 1.21 mmol) and ammonium formate (1.54 g, 24.20 mmol) were added. The vials were sealed and stirred at rt for 4 h. The four reaction mixtures were combined and filtered through a celite pad under nitrogen, and the solvents were removed in vacuo. The residue was purified by preparative reversed phase HPLC [Gemini-NX C18, 5μ, 100×30 mm, 30 mL per min, 5-35% MeCN/Water+0.2% Ammonia (28% Ammonia Solution) to give Example 2-24, 8-[8-(ethoxycarbonyl)-8-azabicyclo [3.2.1]oct-3-yl]-3-oxo-2,8-diazaspiro[4.5]decan-2-olate (0.90 g, 52.5%) as a white solid.

The data for the title compound is in Table 3.

Route i

Typical Procedure for the Preparation of Piperidines Via N-Alkylation as Exemplified by the Preparation of Example 2-25, ethyl 3-(3-oxo-2-propyl-2,8-diazaspiro[4.5]dec-8-yl)-8-azabicyclo [3.2.1]octane-8-carboxylate

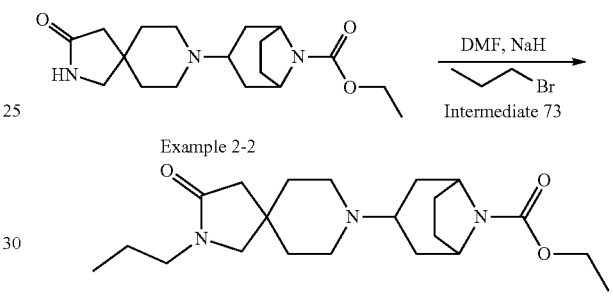

Example 2-25

Ethyl 3-(3-oxo-2,8-diazaspiro[4.5]dec-8-yl)-8-azabicyclo [3.2.1]octane-8-carboxylate (0.20 g, 0.59 mmol) was dissolved in DMF (5.0 mL). NaH (60%) (0.071 g, 1.78 mmol) was added at 0° C. and the reaction mixture stirred at 0° C. for 30 min. 1-Bromopropane (0.11 g, 0.89 mmol) was added and the reaction mixture stirred at rt for 1 h. The reaction mixture was quenched with the addition of water (20 mL) and extracted with EtOAc (150 mL), the aqueous layer was further extracted with EtOAc (2×15 mL); the organic layers were combined and washed with brine, then dried ($Na_2SO_4$). The solvents were removed in vacuo, and the residue was purified by preparative reversed phase HPLC [X-Bridge, 150×19 mm, 5 μm, 12 mL per min, isocratic 29% (for 20 min), then 100% (4 min) MeCN in 50% MeCN/water (0.1%, Ammonia)] to give ethyl 3-(3-oxo-2-propyl-2,8-diazaspiro [4.5]dec-8-yl)-8-azabicyclo[3.2.1]octane-8-carboxylate, Example 2-25 (14.5 mg, 6.5%) as a colourless solid.

The data for the title compound are in Table 3.

Route j

Typical Procedure for the Preparation of Piperidines Via Carbamate Formation, as Exemplified by the Preparation of Example 2-30, (1,1-$^2H_2$)ethyl 3-(3-oxo-2,8-diazaspiro[4.5]dec-8-yl)-8-azabicyclo [3.2.1]octane-8-carboxylate

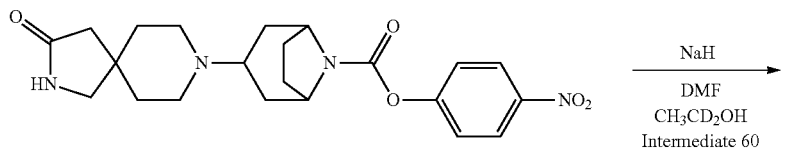

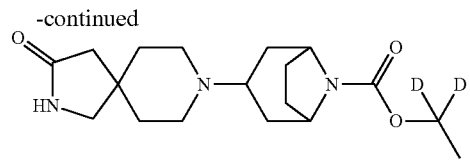

Example 2-30

4-Nitrophenyl 3-(3-oxo-2,8-diazaspiro[4.5]dec-8-yl)-8-azabicyclo[3.2.1]octane-8-carboxylate (100 mg, 0.24 mmol) was dissolved in anhydrous DMF (3 mL) and 60% sodium hydride suspension in mineral oil (47 mg, 1.18 mmol) was added. The reaction mixture was stirred at rt under nitrogen for 10 min. Ethanol-1,1-$d_2$ (57 mg, 1.18 mmol) was added and the reaction mixture was stirred overnight at rt under nitrogen. Water (1 mL) was added to the reaction mixture and the solvents were removed in vacuo. The residue was partitioned between DCM (10 mL) and sat. aqueous NaHCO$_3$ (10 mL), the aqueous layer was extracted with DCM (2×10 mL). The combined organics were dried by passing through a Biotage Phase Separator cartridge and the solvents were removed in vacuo. The residue was purified by column chromatography (normal phase, [Biotage SNAP cartridge KP-sil 10 g, 40-63 μm, 60 Å, 12 mL per min, gradient 0% to 10% MeOH in DCM]) to give (1,1-$^2$H$_2$)ethyl 3-(3-oxo-2,8-diazaspiro[4.5]dec-8-yl)-8-azabicyclo[3.2.1]octane-8-carboxylate, Example 2-30 Isomer 1 (11 mg, 14%) as a pale yellow gum and (1,1-$^2$H$_2$)ethyl 3-(3-oxo-2,8-diazaspiro[4.5]dec-8-yl)-8-azabicyclo[3.2.1]octane-8-carboxylate, Example 2-30 Isomer 2 (18 mg, 23%) as a pale yellow gum.

The data for both isomers are in Table 3.

Route k

Typical Procedure for the Preparation of Piperidines Via Sodium Triacetoxyborohydride Reductive Amination in DMF as Exemplified by the Preparation of Example 3-1, ethyl 5-(3-oxo-2,8-diazaspiro[4.5]dec-8-yl)-2-azabicyclo[2.2.2]octane-2-carboxylate

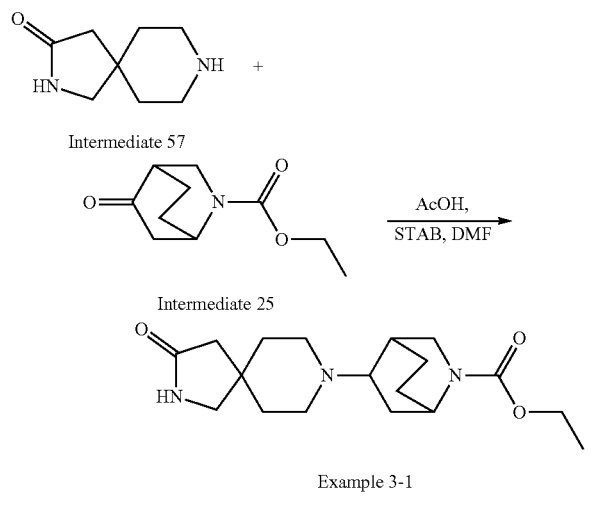

To a solution of ethyl 5-oxo-2-azabicyclo[2.2.2]octane-2-carboxylate (6.70 g, 34 mmol) and 2,8-diazaspiro[4.5]decan-3-one1 (5.24 g, 34 mmol) in DMF (30 mL) was added HOAc (2.9 mL, 51 mmol) under nitrogen, the reaction mixture was stirred at rt for 20 min. Na(OAc)$_3$BH (21.60 g, 102 mmol) was added and the reaction was stirred at 45° C. for 3 d. Then the reaction mixture was warmed to 60° C. and stirred for another 24 h. The solvent was removed in vacuo and the residue was dissolved in water (20 mL) and basified with sat. NaHCO$_3$. The aqueous layer was concentrated to dryness and the resulting white solid was diluted with DCM (100 mL). The suspension was stirred at rt for 30 min, filtered and the filter cake was washed with DCM (4×25 mL). The organic layers were combined and the solvent was removed in vacuo. The residue was purified by preparative reversed phase HPLC (Instrument: Gilson, Column: Xbridge 21.2*250 mm C18, 10 um; Mobile Phase: A: water (10 mMol/L NH$_4$HCO$_3$) B: CAN); Flow rate (ml/min): 25.00) to give the two racemic isomers of ethyl 5-(3-oxo-2,8-diazaspiro[4.5]dec-8-yl)-2-azabicyclo[2.2.2]octane-2-carboxylate. Which were further purified by chiral SFC (Column: OJ-H, 4.6*250 mm; Co-solvent: MeOH (0.1% NH$_4$OH); column temperature: 40; CO$_2$ flow rate: 2.55) to give ethyl 5-(3-oxo-2,8-diazaspiro[4.5]dec-8-yl)-2-azabicyclo[2.2.2]octane-2-carboxylate, Example 3-1 Isomer 1 (0.78 g, 6.9%) as a colourless solid, ethyl 5-(3-oxo-2,8-diazaspiro[4.5]dec-8-yl)-2-azabicyclo[2.2.2]octane-2-carboxylate, Example 3-1 Isomer 2 (1.20 g, 10.5%) as a colourless solid, ethyl 5-(3-oxo-2,8-diazaspiro[2.2.2]octane-2-carboxylate, Example 3-1 Isomer 3 (0.45 g, 3.9%) as a colourless solid and ethyl 5-(3-oxo-2,8-diazaspiro[4.5]dec-8-yl)-2-azabicyclo[2.2.2]octane-2-carboxylate, Example 3-1 Isomer 4 (1.30 g, 11.4%) as a colourless solid.

The data for all four isomers are in Table 3.

Route l

Typical Procedure for the Preparation of Piperidines Via NaCNBH$_3$ Reductive Amination as Exemplified by the Preparation of Example 3-3, ethyl 5-(4-ethyl-2-oxo-1-oxa-3,8-diazaspiro[4.5]dec-8-yl)-2-azabicyclo[2.2.2]octane-2-carboxylate

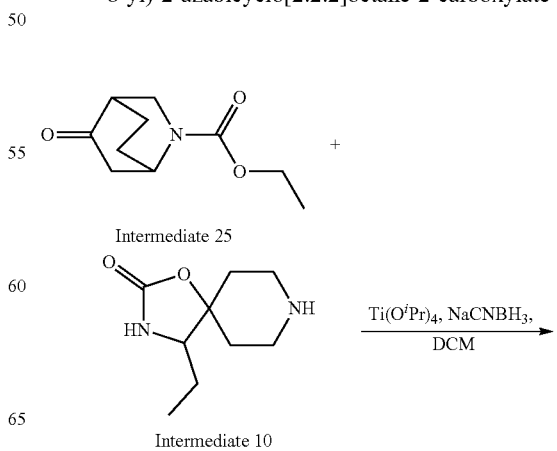

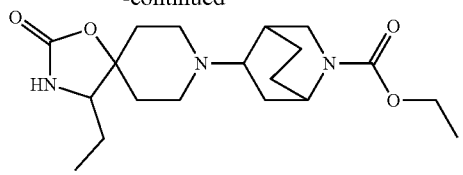

Example 3-3

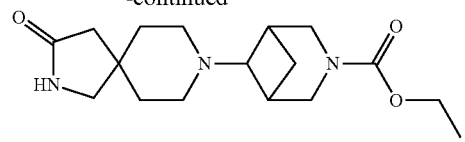

Example 8-1

Ethyl 5-oxo-2-azabicyclo[2.2.2]octane-2-carboxylate (0.077 g, 0.39 mmol) and 4-ethyl-1-oxa-3,8-diazaspiro[4.5]decan-2-one (0.070 g, 0.39 mmol) were dissolved in DCM (3.9 mL). Titanium (IV) isopropoxide (0.35 mL, 1.17 mmol) was added and the reaction mixture was stirred at rt under nitrogen for 3 h. NaCNBH$_3$ (0.049 g, 0.78 mmol) was added and the mixture stirred at rt under nitrogen overnight. The reaction mixture was partitioned between water (10 mL) and DCM (10 mL) and the solution was passed through a celite pad to remove solids. The filtrate layers were separated and the aqueous phase was extracted with DCM (3×25 mL). The organic phases were combined and washed with sat. NaHCO$_3$ sol. (25 mL) and dried by passing through a Biotage Phase Separator cartridge. The solvents were removed in vacuo, and the residue was purified by column chromatography (normal phase, [Biotage SNAP cartridge KP-sil 10 g, 40-63 µm, 60 Å, 10 mL per min, gradient 0% to 10% MeOH in DCM]) to give a mixture of diastereomers of ethyl 5-(4-ethyl-2-oxo-1-oxa-3,8-diazaspiro[4.5]dec-8-yl)-2-azabicyclo[2.2.2]octane-2-carboxylate. This mixture of diastereomers was further purified by preparative reversed phase HPLC (Phenomenex Gemini-NX 5 µm C18 110A Axia column, 100×30 mm, eluting with 20 to 50% MeCN/Solvent B over 12.5 min at 30 mL/min [where solvent B is 0.2% of (28% NH$_3$/H$_2$O) in H$_2$O] and collecting fractions by monitoring at 205 nm) to give ethyl 5-(4-ethyl-2-oxo-1-oxa-3,8-diazaspiro[4.5]dec-8-yl)-2-azabicyclo[2.2.2]octane-2-carboxylate, Example 3-3 Isomer 1 (0.021 g, 14.8%) as a colourless solid and ethyl 5-(4-ethyl-2-oxo-1-oxa-3,8-diazaspiro[4.5]dec-8-yl)-2-azabicyclo[2.2.2]octane-2-carboxylate, Example 3-3 Isomer 2 (0.022 g, 15.5%) as a colourless solid.

The data for isomer 2 are in Table 2.

Route m

Typical Procedure for the Preparation of Piperidines Via NaBH$_4$ Reductive Amination as Exemplified by the Preparation of Example 8-1, ethyl 6-(3-oxo-2,8-diazaspiro[4.5]dec-8-yl)-3-azabicyclo[3.1.1]heptane-3-carboxylate

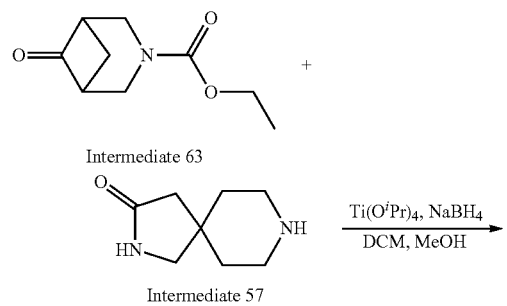

2,8-Diazaspiro[4.5]decan-3-one (0.11 g, 0.72 mmol) and ethyl 6-oxo-3-azabicyclo[3.1.1]heptane-3-carboxylate (0.12 g, 0.65 mmol) were dissolved in DCM (6.5 mL). Titanium (IV) isopropoxide (0.35 mL, 1.17 mmol) was added and the reaction mixture was stirred at rt under nitrogen overnight. The reaction mixture was cooled to −78° C. and MeOH (15 mL) was added, the reaction mixture was stirred for 15 min at −78° C. NaBH$_4$ (0.18 g, 5.20 mmol) was added and the reaction mixture was stirred at −78° C. for 1 h then at rt under nitrogen overnight. The reaction mixture was treated with NaOH (1 M, 10 mL) and stirred for 30 min. The precipitate was collected by filtration, washed with MeOH (3×20 mL) and the solvents were removed in vacuo. The residue was purified by column chromatography (normal phase, [Biotage SNAP cartridge KP-sil 25 g, 40-63 µm, 60 Å, 25 mL per min, gradient 0% to 10% MeOH in DCM]) to give a mixture of diastereomers of ethyl 6-(3-oxo-2,8-diazaspiro[4.5]dec-8-yl)-3-azabicyclo[3.1.1]heptane-3-carboxylate. The mixture of diastereomers was purified by preparative reversed phase HPLC (Phenomenex Gemini-NX 5 µm C18 110A Axia column, 100×30 mm, eluting with 15 to 50% MeCN/Solvent B over 12.5 min at 30 mL/min [where solvent B is 0.2% of (28% NH$_3$/H$_2$O) in H$_2$O] and collecting fractions by monitoring at 205 nm) to give ethyl 6-(3-oxo-2,8-diazaspiro[4.5]dec-8-yl)-3-azabicyclo[3.1.1]heptane-3-carboxylate, Example 8-1 Isomer 1 (0.006 g, 2.9%) as a colourless solid and ethyl 6-(3-oxo-2,8-diazaspiro[4.5]dec-8-yl)-3-azabicyclo[3.1.1]heptane-3-carboxylate, Example 8-1 Isomer 2 (0.040 g, 19.2%) as a colourless solid.

The data for the title compound are in Table 2

Route n

Typical Procedure for the Preparation of Azepanes Via NaCNBH$_3$ Reductive Amination as Exemplified by the Preparation of Example 9-1, ethyl 3-(3-oxo-2,8-diazaspiro[4.6]undec-8-yl)-8-azabicyclo[3.2.1]octane-8-carboxylate

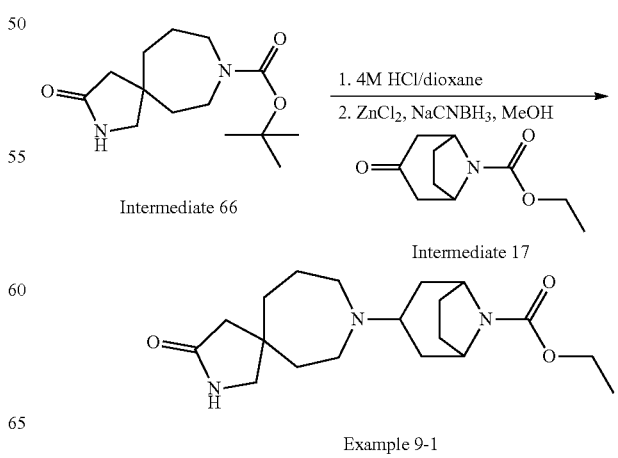

tert-Butyl 3-oxo-2,8-diazaspiro[4.6]undecane-8-carboxylate (0.398 g, 1.49 mmol) was added to 4.0 M HCl in 1,4-dioxane (8 mL) and stirred at rt under N₂ for 16 h. The solvents were removed in vacuo to give 2,8-diazaspiro[4.6]undecan-3-one hydrochloride (0.303 g, 100%) which was used without further purification. A portion of 2,8-diazaspiro[4.6]undecan-3-one hydrochloride (0.179 g, 0.74 mmol) was dissolved in MeOH (5 mL) and potassium carbonate (0.102 g, 0.74 mmol) dissolved in a minimum of water was added to desalt the amine. The solvents were removed in vacuo and the residue was dissolved in MeOH (8 mL) and ethyl 3-oxo-8-azabicyclo[3.2.1]octane-8-carboxylate (0.14 g, 0.74 mmol) and ZnCl₂ (0.30 g, 2.29 mmol) were added. The reaction mixture was stirred at 50° C. under N₂ for 2 h then cooled to rt and NaCNBH₃ (0.09 g, 1.49 mmol) was added. The reaction mixture was stirred at 50° C. under a N₂ for 16 h then cooled to rt and quenched with sat. NaHCO₃ sol. (10 mL). The methanol was removed in vacuo and the resulting solution was washed with DCM (2×10 mL) the organic layers were combined and washed with brine, then dried by passing through a Biotage Phase Separator cartridge. The solvents were removed in vacuo and the residue was purified by column chromatography (normal phase, [Biotage SNAP cartridge KP-sil 10 g, 40-63 µm, 60 Å, 1 2 mL per min, gradient 2% to 10% MeOH in DCM]) to give ethyl 3-(3-oxo-2,8-diazaspiro[4.6]undec-8-yl)-8-azabicyclo[3.2.1]octane-8-carboxylate, Example 9-1 Isomer 1 (0.034 g, 13.0%) as a yellow gum, and ethyl 3-(3-oxo-2,8-diazaspiro[4.6]undec-8-yl)-8-azabicyclo[3.2.1]octane-8-carboxylate Example 9-1 Isomer 2 (0.02 g, 0.9%) as a yellow gum.

The data for these compound are in Table 3.

Route o

Typical Procedure for the Preparation of Azepanes Via NaCNBH₃ Reductive Amination as Exemplified by the Preparation of Example 9-2, ethyl 3-(2-oxo-1-oxa-3,8-diazaspiro[4.6]undec-8-yl)-8-azabicyclo[3.2.1]octane-8-carboxylate

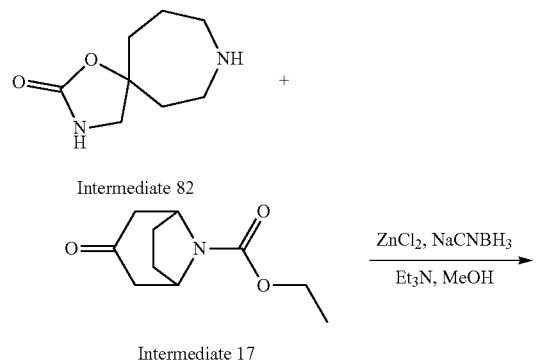

Intermediate 82

+

Intermediate 17

ZnCl₂, NaCNBH₃
———————————→
Et₃N, MeOH

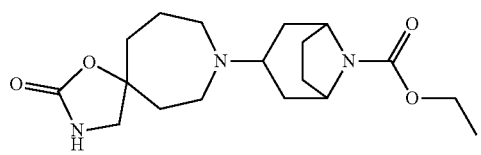

Example 9-2

1-Oxa-3,8-diazaspiro[4.6]undecan-2-one hydrochloride (5.3 g, 31.0 mmol), ethyl 3-oxo-8-azabicyclo[3.2.1]octane-8-carboxylate (6.1 g, 31.0 mmol), Et₃N (13.0 mL, 93.0 mmol), 4 Å molecular sieves (2.0 g) and ZnCl₂ (1.0 M in diethyl ether, 1.5 mL, 1.5 mmol) were dissolved in MeOH (160 mL) and stirred at reflux under N₂ for 8 h. The reaction mixture was cooled to 0° C. and NaCNBH₃ (5.8 g, 93.0 mmol) was added portion wise, the reaction mixture was stirred at reflux under N₂ for 48 h. The reaction mixture was filtered through celite and the solvents were removed in vacuo. The residue was partitioned between H₂O (500 mL) and EtOAc (150 mL), and the aqueous layer was further extracted with EtOAc (2×150 mL). The combined organic layers were dried over Na₂SO₄ and the solvents were removed in vacuo. The residue was purified by column chromatography (Normal phase, Neutral silica gel, 100-200 mesh, 0 to 8% MeOH in DCM) to give two isomers of ethyl 3-(2-oxo-1-oxa-3,8-diazaspiro[4.6]undec-8-yl)-8-azabicyclo[3.2.1]octane-8-carboxylate, major isomer (3.00 g, 27.6%) as a colourless gum and minor isomer (0.40 g, 3.7%) as a colourless gum. The major isomer (100 mg) was further purified by chiral preparative HPLC [(Chiral PAK IB (250× 20) mm 5µ, 13.0 ml/min using an isocratic method in 0.1% DEA in n-hexane:IPA:MeOH (19:1:1) for 50 min] to give ethyl 3-(2-oxo-1-oxa-3,8-diazaspiro[4.6]undec-8-yl)-8-azabicyclo[3.2.1]octane-8-carboxylate, Example 9-2 Isomer 1 (45.0 mg, 45.0%) as colourless gum, ethyl 3-(2-oxo-1-oxa-3,8-diazaspiro[4.6]undec-8-yl)-8-azabicyclo[3.2.1]octane-8-carboxylate, Example 9-2 Isomer 2 (40.0 mg, 40.0%) as a colourless gum. The minor isomer (150 mg) was further purified by chiral preparative HPLC [(Chiral PAK IC SFC (250×21) mm 15.0 mL/min using an isocratic method in 0.1% DEA in n-hexane:IPA:THF:MeOH (14:1:1:4) for 33 min] to give ethyl 3-(2-oxo-1-oxa-3,8-diazaspiro[4.6]undec-8-yl)-8-azabicyclo[3.2.1]octane-8-carboxylate, Example 9-2 Isomer 3 (50.0 mg, 33.3%) as a colourless gum and ethyl 3-(2-oxo-1-oxa-3,8-diazaspiro[4.6]undec-8-yl)-8-azabicyclo[3.2.1]octane-8-carboxylate, Example 9-2 Isomer 4 (52.4 mg, 34.9%) as a colourless gum.

The data for the title compound are in Table 3.

TABLE 2

| | | Starting Materials and Intermediates | |
|---|---|---|---|
| Intermediate | Route | Name | Data |
| 1 | | 2,8-diazaspiro[4.5]decan-3-one.HCl | Commercially available, CAS: 945892-88-6 |
| 2 | Route 1 and intermediates 38 and 47 | 1-methyl-2,8-diazaspiro[4.5]decan-3-one.HCl | LCMS (Method F): m/z 169 (M + H)⁺ (ES⁺), at 4.65 min, UV inactive |
| 3 | Route 1 and intermediates 38 and 48 | 1-ethyl-2,8-diazaspiro[4.5]decan-3-one.HCl | LCMS (Method F): m/z 183 (M + H)⁺ (ES⁺), at 5.55 min, UV inactive |

TABLE 2-continued

Starting Materials and Intermediates

| Intermediate | Route | Name | Data |
|---|---|---|---|
| 4 | Route 1 and intermediates 38 and 49 | 1-propyl-2,8-diazaspiro[4.5]decan-3-one.HCl | LCMS (Method F): m/z 197 (M + H)$^+$ (ES$^+$), at 5.31 min, UV inactive |
| 5 | Route 1 and intermediates 38 and 50 | 1-benzyl-2,8-diazaspiro[4.5]decan-3-one.HCl | LCMS (Method F): m/z 245 (M + H)$^+$ (ES$^+$), at 1.47 min, UV active |
| 6 | Route 2 and intermediates 39 and 46 | 6-fluoro-2,8-diazaspiro[4.5]decan-3-one.HCl | LCMS (Method D): m/z 173 (M + H)$^+$ (ES$^+$), at 0.13 min, UV inactive |
| 7 | Route 3 and intermediates 38 and 46 | 2-ethyl-2,8-diazaspiro[4.5]decan-3-one.HCl | LCMS (Method H): m/z 183 (M + H)$^+$ (ES$^+$), at 5.36 min, UV inactive |
| 8 | | 1-oxa-3,8-diazaspiro[4.5]decan-2-one.HCl | Commercially available, CAS: 2052-96-0 |
| 9 | Route 3 and intermediates 37 and 51 | 4-methyl-1-oxa-3,8-diazaspiro[4.5]decan-2-one | LCMS (Method G): m/z 171 (M + H)$^+$ (ES$^+$), at 4.31 min, UV inactive |
| 10 | Route 3 and intermediates 37 and 52 | 4-ethyl-1-oxa-3,8-diazaspiro[4.5]decan-2-one | LCMS (Method G): m/z 185 (M + H)$^+$ (ES$^+$), at 3.27 min, UV inactive |
| 11 | Route 3 and intermediates 37 and 53 | 4-(propan-2-yl)-1-oxa-3,8-diazaspiro[4.5]decan-2-one | LCMS (Method G): m/z 199 (M + H)$^+$ (ES$^+$), at 3.68 min, UV inactive |
| 12 | Route 3 and intermediates 37 and 54 | 4,4-dimethyl-1-oxa-3,8-diazaspiro[4.5]decan-2-one | LCMS (Method G): m/z 185 (M + H)$^+$ (ES$^+$), at 1.90 min, UV active |
| 13 | | 1,3,8-triazaspiro[4.5]decan-2-one | Commercially available, CAS: 561314-52-1 |
| 14 | | 2-azabicyclo[2.2.1]heptane-2-carboxylic acid, 5-oxo-, 1,1-dimethylethyl ester | Commercially available, CAS: 198835-06-2 |
| 15 | Route 6 and intermediates 14 and 42 | 2-azabicyclo[2.2.1]heptane-2-carboxylic acid, 5-oxo-, ethyl ester | $^1$H NMR: (400 MHz, DMSO-d$_6$) δ: 1.08-1.23 (m, 3 H), 1.90-2.03 (m, 2 H), 2.07 (dd, J = 17.5, 4.0 Hz, 1 H), 2.26 (d, J = 17.5 Hz, 1 H), 2.78-2.83 (m, 1 H), 3.06-3.20 (m, 1 H), 3.35-3.48 (m, 1 H), 3.95-4.09 (m, 2 H), 4.45 (s, 1 H) |
| 16 | Route 5 and intermediates 18 and 41 | methyl 3-oxo-8-azabicyclo[3.2.1]octane-8-carboxylate | LCMS (Method C): m/z 184 (M + H)$^+$ (ES$^+$), at 0.72 min, UV inactive |
| 17 | | ethyl 3-oxo-8-azabicyclo[3.2.1]octane-8-carboxylate | Commercially available, CAS: 32499-64-2 |
| 18 | | nortropinone.HCl | Commercially available, CAS: 25602-68-0 |
| 19 | Route 5 and intermediates 18 and 43 | 2-fluoroethyl 3-oxo-8-azabicyclo[3.2.1]octane-8-carboxylate | LCMS (Method C): m/z 216 (M + H)$^+$ (ES$^+$), at 0.82 min, UV inactive |
| 20 | Route 5 and intermediates 18 and 44 | prop-2-yn-1-yl 3-oxo-8-azabicyclo[3.2.1]octane-8-carboxylate | LCMS (Method C): m/z 208 (M + H)$^+$ (ES$^+$), at 0.84 min, UV inactive |
| 21 | Route 5 and intermediates 18 and 45 | but-2-yn-1-yl 3-oxo-8-azabicyclo[3.2.1]octane-8-carboxylate | LCMS (Method C): m/z 222 (M + H)$^+$ (ES$^+$), at 1.00 min, UV inactive |
| 22 | Route 6 and intermediates 36 and 42 | ethyl 2-fluoro-3-oxo-8-azabicyclo[3.2.1]octane-8-carboxylate | $^1$H NMR: (400 MHz, CDCl$_3$) δ: 1.27-1.34 (m, 3 H), 1.42-1.55 (m, 1 H), 1.60-1.71 (m, 1 H), 1.89-2.19 (m, 2 H), 2.33-2.51 (m, 1 H), 2.63-3.11 (m, 1 H), 4.18-4.27 (m, 2 H), 4.29-4.50 (m, 1 H), 4.50-4.70 (m, 1 H), 4.70-4.97 (m, 1 H) |
| 23 | Route 5 and intermediates 18 and 40 | 8-butanoyl-8-azabicyclo[3.2.1]octan-3-one | LCMS (Method C): m/z 196 (M + H)$^+$ (ES$^+$), at 0.74 min, UV active |
| 24 | | tert-butyl 5-oxo-2-azabicyclo[2.2.2]octane-2-carboxylate | Commercially available, CAS: 617714-22-4 |
| 25 | Route 6 and intermediates 24 and 42 | ethyl 5-oxo-2-azabicyclo[2.2.2]octane-2-carboxylate | LCMS (Method C): m/z 198 (M + H)$^+$ (ES$^+$), at 0.84 min, UV active |
| 26 | | 3-Boc-3-azabicyclo[3.2.1]octan-8-one | Commercially available, CAS: 637301-19-0 |

TABLE 2-continued

Starting Materials and Intermediates

| Intermediate | Route | Name | Data |
|---|---|---|---|
| 27 | Route 6 and intermediates 26 and 42 | 3-azabicyclo[3.2.1]octane-3-carboxylic acid, 8-oxo-, ethyl ester | $^1$H NMR: (400 MHz, DMSO-d$_6$) δ: 1.19 (t, J = 7.0 Hz, 3 H), 1.46-1.68 (m, 2 H), 1.78-1.93 (m, 2 H), 2.10-2.24 (m., 2 H), 3.11-3.26 (m, 2 H), 3.97-4.23 (m, 4 H) |
| 28 | | tert-butyl 3-oxo-9-azabicyclo[3.3.1]nonane-9-carboxylate | Commercially available, CAS: 512822-27-4 |
| 29 | Route 6 and intermediates 38 and 42 | ethyl 3-oxo-9-azabicyclo[3.3.1]nonane-9-carboxylate | LCMS (Method C): m/z 212 (M + H)$^+$ (ES$^+$), at 2.06 min, UV active |
| 30 | Route 6 and intermediates 38 and 44 | prop-2-yn-1-yl 3-oxo-9-azabicyclo[3.3.1]nonane-9-carboxylate | LCMS (Method C): m/z 222 (M + H)$^+$ (ES$^+$), at 1.95 min, UV active |
| 31 | Route 6 and intermediates 38 and 45 | but-2-yn-1-yl 3-oxo-9-azabicyclo[3.3.1]nonane-9-carboxylate | LCMS (Method C): m/z 237 (M + H)$^+$ (ES$^+$), at 2.47 min, UV active |
| 32 | | tert-butyl 3-oxo-6-azabicyclo[3.2.1]octane-6-carboxylate | Commercially available, CAS: 359779-74-1 |
| 33 | Route 6 and intermediates 38 and 41 | methyl 3-oxo-6-azabicyclo[3.2.1]octane-6-carboxylate | $^1$H NMR: (400 MHz, DMSO-d$_6$) δ: 1.94-2.06 (m, 2 H), 2.24-2.34 (m, 1 H), 2.34-2.44 (m, 1 H), 2.57 (dd, J = 4.5, 2.0 Hz, 1 H), 2.59-2.70 (m, 2 H), 3.09-3.22 (m, 1 H), 3.22-3.31 (m, 1 H), 3.52-3.58 (m, 3 H), 4.12-4.20 (m, 1 H) |
| 34 | Route 6 and intermediates 32 and 42 | ethyl 3-oxo-6-azabicyclo[3.2.1]octane-6-carboxylate | $^1$H NMR: (400 MHz, DMSO-d$_6$) δ: 1.14 (td, J = 7.0, 4.0 Hz, 3 H), 1.94-2.05 (m, 2 H), 2.24-2.34 (m, 1 H), 2.46 (d, J = 2.5 Hz, 1 H), 2.57 (dd, J = 4.5, 2.0 Hz, 1 H), 2.59-2.71 (m, 2 H), 3.11-3.19 (m, 1 H), 3.24-3.31 (m, 1 H), 3.92-4.04 (m, 2 H), 4.12-4.19 (m, 1 H) |
| 35 | | 6-oxo-3-aza-bicyclo[3.2.1]octane-3-carboxylic acid tert-butyl ester | Commercially available, CAS: 1369502-46-4 |
| 36 | | 8-azabicyclo[3.2.1]octane-8-carboxylic acid, 2-fluoro-3-oxo-, 1,1-dimethylethyl ester | Commercially available, CAS: 1404196-37-7 |
| 37 | | N-benzyl-4-piperidinone | Commercially available, CAS: 3612-20-2 |
| 38 | | tert-butyl 4-oxopiperidine-1-carboxylate | Commercially available, CAS: 79099-07-3 |
| 39 | | tert-butyl-3-fluoro-4-oxo-piperidine-1-carboxylate | Commercially available, CAS: 211108-50-8 |
| 40 | | n-butyryl chloride | Commercially available, CAS: 141-75-3 |
| 41 | | methyl chloroformate | Commercially available, CAS: 79-22-1 |
| 42 | | ethyl chloroformate | Commercially available, CAS: 541-41-3 |
| 43 | | 2-fluoroethyl chloroformate | Commercially available, CAS: 462-27-1 |
| 44 | | prop-2-yn-1-yl chloroformate | Commercially available, CAS: 68622-10-6 |
| 45 | | but-2-yn-1-yl chloroformate | Commercially available, CAS: 202591-85-3 |
| 46 | | nitromethane | Commercially available, CAS: 75-52-5 |
| 47 | | nitroethane | Commercially available, CAS: 79-24-3 |
| 48 | | 1-nitropropane | Commercially available, CAS: 108-03-2 |
| 49 | | 1-nitrobutane | Commercially available, CAS: 627-05-4 |
| 50 | | 2-phenyl-1-nitroethane | Commercially available, CAS: 6125-24-2 |
| 51 | | 2-bromopropanoic acid ethyl ester | Commercially available, CAS: 535-11-5 |
| 52 | | 2-bromobutanoic acid ethyl ester | Commercially available, CAS: 533-68-6 |
| 53 | | 2-bromo-3-methylbutyric acid ethyl ester | Commercially available, CAS: 609-12-1 |

TABLE 2-continued

Starting Materials and Intermediates

| Intermediate | Route | Name | Data |
|---|---|---|---|
| 54 | | 2-bromo-2-methylpropionic acid ethyl ester | Commercially available, CAS: 600-00-0 |
| 55 | | 4-nitrophenyl chloroformate | Commercially available, CAS: 7693-46-1 |
| 56 | Route 5 and intermediates 18 and 55 | 4-nitrophenyl 3-oxo-8-azabicyclo[3.2.1]octane-8-carboxylate | LCMS (Method D): m/z 291 (M + H)$^+$ (ES$^+$), at 1.67 min, UV active |
| 57 | | 2,8-diazaspiro[4.5]decan-3-one | Commercially available, CAS: 561314-57-6 |
| 58 | Route 7 and intermediates 56 and 57 | 4-nitrophenyl 3-(3-oxo-2,8-diazaspiro[4.5]dec-8-yl)-8-azabicyclo[3.2.1]octane-8-carboxylate | LCMS (Method D): m/z 429 (M + H)$^+$ (ES$^+$), at 1.81 min and 1.86 min, |
| 59 | | ethanol-1,1,2,2,2-d$_5$ | Commercially available CAS: 1859-08-1 |
| 60 | | ethanol-1,1-d$_2$ | Commercially available CAS: 1859-09-2 |
| 61 | | ethanol-2,2,2-d$_3$ | Commercially available CAS: 1759-87-1 |
| 62 | | tert-butyl 6-oxo-3-azabicyclo[3.1.1]heptane-3-carboxylate | Commercially available: CAS: 1305208-01-8 |
| 63 | Route 6 and intermediates 42 and 62 | ethyl 6-oxo-3-azabicyclo[3.1.1]heptane-3-carboxylate | $^1$H NMR: (400 MHz, CDCl$_3$) δ: 1.11-1.23 (m, 3 H), 1.69-1.76 (m, 1 H), 2.03-2.13 (m, 1 H), 2.94-3.11 (m, 2 H), 3.80-3.90 (m, 2 H), 3.93-4.12 (m, 4 H). |
| 64 | | ethyl (3-endo)-3-[4-(2-ethoxy-2-oxoethyl)-4-(nitromethyl)piperidin-1-yl]-8-azabicyclo[3.2.1]octane-8-carboxylate | LCMS (Method D): m/z 412 (M + H)$^+$ (ES$^+$), at 2.25 min |
| 65 | | 1-tert-Butoxycarbonylperhydroazepin-4-one | Commercially available: CAS: 188975-88-4 |
| 66 | Route 3 and intermediates 46 and 65 | tert-butyl 3-oxo-2,8-diazaspiro[4.6]undecane-8-carboxylate | $^1$H NMR: (400 MHz, DMSO) δ: 1.37 (s, 9 H), 1.44-1.67 (m, 6 H), 1.90-2.05 (m, 2 H), 2.97 (s, 2 H), 3.21-3.29 (m, 4 H), 7.49 (br. s., 1 H) |
| 67 | Route 8 and intermediate 38 | 1-benzyl-1,2,8-triazaspiro[4.5]decan-3-one | LCMS (Method G): m/z 246 (M + H)$^+$ (ES$^+$) at 4.35 min UV active |
| 68 | Route 6 and intermediates 69 and 70 | propan-2-yl 3-oxo-8-azabicyclo[3.2.1]octane-8-carboxylate | LCMS (Method J): m/z 212 (M + H)$^+$ (ES$^+$) at 4.00 min UV active |
| 69 | | tert-butyl 3-oxo-8-azabicyclo[3.2.1]octane-8-carboxylate | Commercially available CAS: 185099-67-6 |
| 70 | | isopropylchloroformate | Commercially available CAS: 108-23-6 |
| 71 | Route 6 and intermediates 69 and 72 | S-methyl 3-oxo-8-azabicyclo[3.2.1]octane-8-carbothioate | LCMS (Method J): m/z 200 (M + H)$^+$ (ES$^+$) at 3.63 min UV active |
| 72 | | S-methyl carbonochloridothioate | Commercially available CAS: 18369-83-0 |
| 73 | | 1-bromopropane | Commercially available CAS: 106-94-5 |
| 74 | | 2-iodopropane | Commercially available CAS: 75-30-9 |
| 75 | | 1-bromo-2-methyl propane | Commercially available CAS: 78-77-3 |
| 76 | | 1-Bromo-2-methoxy ethane | Commercially available CAS: 6482-24-2 |
| 77 | Route 9 and Intermediates 69, 78, and 79 | S-ethyl 3-oxo-8-azabicyclo[3.2.1]octane-8-carbothioate | $^1$H NMR: (400 MHz, DMSO) δ: 1.33 (t, J = 7.2 Hz, 3 H), 1.60-1.66 (m, 2 H), 2.00-2.06 (m, 2 H), 2.62-2.66 (m, 2 H), 2.86-2.90 (m, 2 H), 3.11-3.15 (m, 2 H), 4.55-4.60 (m, 2 H) |
| 78 | | carbonyldiimidazole | Commercially available CAS: 530-62-1 |
| 79 | | Ethanethiol | Commercially available CAS: 75-08-1 |
| 80 | Route 10 and intermediate 81 | 1-oxa-3,8-diazaspiro[4.6]undecan-2-one | LCMS (Method J): m/z 171 (M + H)$^+$ (ES$^+$) at 2.49 min |
| 81 | | azepan-4-one HCl salt | Commercially available: CAS: 50492-22-3 |

TABLE 2-continued

Starting Materials and Intermediates

| Intermediate | Route | Name | Data |
| --- | --- | --- | --- |
| 82 | Route 11 and Intermediate 83 | 4-(pyridin-2-ylmethyl)-1-oxa-3,8-diazaspiro[4.5]decan-2-one | LCMS (Method o): m/z 248 (M + H)$^+$ (ES$^+$) at 5.23 min UV active |
| 83 | | pyridine-2-carboxaldehyde | Commerically available CAS: 1121-60-4 |
| 84 | | cyclopropyl methyl bromide | Commerically available CAS: 7051-34-5 |
| 85 | | ethyl 4,4,4-trifluorobutanoate | Commercially available, CAS: 317-26-6 |
| 86 | Route 12 and intermediates 37 and 85 | 4-(2,2,2-trifluoroethyl)-1-oxa-3,8-diazaspiro[4.5]decan-2-one | LCMS (Method H): m/z 239 (M + H)$^+$ (ES$^+$) at 2.79 min UV inactive |
| 87 | | propionaldehyde | Commercially available CAS: 123-38-6 |
| 88 | Route 13 and intermediates 38 and 87 | 1-propyl-1,2,8-triazaspiro[4.5]decan-3-one.HCl | LCMS (Method K): m/z 198 (M + H)$^+$ (ES$^+$), at 2.55 min, UV inactive |

TABLE 3

| Ex. No. | Name | Intermediate | Synthetic method | ¹H NMR | LCMS Method | LCMS data |
|---|---|---|---|---|---|---|
| 1-1 | Isomer 1: ethyl 5-(2-oxo-1-oxa-3,8-diazaspiro[4.5]dec-8-yl)-2-azabicyclo[2.2.1]heptane-2-carboxylate | 1 and 15 | a | (400 MHz, DMSO-$d_6$) δ: 1.13 (m, 3 H), 1.34-1.49 (m, 2 H), 1.49-1.59 (m, 1 H), 1.71 (s, 3 H), 1.68 (s, 2 H), 2.20-2.25 (m, 1 H), 2.30-2.44 (m, 3 H), 2.62-2.72 (m, 2 H), 2.78 (t, J = 9.8 Hz, 1 H), 3.13 (s, 1 H), 3.19 (s, 2 H), 3.87-4.03 (m, 2 H), 4.05 (s, 1 H), 7.45 (s, 1 H) | E | m/z 324 (M + H)⁺ (ES+), at 1.73 min, UV inactive |
| 2-1 | Isomer 1: methyl 3-(3-oxo-2,8-diazaspiro[4.5]dec-8-yl)-8-azabicyclo[3.2.1]octane-8-carboxylate | 1 and 16 | a | (400 MHz, DMSO-$d_6$) δ: 1.52 (m, 4 H), 1.67-1.93 (m, 8 H), 1.96 (s, 2 H), 2.14-2.24 (m, 1 H), 2.24-2.43 (m, 4 H), 2.97 (s, 2 H), 3.55 (s, 3 H), 4.04 (d, J = 6.3 Hz, 2 H), 7.47 (s, 1 H) | E | m/z 322 (M + H)⁺ (ES+), at 2.05 min, UV inactive |
| 2-1 | Isomer 2: methyl 3-(3-oxo-2,8-diazaspiro[4.5]dec-8-yl)-8-azabicyclo[3.2.1]octane-8-carboxylate | 1 and 16 | a | (400 MHz, DMSO-$d_6$) δ: 1.32-1.54 (m, 6 H), 1.54-1.67 (m, 4 H), 1.71-1.89 (m, 2 H), 1.94 (s, 2 H), 2.19-2.46 (m, 4 H), 2.59-2.84 (m, 1 H), 2.95 (s, 2 H), 3.56 (s, 3 H), 4.04-4.20 (m, 2 H), 7.46 (s, 1 H) | E | m/z 322 (M + H)⁺ (ES+), at 2.14 min, UV inactive |
| 2-2 | Isomer 1: ethyl 3-(3-oxo-2,8-diazaspiro[4.5]dec-8-yl)-8-azabicyclo[3.2.1]octane-8-carboxylate | 1 and 17 | a | (400 MHz, DMSO-$d_6$) δ: 1.14 (t, J = 7.0 Hz, 3 H), 1.42-1.59 (m, 4 H), 1.67-1.92 (m, 9 H), 1.96 (s, 2 H), 2.10-2.45 (m, 4 H), 2.97 (s, 2 H), 3.90-4.09 (m, 4 H), 7.49 (br. s., 1 H) | B | m/z 336 (M + H)⁺ (ES+), at 2.26 min, UV inactive |
| 2-2 | Isomer 2: ethyl 3-(3-oxo-2,8-diazaspiro[4.5]dec-8-yl)-8-azabicyclo[3.2.1]octane-8-carboxylate | 1 and 17 | a | (400 MHz, DMSO-$d_6$) δ: 1.15 (t, J = 7.0 Hz, 3 H), 1.31-1.56 (m, 6 H), 1.56-1.72 (m, 4 H), 1.72-1.91 (m, 2 H), 1.94 (s, 2 H), 2.20-2.44 (m, 4 H), 2.70-2.75 (m, 1 H), 2.95 (s, 2 H), 4.01 (q, J = 7.0 Hz, 2 H), 4.08-4.17 (m, 2 H), 7.44 (s, 1 H) | B | m/z 336 (M + H)⁺ (ES+), at 2.14 min, UV inactive |
| 2-3 | Isomer 1: 2-fluoroethyl 3-(3-oxo-2,8-diazaspiro[4.5]dec-8-yl)-8-azabicyclo[3.2.1]octane-8-carboxylate | 1 and 19 | a | (400 MHz, DMSO-$d_6$) δ: 1.53-1.59 (m, 4 H), 1.66-1.95 (m, 8 H), 1.97 (s, 2 H), 2.10-2.45 (m, 5 H), 2.98 (s, 2 H), 3.95-4.13 (m, 2 H), 4.13-4.38 (m, 2 H), 4.51 (t, J = 4.0 Hz, 1 H), 4.63 (t, J = 4.0 Hz, 1 H), 7.47 (s, 1 H) | E | m/z 354 (M + H)⁺ (ES+), at 2.34 min, UV inactive |
| 2-3 | Isomer 2: 2-fluoroethyl 3-(3-oxo-2,8-diazaspiro[4.5]dec-8-yl)-8-azabicyclo[3.2.1]octane-8-carboxylate | 1 and 19 | a | (400 MHz, DMSO-$d_6$) δ: 1.35-1.55 (m, 6 H), 1.55-1.74 (m, 4 H), 1.81-1.92 (m, 2 H), 1.95 (s, 2 H), 2.20-2.46 (m, 4 H), 2.68-2.85 (m, 1 H), 2.95 (s, 2 H), 4.02-4.23 (m, 3 H), 4.23-4.35 (m, 1 H), 4.51 (t, J = 4.0 Hz, 1 H), 4.63 (t, J = 4.0 Hz, 1 H), 7.46 (s, 1 H) | E | m/z 354 (M + H)⁺ (ES+), at 2.29 min, UV inactive |
| 2-4 | Isomer 1: prop-2-yn-1-yl 3-(3-oxo-2,8-diazaspiro[4.5]dec-8-yl)-8-azabicyclo[3.2.1]octane-8-carboxylate | 1 and 20 | a | (400 MHz, DMSO-$d_6$) δ: 1.41-1.58 (m, 4 H), 1.58-1.70 (m, 1 H), 1.70-1.93 (m, 7 H), 1.96 (s, 2 H), 2.17-2.43 (m, 5 H), 2.97 (s, 2 H), 3.48 (t, J = 2.34 Hz, 1 H), 4.01-4.16 (m, 2 H), 4.64 (d, J = 2.34 Hz, 2 H), 7.47 (s, 1 H) | E | m/z 346 (M + H)⁺ (ES+), at 2.49 min, UV inactive |
| 2-4 | Isomer 2: prop-2-yn-1-yl 3-(3-oxo-2,8-diazaspiro[4.5]dec-8-yl)-8-azabicyclo[3.2.1]octane-8-carboxylate | 1 and 20 | a | (400 MHz, DMSO-$d_6$) δ: 1.46 (t, J = 5.5 Hz, 6 H), 1.55-1.73 (m, 4 H), 1.81-1.92 (m, 2 H), 1.92-1.98 (m, 2 H), 2.23-2.45 (m, 4 H), 2.71-2.80 (m, 1 H), 2.90-3.00 (m, 2 H), 3.44-3.52 (m, 1 H), 4.03-4.19 (m, 2 H), 4.65 (dd, J = 2.5, 1.5 Hz, 2 H), 7.45 (s, 1 H) | E | m/z 346 (M + H)⁺ (ES+), at 2.46 min, UV inactive |
| 2-5 | Isomer 1: but-2-yn-1-yl 3-(3-oxo-2,8-diazaspiro[4.5]dec-8-yl)-8-azabicyclo[3.2.1]octane-8-carboxylate | 1 and 21 | a | (400 MHz, DMSO-$d_6$) δ: 1.35-1.58 (m, 4 H), 1.71 (m, 1 H), 1.71-1.94 (m, 10 H), 1.96 (s, 2 H), 2.14-2.56 (m, 5 H), 2.96 (s, 2 H), 4.03-4.14 (m, 2 H), 4.55-4.65 (m, 2 H), 7.47 (s, 1 H) | E | m/z 360 (M + H)⁺ (ES+), at 2.80 min, UV inactive |

TABLE 3-continued

| Ex. No. | Name | Intermediate | Synthetic method | ¹H NMR | LCMS Method | LCMS data |
|---|---|---|---|---|---|---|
| 2-5 | Isomer 2: but-2-yn-1-yl 3-(3-oxo-2,8-diazaspiro[4.5]dec-8-yl)-8-azabicyclo[3.2.1]octane-8-carboxylate | 1 and 21 | a | (400 MHz, DMSO-d₆) δ: 1.36-1.55 (m, 6 H), 1.55-1.72 (m, 4 H), 1.79 (t, J = 2.5 Hz, 3 H), 1.81-1.92 (m, 2 H), 1.94 (s, 2 H), 2.22-2.45 (m, 4 H), 2.73-2.80 (m, 1 H), 2.95 (s, 2 H), 4.03-4.20 (m, 2 H), 4.61 (q, J = 2.5 Hz, 2 H), 7.45 (s, 1 H) | E | m/z 360 (M + H)⁺ (ES+), at 2.75 min, UV inactive |
| 2-6 | Isomer 2: 8-(8-butanoyl-8-azabicyclo[3.2.1]oct-3-yl)-2,8-diazaspiro[4.5]decan-3-one | 1 and 23 | a | (400 MHz, DMSO-d₆) δ: 0.86 (t, J = 7.5 Hz, 3 H), 1.35-1.55 (m, 8 H), 1.55-1.78 (m, 5 H), 1.80-1.92 (m, 1 H), 1.92-2.02 (m, 2 H), 2.09-2.29 (m, 2 H), 2.29-2.46 (m, 4 H), 2.70-2.89 (m, 1 H), 2.95 (s, 2 H), 4.12-4.31 (m, 1 H), 4.36-4.58 (m, 1 H), 7.46 (s, 1 H) | E | m/z 334 (M + H)⁺ (ES+), at 2.17 min, UV inactive |
| 2-7 | Isomer 1: ethyl 3-(1-methyl-3-oxo-2,8-diazaspiro[4.5]dec-8-yl)-8-azabicyclo[3.2.1]octane-8-carboxylate | 2 and 17 | a | (400 MHz, DMSO-d₆) δ: 0.96 (d, J = 6.5 Hz, 3 H), 1.14 (t, J = 7.0 Hz, 3 H), 1.34-1.50 (m, 3 H), 1.67-1.81 (m, 4 H), 1.81-2.05 (m, 5 H), 2.13-2.27 (m, 1 H), 2.36-2.47 (m, 2 H), 2.52-2.61 (m, 1 H), 2.67-2.85 (m, 1H), 3.13-3.28 (m, 3 H), 3.95-4.08 (m, 4 H), 7.57 (s, 1 H) | E | m/z 350 (M + H)⁺ (ES+), at 2.50 min, UV inactive |
| 2-7 | Isomer 2: ethyl 3-(1-methyl-3-oxo-2,8-diazaspiro[4.5]dec-8-yl)-8-azabicyclo[3.2.1]octane-8-carboxylate | 2 and 17 | a | (400 MHz, DMSO-d₆) δ: 0.94 (d, J = 6.5 Hz, 3 H), 1.15 (t, J = 7.0 Hz, 3 H), 1.24-1.37 (m, 1 H), 1.37-1.54 (m, 4 H), 1.58-1.72 (m, 4 H), 1.74-1.86 (m, 2 H), 1.90 (d, J = 16.40 Hz, 1 H), 2.06 (d, J = 16.40 Hz, 1 H), 2.09-2.28 (m, 2 H), 2.51-2.64 (m, 2 H), 2.66-2.88 (m, 1 H), 3.19 (q, J = 6.38 Hz, 2 H), 3.95-4.06 (m, 2 H), 4.07-4.22 (m, 2 H), 7.55 (s, 1 H) | E | m/z 350 (M + H)⁺ (ES+), at 2.72 min, UV inactive |
| 2-8 | Isomer 1: ethyl 3-(1-ethyl-3-oxo-2,8-diazaspiro[4.5]dec-8-yl)-8-azabicyclo[3.2.1]octane-8-carboxylate | 3 and 17 | b | (400 MHz, DMSO-d₆) δ: 0.89 (t, J = 7.5 Hz, 3 H), 1.10-1.27 (m, 4 H), 1.37-1.76 (m, 6 H), 1.71-2.14 (m, 9 H), 2.18-2.35 (m, 1 H), 2.54-2.59 (m, 2 H), 2.62-2.83 (m, 2 H), 2.91-3.00 (m, 1 H), 3.98-4.09 (m, 4 H), 7.88 (s, 1 H) | F | m/z 364 (M + H)⁺ (ES+), at 1.60 min, UV inactive |
| 2-8 | Isomer 2: ethyl 3-(1-ethyl-3-oxo-2,8-diazaspiro[4.5]dec-8-yl)-8-azabicyclo[3.2.1]octane-8-carboxylate | 3 and 17 | b | (400 MHz, DMSO-d₆) δ: 0.88 (t, J = 7.5 Hz, 3 H), 1.17 (t, J = 7.0 Hz, 4 H), 1.31-1.55 (m, 7 H), 1.57-1.70 (m, 4 H), 1.77-1.98 (m, 3 H), 2.01-2.24 (m, 3 H), 2.55-2.62 (m, 2 H), 2.65-2.80 (m, 1H), 2.88-3.00 (m, 1 H), 3.98-4.08 (m, 2 H), 4.09-4.17 (m, 2 H), 7.85 (s, 1 H) | F | m/z 364 (M + H)⁺ (ES+), at 1.61 min, UV inactive |
| 2-9 | Isomer 1: ethyl 3-(3-oxo-1-propyl-2,8-diazaspiro[4.5]dec-8-yl)-8-azabicyclo[3.2.1]octane-8-carboxylate | 4 and 17 | b | (400 MHz, DMSO-d₆) δ: 0.88 (t, J = 7.0 Hz, 3 H), 1.10-1.26 (m, 5 H), 1.29-1.59 (m, 6 H), 1.67-2.12 (m, 12 H), 2.16-2.25 (m, 1 H), 2.56-2.85 (m, 2 H), 3.00-3.11 (m, 1 H), 3.94-4.12 (m, 4 H), 7.85 (s, 1 H) | F | m/z 378 (M + H)⁺ (ES+), at 1.63 min, UV inactive |
| 2-9 | Isomer 2: ethyl 3-(3-oxo-1-propyl-2,8-diazaspiro[4.5]dec-8-yl)-8-azabicyclo[3.2.1]octane-8-carboxylate | 4 and 17 | b | (400 MHz, DMSO-d₆) δ: 0.87 (t, J = 7.0 Hz, 3 H), 1.17 (t, J = 7.0 Hz, 5 H), 1.28-1.55 (m, 8 H), 1.57-1.70 (m, 4 H), 1.79-1.96 (m, 3 H), 2.01-2.23 (m, 3 H), 2.53-2.60 (m, 2 H), 2.65-2.80 (m, 1H), 3.04 (d, J = 7.5 Hz, 1 H), 3.99-4.09 (m, 2 H), 4.10-4.21 (m, 2 H), 7.82 (s, 1 H) | F | m/z 378 (M + H)⁺ (ES+), at 1.64 min, UV inactive |

TABLE 3-continued

| Ex. No. | Name | Intermediate | Synthetic method | ¹H NMR | LCMS Method | LCMS data |
|---|---|---|---|---|---|---|
| 2-10 | Isomer 1: ethyl 3-(1-benzyl-3-oxo-2,8-diazaspiro[4.5]dec-8-yl)-8-azabicyclo[3.2.1]octane-8-carboxylate | 5 and 17 | b | (400 MHz, DMSO-d₆) δ: 1.18 (t, J = 7.0 Hz, 3 H), 1.35-1.54 (m, 5 H), 1.55-1.70 (m, 6 H), 1.76-2.01 (m, 3 H), 2.09-2.26 (m, 3 H), 2.55-2.64 (m, 2 H), 2.66-2.87 (m, 2 H), 3.38-3.45 (m, 1 H), 3.98-4.09 (m, 2 H), 4.11-4.19 (m, 2 H), 7.14-7.24 (m, 3 H), 7.26-7.34 (m, 2 H), 7.40 (s, 1 H) | H | m/z 426 (M + H)⁺ (ES+), at 9.35 min, UV active |
| 2-10 | Isomer 2: ethyl 3-(1-benzyl-3-oxo-2,8-diazaspiro[4.5]dec-8-yl)-8-azabicyclo[3.2.1]octane-8-carboxylate | 5 and 17 | b | (400 MHz, MeOD-d₄) δ: 1.20-1.40 (m, 4 H), 1.60-1.78 (m, 5 H), 1.79-2.00 (m, 5 H), 2.13-2.34 (m, 5 H), 2.34-2.45 (m, 1 H), 2.62 (dd, J = 13.5, 10.5 Hz, 1 H), 2.79-3.01 (m, 3 H), 3.58 (dd, J = 10.0, 4.5 Hz, 1 H), 4.07-4.19 (m, 2 H), 4.20-4.31 (m, 2 H), 7.19-7.37 (m, 5 H), NH not observed | H | m/z 426 (M + H)⁺ (ES+), at 9.76 min, UV active |
| 2-11 | Isomer 1: ethyl 2-fluoro-3-(3-oxo-2,8-diazaspiro[4.5]dec-8-yl)-8-azabicyclo[3.2.1]octane-8-carboxylate | 1 and 22 | a | (400 MHz, DMSO-d₆) δ: 1.06-1.20 (m, 3 H), 1.50 (s, 6 H), 1.53-1.57 (m, 1 H), 1.57-1.69 (m, 1 H), 1.69-1.93 (m, 1 H), 1.93-2.09 (m, 3 H), 2.33-2.45 (m, 4 H), 2.53-2.58 (m, 1 H), 2.98 (s, 2 H), 3.99 (q, J = 7.0 Hz, 2 H), 4.09-4.22 (m, 1 H), 4.29 (dd, J = 17.0, 8.0 Hz, 1 H), 4.54 (d, J = 4.5 Hz, 0.5 H), 4.67 (d, J = 4.5 Hz, 0.5 H), 7.47 (s, 1 H) | E | m/z 354 (M + H)⁺ (ES+), at 2.32 min, UV inactive |
| 2-11 | Isomer 2: ethyl 2-fluoro-3-(3-oxo-2,8-diazaspiro[4.5]dec-8-yl)-8-azabicyclo[3.2.1]octane-8-carboxylate | 1 and 22 | a | (400 MHz, DMSO-d₆) δ: 1.08-1.18 (m 3 H), 1.39-1.52 (m, 4 H), 1.53-1.65 (m, 3 H), 1.66-1.82 (m, 3 H), 1.95 (s, 2 H), 2.32-2.48 (m, 4 H), 2.59-2.69 (m, 1 H), 2.96 (s, 2 H), 3.94-4.06 (m, 2 H), 4.12-4.25 (m, 1 H), 4.25-4.44 (m, 1 H), 4.62-4.75 (m, 0.5 H), 4.75-4.85 (m, 0.5 H), 7.46 (s, 1 H) | E | m/z 354 (M + H)⁺ (ES+), at 2.08 min, UV inactive |
| 2-12 | Isomer 1: ethyl 3-(6-fluoro-3-oxo-2,8-diazaspiro[4.5]dec-8-yl)-8-azabicyclo[3.2.1]octane-8-carboxylate | 6 and 17 | a | (400 MHz, DMSO-d₆) δ: 1.10-1.17 (m, 3 H), 1.41-1.57 (m, 2 H), 1.57-1.67 (m, 1 H), 1.67-1.84 (m, 6 H), 1.84-1.95 (m, 2 H), 1.97-2.16 (m, 2 H), 2.18-2.30 (m, 2 H), 2.88-3.05 (m, 1 H), 3.10-3.23 (m, 1 H), 3.26-3.30 (m, 1 H), 3.92-4.08 (m, 4 H), 4.08-4.21 (m, 1 H), 4.32-4.62 (m, 1 H), 7.59 (s, 1 H) | E | m/z 354 (M + H)⁺ (ES+), at 0.25 min, UV inactive |
| 2-12 | Isomer 2: ethyl 3-(6-fluoro-3-oxo-2,8-diazaspiro[4.5]dec-8-yl)-8-azabicyclo[3.2.1]octane-8-carboxylate | 6 and 17 | a | (400 MHz, DMSO-d₆) δ: 1.15 (t, J = 7.0 Hz, 3 H), 1.38-1.52 (m, 3 H), 1.53-1.74 (m 5 H), 1.75-1.89 (m, 2 H), 1.98 (d, J = 17.0 Hz, 1 H), 2.13 (d, J = 17.0 Hz, 1 H), 2.24-2.45 (m, 2 H), 2.50-2.65 (m, 2 H), 2.72-2.86 (m, 1 H), 2.90 (d, J = 10.0 Hz, 1 H), 3.26 (d, J = 10.0 Hz, 1 H), 3.94-4.07 (m, 2 H), 4.07-4.17 (m, 2 H), 4.33-4.41 (m, 0.5 H), 4.43-4.54 (m, 0.5 H), 7.57 (s, 1 H) | E | m/z 354 (M + H)⁺ (ES+), at 2.17 min, UV inactive |
| 2-13 | Isomer 2: ethyl 3-(2-ethyl-3-oxo-2,8-diazaspiro[4.5]dec-8-yl)-8-azabicyclo[3.2.1]octane-8-carboxylate | 7 and 17 | b | (400 MHz, DMSO-d₆) δ: 1.00 (t, J = 7.0 Hz, 3 H), 1.17 (t, J = 7.0 Hz, 3 H), 1.42-1.61 (m, 4 H), 1.71-1.98 (m, 8 H), 2.09 (s, 2 H), 2.18-2.27 (m, 1 H), 2.28-2.45 (m, 3 H), 3.12 (s, 2 H), 3.18 (q, J = 7.0 Hz, 2 H), 3.41-3.55 (m, 1 H), 3.95-4.17 (m, 4 H) | F | m/z 364 (M + H)⁺ (ES+), at 1.58 min, UV inactive |
| 2-14 | Isomer 1: ethyl 3-(2-oxo-1-oxa-3,8-diazaspiro[4.5]dec-8-yl)-8-azabicyclo[3.2.1]octane-8-carboxylate | 8 and 17 | a | (400 MHz, DMSO-d₆) δ: 1.15 (t, J = 7.0 Hz, 3 H), 1.64-1.93 (m, 13 H), 2.20-2.30 (m, 1 H), 2.33-2.46 (m, 3 H), 3.19 (s, 2 H), 3.91-4.10 (m, 4 H), 7.42 (s, 1 H) | B | m/z 338 (M + H)⁺ (ES+), at 2.24 min, UV inactive |

TABLE 3-continued

| Ex. No. | Name | Intermediate | Synthetic method | ¹H NMR | LCMS Method | LCMS data |
|---|---|---|---|---|---|---|
| 2-14 | Isomer 2: ethyl 3-(2-oxo-1-oxa-3,8-diazaspiro[4.5]dec-8-yl)-8-azabicyclo[3.2.1]octane-8-carboxylate | 8 and 17 | a | (400 MHz, DMSO-d₆) δ: 1.15 (t, J = 7.0 Hz, 3 H), 1.35-1.55 (m 2 H), 1.56-1.76 (m, 9 H), 1.76-1.86 (m, 2 H), 2.43 (d, J = 14.0 Hz, 3 H), 2.71-2.89 (m, 1 H), 3.17 (s, 2 H), 3.94-4.08 (m, 2 H), 4.08-4.19 (m, 1 H), 7.41 (s, 1 H) | B | m/z 338 (M + H)⁺ (ES+), at 2.23 min, UV inactive |
| 2-15 | Isomer 1: ethyl 3-(4-methyl-2-oxo-1-oxa-3,8-diazaspiro[4.5]dec-8-yl)-8-azabicyclo[3.2.1]octane-8-carboxylate | 9 and 17 | b | (400 MHz, DMSO-d₆) δ: 1.02 (d, J = 6.5 Hz, 3 H), 1.12-1.25 (m, 3 H), 1.36-1.75 (m, 10 H), 1.78-1.94 (m, 2 H), 2.23-2.41 (m, 2 H), 2.59-2.72 (m, 2 H), 2.76-2.89 (m, 1 H), 3.41-3.52 (m, 1 H), 3.97-4.09 (m, 2 H), 4.10-4.23 (m, 2 H), 7.54 (s, 1 H) | E | m/z 352 (m + H)⁺ (ES+) at 1.69 min, UV inactive |
| 2-15 | Isomer 2: ethyl 3-(4-methyl-2-oxo-1-oxa-3,8-diazaspiro[4.5]dec-8-yl)-8-azabicyclo[3.2.1]octane-8-carboxylate | 9 and 17 | b | (400 MHz, DMSO-d₆) δ: 1.03 (d, J = 6.5 Hz, 3 H), 1.17 (t, J = 7.0 Hz, 3 H), 1.53-1.96 (m, 12 H), 2.02-2.21 (m, 2 H), 2.22-2.35 (m, 1 H), 2.76-2.95 (m, 2 H), 3.47 (q, J = 6.5 Hz, 1 H), 3.92-4.17 (m, 4 H), 7.55 (s, 1 H) | E | m/z 352 (m + H)⁺ (ES+) at 1.89 min, UV inactive |
| 2-16 | Isomer 1: ethyl 3-(4-ethyl-2-oxo-1-oxa-3,8-diazaspiro[4.5]dec-8-yl)-8-azabicyclo[3.2.1]octane-8-carboxylate | 10 and 17 | b | (400 MHz, DMSO-d₆) δ: 0.88 (t, J = 7.0 Hz, 3 H), 1.18 (t, J = 7.0 Hz, 3 H), 1.21-1.34 (m, 1 H), 1.36-1.76 (m, 10 H), 1.77-1.93 (m, 2 H), 2.23-2.41 (m, 2 H), 2.57-2.70 (m, 2 H), 2.72-2.87 (m, 1 H), 3.14-3.24 (m, 2 H), 3.98-4.10 (m, 2 H), 4.11-4.20 (m, 2 H), 7.78 (br. s., 1 H) | E | m/z 366 (m + H)⁺ (ES+) at 2.19 min, UV inactive |
| 2-16 | Isomer 2: ethyl 3-(4-ethyl-2-oxo-1-oxa-3,8-diazaspiro[4.5]dec-8-yl)-8-azabicyclo[3.2.1]octane-8-carboxylate | 10 and 17 | b | (400 MHz, DMSO-d₆) δ: 0.89 (t, J = 7.0 Hz, 3 H), 1.17 (t, J = 7.0 Hz, 3 H), 1.21-1.36 (m, 1 H), 1.41-1.56 (m, 1 H), 1.57-1.96 (m, 12 H), 2.00-2.19 (m, 2 H), 2.21-2.34 (m, 1 H), 2.81-2.95 (m, 2 H), 3.18-3.26 (m, 1 H), 3.94-4.16 (m, 4 H), 7.80 (s, 1 H) | E | m/z 366 (m + H)⁺ (ES+) at 2.33 min, UV inactive |
| 2-17 | Isomer 1: ethyl 3-[2-oxo-4-(propan-2-yl)-1-oxa-3,8-diazaspiro[4.5]dec-8-yl]-8-azabicyclo[3.2.1]octane-8-carboxylate | 11 and 17 | b | (400 MHz, DMSO-d₆) δ: 0.86 (dd, J = 10.0, 6.5 Hz, 6 H), 1.18 (t, J = 7.0 Hz, 3H), 1.38-1.55 (m, 2 H), 1.56-1.91 (m, 11 H), 2.25-2.41 (m, 2 H), 2.58-2.71 (m, 2 H), 2.74-2.87 (m, 1 H), 3.03-3.11 (m, 1 H), 3.97-4.10 (m, 2 H), 4.11-4.21 (m, 2 H), 7.69 (s, 1 H) | E | m/z 380 (m + H)⁺ (ES+) at 2.50 min, UV inactive |
| 2-17 | Isomer 2: ethyl 3-[2-oxo-4-(propan-2-yl)-1-oxa-3,8-diazaspiro[4.5]dec-8-yl]-8-azabicyclo[3.2.1]octane-8-carboxylate | 11 and 17 | b | (400 MHz, DMSO-d₆) δ: 0.87 (dd, J = 11.0, 6.5 Hz, 6 H), 1.12-1.26 (m, 4 H), 1.60-1.94 (m, 13 H), 2.04-2.18 (m, 2 H), 2.23-2.36 (m, 1 H), 2.81-2.98 (m, 2 H), 3.05-3.17 (m, 1 H), 3.94-4.17 (m, 4 H), 7.72 (br. s., 1 H) | E | m/z 380 (m + H)⁺ (ES+) at 2.71 min, UV inactive |
| 2-18 | Isomer 1: ethyl 3-(4,4-dimethyl-2-oxo-1-oxa-3,8-diazaspiro[4.5]dec-8-yl)-8-azabicyclo[3.2.1]octane-8-carboxylate | 12 and 17 | b | (400 MHz, DMSO-d₆) δ: 1.08 (s, 6 H), 1.18 (t, J = 7.0 Hz, 3 H), 1.41-1.60 (m, 3 H), 1.60-1.75 (m, 6 H), 1.77-1.94 (m, 2 H), 2.15-2.29 (m, 2 H), 2.64-2.84 (m, 4 H), 3.97-4.09 (m, 2 H), 4.10-4.21 (m, 2 H), 7.48 (s, 1 H) | E | m/z 366 (m + H)⁺ (ES+) at 2.09 min, UV inactive |
| 2-18 | Isomer 2: ethyl 3-(4,4-dimethyl-2-oxo-1-oxa-3,8-diazaspiro[4.5]dec-8-yl)-8-azabicyclo[3.2.1]octane-8-carboxylate | 12 and 17 | b | (400 MHz, DMSO-d₆) δ: 1.10 (s, 6 H), 1.17 (t, J = 7.0 Hz, 3 H), 1.51-1.65 (m, 2 H), 1.67-2.05 (m, 12 H), 2.21-2.32 (m, 1 H), 2.96-3.11 (m, 2 H), 3.97-4.15 (m, 4 H), 7.50 (br. s., 1 H) | E | m/z 366 (m + H)⁺ (ES+) at 2.24 min, UV inactive |

TABLE 3-continued

| Ex. No. | Name | Intermediate | Synthetic method | $^1$H NMR | LCMS Method | LCMS data |
|---|---|---|---|---|---|---|
| 2-19 | Isomer 1: ethyl 2-fluoro-3-(2-oxo-1-oxa-3,8-diazaspiro[4.5]dec-8-yl)-8-azabicyclo[3.2.1]octane-8-carboxylate | 8 and 22 | a | (400 MHz, DMSO-d$_6$) δ: 1.18 (t, J = 7.0 Hz, 3H), 1.36-2.15 (m, 11H), 2.42-2.63 (m, 6H), 4.03 (q, J = 7.0 Hz, 2H), 4.18-4.27 (m, 1H), 4.27-4.39 (m, 1H), 4.56-4.73 (m, 1H), 7.49 (br s, 1H). | E | m/z 356 (M + H)$^+$ (ES+), at 2.32 min, UV inactive |
| 2-19 | Isomer 2: ethyl 2-fluoro-3-(2-oxo-1-oxa-3,8-diazaspiro[4.5]dec-8-yl)-8-azabicyclo[3.2.1]octane-8-carboxylate | 8 and 22 | a | (400 MHz, DMSO-d$_6$) δ: 1.11-1.23 (m, 3H), 1.55-1.90 (m, 11H), 2.43-2.80 (m, 6H), 4.03 (m, 2H), 4.19-4.31 (m, 1H), 4.32-4.44 (m, 1H), 4.72-4.90 (m, 1H), 7.47 (br s, 1H). | E | m/z 356 (M + H)$^+$ (ES+), at 2.03 min, UV inactive |
| 2-20 | Isomer 1: methyl 3-(2-oxo-1,3,8-triazaspiro[4.5]dec-8-yl)-8-azabicyclo[3.2.1]octane-8-carboxylate | 13 and 16 | a | (400 MHz, DMSO-d$_6$) δ: 1.31-1.54 (m, 6 H), 1.55-1.69 (m, 4 H), 1.71-1.90 (m, 2 H), 2.09-2.28 (m, 2 H), 2.50-2.62 (m, 2 H), 2.68-2.83 (m, 1 H), 2.97-3.04 (m, 2 H), 3.52-3.59 (m, 3 H), 4.06-4.16 (m, 2 H), 6.05 (s, 1 H), 6.46 (br. s., 1 H) | B | m/z 323 (M + H)$^+$ (ES+), at 1.81 min, UV inactive |
| 2-20 | Isomer 2: ethyl 2-fluoro-3-(2-oxo-1-oxa-3,8-diazaspiro[4.5]dec-8-yl)-8-azabicyclo[3.2.1]octane-8-carboxylate | 13 and16 | a | (400 MHz, DMSO-d$_6$) δ: 1.52-1.61 (m, 4 H), 1.69-1.84 (m, 6 H), 1.84-1.93 (m, 2 H), 2.13 (d, J = 13.0 Hz, 2 H), 2.17-2.25 (m, 2 H), 2.59-2.71 (m, 1 H), 3.02 (s, 2 H), 3.55 (s, 3 H), 3.94-4.10 (m, 2 H), 6.07 (s, 1 H), 6.45 (br. s., 1 H) | B | m/z 323 (M + H)$^+$ (ES+), at 1.84 min, UV inactive |
| 2-21 | Mixture of isomers: ethyl 3-(2-oxo-1,3,8-triazaspiro[4.5]dec-8-yl)-8-azabicyclo[3.2.1]octane-8-carboxylate | 13 and 17 | a | (400 MHz, CDCl$_3$) δ: 1.21-1.28 (m, 6 H), 1.74-1.87 (m, 2 H), 1.87-2.06 (m, 6 H), 2.46-2.64 (m, 2 H), 2.65-2.81 (m, 2 H), 2.87-3.07 (m, 2 H), 3.33-3.42 (m, 2 H), 3.45-3.63 (m, 2 H), 4.12 (q, J = 7.5 Hz, 2 H), 4.34-4.52 (m, 2 H) | B | m/z 337 (M + H)$^+$ (ES+), at 2.16 min, UV inactive |
| 2-22 | Isomer 1: ethyl 3-(1-benzyl-3-oxo-1,2,8-triazaspiro[4.5]dec-8-yl)-8-azabicyclo[3.2.1]octane-8-carboxylate | 17 and 67 | b | (400 MHz, MeOD-d$_4$) δ: 1.25-1.34 (m, 6 H), 1.54-1.65 (m, 2 H), 1.65-1.70 (m, 1 H), 1.73-2.02 (m, 10 H), 2.40-2.57 (m, 2 H), 2.73-2.86 (m, 2 H), 3.86-3.98 (m, 2 H), 4.15 (q, J = 6.8 Hz, 2 H), 4.29-4.35 (m, 2 H), 7.18-7.44 (m, 5 H) | G | m/z 427 (M + H)$^+$ (ES+), at 5.25 min, UV active |
| 2-23 | Mixture of disteroemers: Ethyl 3-(2-oxo-4-(pyridin-2-ylmethyl)-1-oxa-3,8-diazaspiro[4.5]decan-8-yl)-8-azabicyclo[3.2.1]octane-8-carboxylate | 17 and 82 | g | (400 MHz, CDCl$_3$) δ 1.24-1.28 (m, 3H), 1.59-2.05 (m, 11 H), 2.51-2.69 (m, 2H), 2.79-2.89 (m, 3H), 2.94 (d, J = 7.0 Hz, 2 H), 3.94 (t, J = 7.0 Hz, 1H), 4.13 (q, J = 7.0 Hz, 2H), 4.25-4.41 (m, 2H), 6.05 (s, 1H), 7.13-7.19 (m, 2H), 7.63 (td, J = 7.5, 2.0 Hz, 1H), 8.50 (d, J = 4.0 Hz, 1H) | I | m/z 429 (M + H)$^+$ (ES+), at 3.68 min, UV active |
| 2-24 | Ethyl (3-endo)-3-(2-hydroxy-3-oxo-2,8-diazaspiro[4.5]dec-8-yl)-8-azabicyclo[3.2.1]octane-8-carboxylate | 64 | h | (400 MHz, DMSO-d$_6$) δ: 1.14 (t, J = 7.0 Hz, 3 H), 1.44-1.64 (m, 4 H), 1.75-1.95 (m, 9 H), 2.06 (s, 2 H), 2.14-2.24 (m, 1 H), 2.24-2.46 (m, 3 H), 3.22 (s, 2 H), 3.94-4.08 (m, 4 H), 9.54 (br. s., 1 H) | E | m/z 352 (M + H)$^+$ (ES$^+$), at 1.27 min, UV inactive |
| 2-25 | Isomer 2: ethyl 3-(3-oxo-2-propyl-2,8-diazaspiro[4.5]dec-8-yl)-8-azabicyclo[3.2.1]octane-8-carboxylate | 73 and Example 2-2 | i | (400 MHz, DMSO-d$_6$) δ: 0.80 (t, J = 7.5 Hz, 3 H), 1.17 (t, J = 7.0 Hz, 3 H), 1.37-1.49 (m, 2 H), 1.49-1.62 (m, 4 H), 1.68-1.86 (m, 6 H), 1.86-1.99 (m, 2 H), 2.11 (s, 2 H), 2.18-2.28 (m, 1 H), 2.28-2.48 (m, 3 H), 2.41-2.66 (m, 1H), 3.03-3.19 (m, 4 H), 3.96-4.12 (m, 4 H) | E | m/z 378 (M + H)$^+$ (ES$^+$), at 3.67 min, UV inactive |

TABLE 3-continued

| Ex. No. | Name | Intermediate | Synthetic method | $^1$H NMR | LCMS Method | LCMS data |
|---|---|---|---|---|---|---|
| 2-26 | Isomer 2: ethyl 3-[3-oxo-2-(propan-2-yl)-2,8-diazaspiro[4.5]dec-8-yl]-8-azabicyclo[3.2.1]octane-8-carboxylate | 74 and Example 2-2 | i | (400 MHz, DMSO-d$_6$) δ: 1.03 (d, J = 6.7 Hz, 6 H), 1.17 (t, J = 7.2 Hz, 3 H), 1.45-1.55 (m, 4 H), 1.71-1.86 (m, 6 H), 1.86-2.00 (m, 3 H), 2.09 (s, 2 H), 2.28-2.32 (m, 1 H), 2.30-2.48 (m, 3 H), 2.53-2.59 (m, 1 H), 3.05 (s, 2 H), 3.98-4.10 (m, 4 H) | E | m/z 378 (M + H)$^+$ (ES$^+$), at 3.61 min, UV inactive |
| 2-27 | Isomer 2: ethyl 3-[2-(2-methylpropyl)-3-oxo-2,8-diazaspiro[4.5]dec-8-yl]-8-azabicyclo[3.2.1]octane-8-carboxylate | 75 and Example 2-2 | i | (400 MHz, DMSO-d$_6$) δ: 0.81 (d, J = 6.7 Hz, 6 H), 1.17 (t, J = 7.0 Hz, 3 H), 1.47-1.62 (m, 4 H), 1.72-1.96 (m, 8 H), 2.13 (s, 2 H), 2.19-2.27 (m, 1 H), 2.29-2.48 (m, 3 H), 2.58-2.64 (m, 2 H), 2.95 (d, J = 7.3 Hz, 2 H), 3.11 (s, 2 H), 3.96-4.12 (m, 4 H) | E | m/z 392 (M + H)$^+$ (ES$^+$), at 4.01 min, UV inactive |
| 2-28 | Isomer 2: ethyl 3-[2-(cyclopropylmethyl)-3-oxo-2,8-diazaspiro[4.5]dec-8-yl]-8-azabicyclo[3.2.1]octane-8-carboxylate | 84 and Example 2-2 | i | (400 MHz, DMSO-d$_6$) δ: 0.08-0.22 (m, 2 H), 0.35-0.50 (m, 2 H), 0.79-0.94 (m, 1 H), 1.17 (t, J = 7.0 Hz, 3 H), 1.42-1.66 (m, 4 H), 1.71-1.97 (m, 8 H), 2.04-2.16 (m, 2 H), 2.18-2.28 (m, 1 H), 2.29-2.46 (m, 2 H), 2.53-2.65 (m, 2 H), 3.01 (d, J = 7.0 Hz, 2 H), 3.21 (s, 2 H), 3.94-4.14 (m, 4 H) | E | m/z 390 (M + H)$^+$ (ES$^+$), at 3.78 min, UV inactive |
| 2-29 | Isomer 2: ethyl 3-[2-methoxyethyl)-3-oxo-2,8-diazaspiro[4.5]dec-8-yl]-8-azabicyclo[3.2.1]octane-8-carboxylate | 76 and Example 2-2 | i | (400 MHz, MeOD-d$_4$) δ: 1.27 (t, J = 7.2 Hz, 3 H), 1.55-1.76 (m, 6 H), 1.88 (d, J = 7.9 Hz, 2 H), 1.95 (br. s., 2 H), 2.14-2.32 (m, 4 H), 2.32-2.39 (m, 1 H), 2.49-2.73 (m, 3 H), 3.35 (s, 3 H), 3.42-3.49 (m, 2 H), 3.49-3.56 (m, 2 H), 3.56-3.73 (m, 3 H), 4.06-4.21 (m, 2 H), 4.22-4.36 (m, 2 H) | E | m/z 394 (M + H)$^+$ (ES$^+$), at 3.13 min, UV inactive |
| 2-30 | Isomer 1: (1,1-$^2$H$_2$)ethyl 3-(3-oxo-2,8-diazaspiro[4.5]dec-8-yl)-8-azabicyclo[3.2.1]octane-8-carboxylate | 58 and 60 | j | (400 MHz, DMSO-d$_6$) δ: 1.13 (s, 3 H), 1.34-1.54 (m, 6 H), 1.54-1.71 (m, 4 H), 1.71-1.91 (m, 2 H), 1.94 (s, 2 H), 2.32-2.42 (m, 3 H), 2.51-2.59 (m, 1 H), 2.67-2.79 (m, 1 H), 2.95 (s, 2 H), 4.02-4.19 (m, 2 H), 7.46 (s, 1 H) | E | m/z 338 (M + H)$^+$ (ES$^+$), at 1.76 min, UV inactive |
| 2-30 | Isomer 2: (1,1-$^2$H$_2$)ethyl 3-(3-oxo-2,8-diazaspiro[4.5]dec-8-yl)-8-azabicyclo[3.2.1]octane-8-carboxylate | 58 and 60 | j | (400 MHz, DMSO-d$_6$) δ: 1.13 (s, 3 H), 1.52 (t, J = 5.7 Hz, 5 H), 1.68-1.93 (m, 9 H), 1.96 (s, 2 H), 2.14-2.29 (m, 1 H), 2.34-2.44 (m, 1 H), 2.52-2.61 (m, 1 H), 2.97 (s, 2 H), 4.03 (dt, J = 7.1, 3.7 Hz, 2 H), 7.47 (s, 1 H) | E | m/z 338 (M + H)$^+$ (ES$^+$), at 1.80 min, UV inactive |
| 2-31 | Isomer 1: (2,2,2-$^2$H$_3$)ethyl 3-(3-oxo-2,8-diazaspiro[4.5]dec-8-yl)-8-azabicyclo[3.2.1]octane-8-carboxylate | 58 and 61 | j | (400 MHz, DMSO-d$_6$) δ: 1.33-1.54 (m, 6 H), 1.54-1.72 (m, 4 H), 1.72-1.89 (m, 2 H), 1.94 (s, 2 H), 2.32-2.44 (m, 3 H), 2.51-2.62 (m, 1 H), 2.67-2.84 (m, 1 H), 2.95 (s, 2 H), 4.00 (s, 2 H), 4.04-4.20 (m, 2 H), 7.46 (s, 1 H) | E | m/z 339 (M + H)$^+$ (ES$^+$), at 1.76 min, UV inactive |
| 2-31 | Isomer 2: (2,2,2-$^2$H$_3$)ethyl 3-(3-oxo-2,8-diazaspiro[4.5]dec-8-yl)-8-azabicyclo[3.2.1]octane-8-carboxylate | 58 and 61 | j | (400 MHz, DMSO-d$_6$) δ: 1.52 (t, J = 5.5 Hz, 5 H), 1.69-1.92 (m, 9 H), 1.96 (s, 2 H), 2.13-2.24 (m, 1 H), 2.35-2.44 (m, 1 H), 2.52-2.58 (m, 1 H), 2.97 (s, 2 H), 3.96-4.07 (m, 4 H), 7.47 (s, 1 H) | E | m/z 339 (M + H)$^+$ (ES$^+$), at 1.83 min, UV inactive |
| 2-32 | Isomer 1: ($^2$H$_5$)ethyl 3-(3-oxo-2,8-diazaspiro[4.5]dec-8-yl)-8-azabicyclo[3.2.1]octane-8-carboxylate | 58 and 59 | j | (400 MHz, DMSO-d$_6$) δ: 1.34-1.55 (m, 6 H), 1.56-1.72 (m, 4 H), 1.75-1.89 (m, 2 H), 1.95 (s, 2 H), 2.33-2.42 (m, 3 H), 2.52-2.60 (m, 2 H), 2.68-2.86 (m, 1 H), 2.95 (s, 2 H), 4.03-4.20 (m, 2 H), 7.47 (s, 1 H) | E | m/z 341 (M + H)$^+$ (ES$^+$), at 1.76 min, UV inactive |

TABLE 3-continued

| Ex. No. | Name | Intermediate | Synthetic method | ¹H NMR | LCMS Method | LCMS data |
|---|---|---|---|---|---|---|
| 2-32 | Isomer 2: (²H₅)ethyl 3-(3-oxo-2,8-diazaspiro[4.5]dec-8-yl)-8-azabicyclo[3.2.1]octane-8-carboxylate | 58 and 59 | j | (400 MHz, DMSO-d₆) δ: 1.52 (t, J = 5.5 Hz, 5 H), 1.60-1.92 (m, 9 H), 1.96 (s, 2 H), 2.14-2.27 (m, 1 H), 2.35-2.45 (m, 1 H), 2.56-2.61 (m, 1 H), 2.97 (s, 2 H), 3.96-4.08 (m, 2 H), 7.48 (s, 1 H) | E | m/z 341 (M + H)⁺ (ES⁺), at 1.88 min, UV inactive |
| 2-33 | Isomer 1: propan-2-yl 3-(3-oxo-2,8-diazaspiro[4.5]dec-8-yl)-8-azabicyclo[3.2.1]octane-8-carboxylate | 1 and 68 | b | (400 MHz, DMSO-d₆) δ: 1.14-1.23 (m, 6 H), 1.37-1.57 (m, 6 H), 1.57-1.74 (m, 4 H), 1.74-1.93 (m, 2 H), 1.97 (s, 2 H), 2.36 (d, J = 18.9 Hz, 4 H), 2.76 (dt, J = 11.0, 5.8 Hz, 1 H), 2.98 (s, 2 H), 4.07-4.17 (m, 2 H), 4.78 (dt, J = 12.4, 6.1 Hz, 1 H), 7.49 (s, 1 H) | E | m/z 350 (M + H)⁺ (ES⁺), at 2.97 min, UV inactive |
| 2-33 | Isomer 2: propan-2-yl 3-(3-oxo-2,8-diazaspiro[4.5]dec-8-yl)-8-azabicyclo[3.2.1]octane-8-carboxylate | 1 and 68 | b | (400 MHz, DMSO-d₆) δ: 1.10-1.26 (m, 7 H), 1.44-2.12 (m, 15 H), 2.15-2.46 (m 3 H), 2.98-3.03 (m, 2 H), 3.95-4.20 (m, 2 H), 4.73-4.84 (m, 1 H), 7.54 (br. s., 1 H) | E | m/z 350 (M + H)⁺ (ES⁺), at 3.03 min, UV inactive |
| 2-34 | Isomer 1: S-methyl 3-(3-oxo-2,8-diazaspiro[4.5]dec-8-yl)-8-azabicyclo[3.2.1]octane-8-carbothioate | 1 and 71 | b | (400 MHz, DMSO-d₆) δ: 1.44-1.53 (m, 6 H), 1.61-1.93 (m, 6 H), 1.97 (s, 2 H), 2.25 (s, 3 H), 2.28-2.46 (m, 5 H), 2.73-2.89 (m, 1 H), 2.98 (s, 2 H), 4.09-4.50 (m, 1H), 7.50 (br. s., 1 H) | E | m/z 338 (M + H)⁺ (ES⁺), at 2.53 min, UV inactive |
| 2-34 | Isomer 2: S-methyl 3-(3-oxo-2,8-diazaspiro[4.5]dec-8-yl)-8-azabicyclo[3.2.1]octane-8-carbothioate | 1 and 71 | b | (400 MHz, DMSO-d₆) δ: 1.43-1.63 (m, 4 H), 1.74-2.04 (m, 10 H), 2.17-2.37 (m, 6 H), 2.37-2.49 (m, 2 H), 2.54-2.62 (m, 1 H), 3.00 (s, 2 H), 3.99-4.48 (m, 1 H), 7.51 (br. s., 1 H) | E | m/z 338 (M + H)⁺ (ES⁺), at 2.63 min, UV inactive |
| 2-35 | Isomer 1: S-ethyl 3-(3-oxo-2,8-diazaspiro[4.5]dec-8-yl)-8-azabicyclo[3.2.1]octane-8-carbothioate | 1 and 77 | b | (400 MHz, DMSO-d₆) δ: 1.19 (t, J = 7.3 Hz, 3 H), 1.39-1.58 (m, 6 H), 1.58-1.78 (m, 4 H), 1.78-1.94 (m, 2 H), 1.94-2.03 (m, 2 H), 2.36 (d, J = 19.8 Hz, 4 H), 2.72-2.86 (m, 3 H), 2.97 (s, 2 H), 4.09-4.17 (m, 1 H), 4.33-4.58 (m, 1 H), 7.50 (s, 1 H) | E | m/z 352 (M + H)⁺ (ES⁺), at 2.87 min, UV inactive |
| 2-35 | Isomer 2: S-ethyl 3-(3-oxo-2,8-diazaspiro[4.5]dec-8-yl)-8-azabicyclo[3.2.1]octane-8-carbothioate | 1 and 77 | b | (400 MHz, MeOD-d₄) δ: 1.26-1.32 (m, 3 H), 1.59-1.75 (m, 6 H), 1.75-1.88 (m, 2 H), 1.88-2.10 (m, 4 H), 2.23 (s, 2 H), 2.45-2.56 (m, 2 H), 2.56-2.72 (m, 2 H), 2.79-2.97 (m, 3 H), 3.20 (s, 2 H), 4.22-4.42 (m, 1 H), 4.59-4.73 (m, 2 H) | E | m/z 352 (M + H)⁺ (ES⁺), at 2.96 min, UV inactive |
| 3-1 | Isomer 1: ethyl 5-(3-oxo-2,8-diazaspiro[4.5]dec-8-yl)-2-azabicyclo[2.2.2]octane-2-carboxylate | 1 and 25 | k | (300 MHz, DMSO-d₆) δ: 1.15-1.28 (m, 3 H), 1.44-1.67 (m, 7 H), 1.71 (d, J = 10.1 Hz, 2 H), 1.85-2.02 (m, 1 H), 2.06 (s, 2 H), 2.11-2.25 (m, 2 H), 2.25-2.53 (m, 4 H), 3.06 (s, 2 H), 3.09-3.25 (m, 1 H), 3.43-3.52 (m, 1 H), 3.95 (d, J = 8.2 Hz, 1 H), 4.06 (q, J = 7.1 Hz, 2 H), 7.52 (br. s., 1 H) | E | m/z 336 (M + H)⁺ (ES⁺), at 2.81 min, UV inactive |
| 3-1 | Isomer 2: ethyl 5-(3-oxo-2,8-diazaspiro[4.5]dec-8-yl)-2-azabicyclo[2.2.2]octane-2-carboxylate | 1 and 25 | k | (400 MHz, CDCl₃) δ: 1.21-1.30 (m, 3 H), 1.38-1.49 (m, 2 H), 1.62-1.95 (m, 9 H), 2.05-2.20 (m, 3 H), 2.21 (s, 2 H), 2.26-2.66 (m, 2 H), 3.19 (s, 2 H), 3.25-3.35 (m, 1 H), 3.35-3.48 (m, 1 H), 3.92-4.09 (m, 1 H), 4.13 (q, J = 7.2 Hz, 2 H), 5.69 (br. s., 1 H) | E | m/z 336 (M + H)⁺ (ES⁺), at 2.64 min, UV inactive |

TABLE 3-continued

| Ex. No. | Name | Intermediate | Synthetic method | ¹H NMR | LCMS Method | LCMS data |
|---|---|---|---|---|---|---|
| 3-1 | Isomer 3: ethyl 5-(3-oxo-2,8-diazaspiro[4.5]dec-8-yl)-2-azabicyclo[2.2.2]octane-2-carboxylate | 1 and 25 | k | (400 MHz, CDCl₃) δ: 1.18-1.31 (m, 3 H), 1.40-1.62 (m, 2 H), 1.62-1.76 (m, 8 H), 1.77-1.98 (m, 2 H), 2.09-2.19 (m, 2 H), 2.20 (d, J = 2.3 Hz, 2 H), 2.25-2.69 (m, 2 H), 3.18 (d, J = 3.8 Hz, 2 H), 3.20-3.28 (m, 1 H), 3.55 (d, J = 11.0 Hz, 1 H), 3.96-4.20 (m, 3 H), 5.64 (br. s., 1 H) | E | m/z 336 (M + H)⁺ (ES⁺), at 2.80 min, UV inactive |
| 3-1 | Isomer 4: ethyl 5-(3-oxo-2,8-diazaspiro[4.5]dec-8-yl)-2-azabicyclo[2.2.2]octane-2-carboxylate | 1 and 25 | k | (400 MHz, CDCl₃) δ: 1.20-1.30 (m, 3 H), 1.37-1.51 (m, 2 H), 1.64-1.98 (m, 9 H), 1.99-2.20 (m, 3 H), 2.21 (s, 2 H), 2.33-2.66 (m, 2 H), 3.19 (s, 2 H), 3.24-3.36 (m, 1 H), 3.36-3.47 (m, 1 H), 3.91-4.09 (m, 1 H), 4.13 (q, J = 7.0 Hz, 2 H), 5.69 (br. s., 1 H) | E | m/z 336 (M + H)⁺ (ES⁺), at 2.64 min, UV inactive |
| 3-2 | Isomer 1 (racemic): ethyl 5-(2-oxo-1-oxa-3,8-diazaspiro[4.5]dec-8-yl)-2-azabicyclo[2.2.2]octane-2-carboxylate | 8 and 25 | c | (300 MHz, MeOD-d₄) δ: 1.16-1.32 (m, 3H), 1.40-1.57 (m, 2H), 1.65-2.03 (m, 7H), 2.03-2.24 (m, 2H), 2.24-2.37 (m, 1H), 2.38-2.85 (m, 4H), 3.24-3.50 (m, 4H), 3.94-4.02 (m, 1H), 4.10 (q, J = 7.0 Hz, 2H), NH not observed | C | m/z 338 (M + H)⁺ (ES+), at 1.37 min, UV inactive |
| 3-2 | Isomer 2 (racemic): ethyl 5-(2-oxo-1-oxa-3,8-diazaspiro[4.5]dec-8-yl)-2-azabicyclo[2.2.2]octane-2-carboxylate | 8 and 25 | c | (300 MHz, MeOD-d₄) δ: 1.18-1.31 (m, 3H), 1.51-2.09 (m, 10H), 2.17-2.34 (m, 2H), 2.34-2.57 (m, 2H), 2.58-2.81 (m, 2H), 3.16-3.39 (m, 3H), 3.48-3.63 (m, 1H), 3.98-4.05 (m, 1H), 4.11 (q, J = 7.0 Hz, 2H), NH not observed | C | m/z 338 (M + H)⁺ (ES+), at 1.41 min, UV inactive |
| 3-3 | Isomer 2 (racemic): ethyl 5-(4-ethyl-2-oxo-1-oxa-3,8-diazaspiro[4.5]dec-8-yl)-2-azabicyclo[2.2.2]octane-2-carboxylate | 10 and 25 | l | (300 MHz, CDCl₃) δ: 0.91 (t, J = 7.4 Hz, 3H), 1.08-1.27 (m, 3H), 1.29-1.96 (m, 11H), 2.02-2.36 (m, 4H), 2.71-2.97 (m, 2H), 3.09-3.32 (m, 2H), 3.43-3.58 (m, 1H), 3.88-4.15 (m, 3H), 5.90-6.18 (m, 1H) | E | m/z 366 (M + H)⁺ (ES+), at 3.27 min, UV active |
| 3-4 | Isomer 1 (racemic): ethyl 5-[2-oxo-4-(2,2,2-trifluoroethyl)-1-oxa-3,8-diazaspiro[4.5]dec-8-yl]-2-azabicyclo[2.2.2]octane-2-carboxylate | 25 and 86 | l | (300 MHz, CDCl₃) δ: 1.09-1.28 (m, 4H), 1.28-1.47 (m, 2H), 1.47-2.39 (m, 13H), 2.75-2.96 (m, 2H), 3.17-3.46 (m, 2H), 3.70 (d, J = 9.5 Hz, 1H), 3.84-4.17 (m, 3H), 5.54 (br. s., 1H) | E | m/z 420 (M + H)⁺ (ES+), at 3.41 min, UV active |
| 3-4 | Isomer 2 (racemic): ethyl 5-[2-oxo-4-(2,2,2-trifluoroethyl)-1-oxa-3,8-diazaspiro[4.5]dec-8-yl]-2-azabicyclo[2.2.2]octane-2-carboxylate | 25 and 86 | l | (300 MHz, CDCl₃) δ: 0.80-1.04 (m, 4H), 1.10-1.35 (m, 7H), 1.35-1.98 (m, 6H), 1.98-2.83 (m, 9H), 3.12-3.38 (m, 2H), 3.54 (d, J = 10.5 Hz, 1H), 3.92-4.23 (m, 4H), 7.36 (s, 1H). | E | m/z 420 (M + H)⁺ (ES+), at 3.49 min, UV active |
| 3-5 | Isomer 1 (racemic): ethyl 5-(3-oxo-1-propyl-1,2,8-triazaspiro[4.5]dec-8-yl)-2-azabicyclo[2.2.2]octane-2-carboxylate | 25 and 88 | l | (400 MHz, CDCl₃) δ: 0.73-0.99 (m, 3H), 0.99-1.55 (m, 11H), 1.56-3.05 (m, 13H), 3.11-3.75 (m, 2H), 3.85-4.28 (m, 4H), 7.34 (br. s., 1H) | E | m/z 379 (M + H)⁺ (ES+), at 3.16 min, UV active |
| 3-5 | Isomer 2 (racemic): ethyl 5-(3-oxo-1-propyl-1,2,8-triazaspiro[4.5]dec-8-yl)-2-azabicyclo[2.2.2]octane-2-carboxylate | 25 and 88 | l | (400 MHz, CDCl₃) δ: 0.80-1.04 (m, 4H), 1.10-1.35 (m, 7H), 1.35-1.98 (m, 6H), 1.98-2.83 (m, 9H), 3.12-3.38 (m, 2H), 3.54 (d, J = 10.5 Hz, 1H), 3.92-4.23 (m, 4H), 7.36 (s, 1H). | E | m/z 379 (M + H)⁺ (ES+), at 3.25 min, UV active |

| Ex. No. | Name | Intermediate | Synthetic method | $^1$H NMR | LCMS Method | LCMS data |
|---|---|---|---|---|---|---|
| 4-1 | Isomer 2: ethyl 8-(3-oxo-2,8-diazaspiro[4.5]dec-8-yl)-3-azabicyclo[3.2.1]octane-3-carboxylate | 1 and 27 | a | (300 MHz, DMSO-d$_6$) δ: 1.16 (t, J = 7.0 Hz, 3 H), 1.35-1.49 (m, 2 H), 1.56 (t, J = 5.0 Hz, 4 H), 1.61-1.75 (m, 2 H), 2.01 (s, 2 H), 2.05-2.13 (m, 1 H), 2.13-2.42 (m, 6 H), 3.01 (s, 2 H), 3.05-3.26 (m, 2 H), 3.36-3.49 (m, 2 H), 4.00 (q, J = 7.0 Hz, 2 H), 7.48 (br. s., 1 H) | E | m/z 336 (M + H)$^+$ (ES+), at 3.11 min, UV inactive |
| 5-1 | Isomer 1: ethyl 3-(3-oxo-2,8-diazaspiro[4.5]dec-8-yl)-9-azabicyclo[3.3.1]nonane-9-carboxylate | 1 and 28 | e | (400 MHz, CDCl$_3$) δ: 1.15-2.08 (m, 16 H), 2.11-2.87 (m, 8 H), 3.18 (s, 2 H), 4.03-4.24 (m, 2 H), 4.35-4.66 (m, 2 H), 5.78 (br. s., 1 H) | D | m/z 350 (M + H)$^+$ (ES+), at 2.75 min, UV inactive |
| 5-1 | Isomer 2: ethyl 3-(3-oxo-2,8-diazaspiro[4.5]dec-8-yl)-9-azabicyclo[3.3.1]nonane-9-carboxylate | 1 and 28 | e | (400 MHz, CDCl$_3$) δ: 1.25 (t, J = 7.0 Hz, 3 H), 1.51-2.01 (m, 14 H), 2.20 (s, 2 H), 2.30-2.80 (m, 4 H), 3.04-3.34 (m, 3 H), 4.12 (q, J = 7.0 Hz, 2 H), 4.29-4.54 (m, 2 H), 5.87 (br. s., 1 H) | D | m/z 350 (M + H)$^+$ (ES+), at 2.7 min, UV inactive |
| 5-2 | Isomer 1: prop-2-yn-1-yl 3-(3-oxo-2,8-diazaspiro[4.5]dec-8-yl)-9-azabicyclo[3.3.1]nonane-9-carboxylate | 1 and 30 | d | (400 MHz, CDCl$_3$) δ: 1.24-1.49 (m, 5 H), 1.49-1.74 (m, 7 H), 1.80-1.98 (m, 1 H), 2.13-2.37 (m, 5 H), 2.41-2.66 (m, 4 H), 3.16 (s, 2 H), 4.40-4.57 (m, 2 H), 4.68 (s, 2 H), 5.80 (br. s., 1 H) | D | m/z 360 (M + H)$^+$ (ES+), at 2.08 min, UV inactive |
| 5-2 | Isomer 2: prop-2-yn-1-yl 3-(3-oxo-2,8-diazaspiro[4.5]dec-8-yl)-9-azabicyclo[3.3.1]nonane-9-carboxylate | 1 and 30 | d | (400 MHz, CDCl$_3$) δ: 1.54-1.92 (m, 14 H), 2.18 (s, 2 H), 2.34-2.51 (m, 3 H), 2.51-2.66 (m, 2 H), 3.10-3.24 (m, 3 H), 4.33-4.47 (m, 2 H), 4.63-4.73 (m, 2 H), 5.88 (s, 1 H) | D | m/z 360 (M + H)$^+$ (ES+), at 2.10 min, UV inactive |
| 5-3 | Mixture of isomers: but-2-yn-1-yl 3-(3-oxo-2,8-diazaspiro[4.5]dec-8-yl)-9-azabicyclo[3.3.1]nonane-9-carboxylate | 1 and 31 | d | (400 MHz, CDCl$_3$) δ: 1.11-1.96 (m, 16 H), 2.06-2.72 (m, 7 H), 3.15 (s, 3 H), 4.26-4.71 (m, 4 H), 6.29 (s, 1 H) | D | m/z 374 (M + H)$^+$ (ES+), at 2.26 min, UV inactive |
| 5-4 | Isomer 1: ethyl 3-(2-oxo-1-oxa-3,8-diazaspiro[4.5]dec-8-yl)-9-azabicyclo[3.3.1]nonane-9-carboxylate | 8 and 28 | e | (400 MHz, CDCl$_3$) δ: 0.97-2.14 (m, 16 H), 2.14-3.08 (m, 6 H), 3.21-3.53 (m, 2 H), 3.97-4.22 (m, 2 H), 4.33-4.68 (m, 2 H), 5.07 (br. s., 1 H) | D | m/z 352 (M + H)$^+$ (ES+), at 2.15 min, UV inactive |
| 5-4 | Isomer 2: ethyl 3-(2-oxo-1-oxa-3,8-diazaspiro[4.5]dec-8-yl)-9-azabicyclo[3.3.1]nonane-9-carboxylate | 8 and 28 | e | (400 MHz, CDCl$_3$) δ: 0.70-2.41 (m, 19 H), 2.64-2.92 (m, 3 H), 3.35 (s, 2 H), 3.99-4.19 (m, 2 H), 4.29-4.50 (m, 2 H), 5.13 (br. s., 1 H) | D | m/z 352 (M + H)$^+$ (ES+), at 2.23 min, UV inactive |
| 6-1 | Isomer 1: methyl 3-(3-oxo-2,8-diazaspiro[4.5]dec-8-yl)-6-azabicyclo[3.2.1]octane-6-carboxylate | 1 and 33 | a | (400 MHz, DMSO-d$_6$) δ: 1.23-1.37 (m, 1 H), 1.37-1.57 (m, 5 H), 1.64-1.82 (m, 2 H), 1.88-2.04 (m, 1 H), 1.98 (s, 2 H), 2.30-2.48 (m, 5 H), 2.99 (s, 2 H), 3.08-3.20 (m, 2 H), 3.22-3.33 (m, 2 H), 3.58 (s, 3 H), 3.99-4.07 (m, 1 H), 7.51 (br s, 1 H) | E | m/z 322 (M + H)$^+$ (ES+), at 1.99 min, UV inactive |
| 6-1 | Isomer 2: methyl 3-(3-oxo-2,8-diazaspiro[4.5]dec-8-yl)-6-azabicyclo[3.2.1]octane-6-carboxylate | 1 and 33 | a | (400 MHz, DMSO-d$_6$) δ: 1.44-1.55 (m, 3 H), 1.56-1.76 (m, 5 H), 1.82-1.93 (m, 1 H), 1.98 (s, 2 H), 2.30-2.46 (m, 5 H), 2.99 (s, 2 H), 3.08-3.36 (m, 4 H), 3.58 (s, 3 H), 3.87-3.95 (m, 1 H), 7.51 (br s, 1 H). | E | m/z 322 (M + H)$^+$ (ES+), at 2.12 min, UV inactive |

TABLE 3-continued

| Ex. No. | Name | Intermediate | Synthetic method | $^1$H NMR | LCMS Method | LCMS data |
|---|---|---|---|---|---|---|
| 6-2 | Isomer 2: ethyl 3-(3-oxo-2,8-diazaspiro[4.5]dec-8-yl)-6-azabicyclo[3.2.1]octane-6-carboxylate | 1 and 34 | a | (400 MHz, DMSO-d$_6$) δ: 1.06-1.27 (m, 3 H), 1.35-1.75 (m, 7 H), 1.77-1.88 (m, 1 H), 1.88-2.04 (m, 3 H), 2.09-2.70 (m, 6 H), 2.94 (s, 2 H), 3.04-3.19 (m, 1 H), 3.25-3.39 (m, 2 H), 3.82-4.11 (m, 3 H), 7.46 (s, 1 H) | E | m/z 336 (M + H)$^+$ (ES+), at 2.37 min, UV inactive |
| 6-3 | Isomer 1: ethyl 3-(2-oxo-1-oxa-3,8-diazaspiro[4.5]dec-8-yl)-6-azabicyclo[3.2.1]octane-6-carboxylate | 8 and 34 | a | (400 MHz, DMSO-d$_6$) δ: 1.07-1.21 (m, 3 H) 1.21-1.53 (m, 2 H), 1.57-1.83 (m, 6 H), 1.86-2.01 (m, 1 H), 2.25-2.55 (m, 6 H), 3.02-3.43 (m, 5 H), 3.87-4.10 (m, 3 H), 7.43 (s, 1 H) | E | m/z 338 (M + H)$^+$ (ES+), at 2.34 min, UV inactive |
| 6-3 | Isomer 2: ethyl 3-(2-oxo-1-oxa-3,8-diazaspiro[4.5]dec-8-yl)-6-azabicyclo[3.2.1]octane-6-carboxylate | 8 and 34 | a | (400 MHz, DMSO-d$_6$) δ: 1.05-1.32 (m, 4 H) 1.50-2.06 (m, 8 H), 2.21-2.70 (m, 6 H), 3.02-3.48 (m, 5 H), 3.81-4.10 (m, 3 H), 7.43 (br. s., 1 H) | E | m/z 338 (M + H)$^+$ (ES+), at 2.50 min, UV inactive |
| 7-1 | Isomer 1: ethyl 6-(2-oxo-1-oxa-3,8-diazaspiro[4.5]dec-8-yl)-3-azabicyclo[3.2.1]octane-3-carboxylate | 8 and 35 | f | (400 MHz, DMSO-d$_6$) δ: 1.07-1.27 (m, 5 H), 1.57-1.82 (m, 4H), 1.96-2.12 (m, 2 H), 2.33-2.45 (m, 3 H), 2.52-2.61 (m, 2 H), 3.07-3.22 (m, 4 H), 3.35-3.41 (m, 4 H), 3.98 (q, J = 7.0 Hz, 2 H), 7.44 (s, 1 H) | E | m/z 338 (M + H)$^+$ (ES+), at 2.52 min, UV inactive |
| 8-1 | Isomer 1: ethyl 6-(3-oxo-2,8-diazaspiro[4.5]dec-8-yl)-3-azabicyclo[3.1.1]heptane-3-carboxylate | 1 and 63 | m | (400 MHz, CDCl$_3$) δ: 1.26 (t, J = 7.2 Hz, 3 H), 1.31-1.47 (m, 1 H), 1.55-1.90 (m, 4 H), 2.21 (s, 3 H), 2.27-2.70 (m, 7 H), 3.19 (s, 2 H), 3.50 (d, J = 10.9 Hz, 2 H), 3.71 (t, J = 10.9 Hz, 2 H), 4.15 (q, J = 7.0 Hz, 2 H), 5.89 (br. s., 1 H) | E | m/z 322 (M + H)$^+$ (ES+), at 2.43 min, UV inactive |
| 9-1 | Isomer 1: ethyl 3-(3-oxo-2,8-diazaspiro[4.6]undec-8-yl)-8-azabicyclo[3.2.1]octane-8-carboxylate | 17 and 66 | n | (400 MHz, DMSO-d$_6$) δ: 1.15 (t, J = 7.0 Hz, 3 H), 1.37-1.74 (m, 13 H), 1.73-1.89 (m, 2 H), 1.97 (s, 2 H), 2.32-2.48 (m, 1H), 2.52-2.60 (m, 2 H), 2.96 (s, 2 H), 2.98-3.11 (m, 1 H), 3.92-4.07 (m, 2 H), 4.12 (br. s., 2 H), 7.43 (s, 1 H) | E | m/z 350 (M + H)$^+$ (ES+), at 2.84 min, UV inactive |
| 9-1 | Isomer 2: ethyl 3-(3-oxo-2,8-diazaspiro[4.6]undec-8-yl)-8-azabicyclo[3.2.1]octane-8-carboxylate | 17 and 66 | n | (400 MHz, DMSO-d$_6$) δ: 1.14 (t, J = 7.0 Hz, 3 H), 1.45-1.66 (m, 9 H), 1.71-1.85 (m, 4 H), 1.86-1.96 (m, 2 H), 1.98 (d, J = 2.7 Hz, 2 H), 2.40-2.45 (m, 1 H), 2.52-2.60 (m, 3 H), 2.97 (s, 2 H), 3.93-4.03 (m, 2 H), 4.03-4.11 (m, 2 H), 7.43 (s, 1 H) | E | m/z 350 (M + H)$^+$ (ES+), at 2.81 min, UV inactive |
| 9-2 | Isomer 1: ethyl 3-(2-oxo-1-oxa-3,8-diazaspiro[4.6]undec-8-yl)-8-azabicyclo[3.2.1]octane-8-carboxylate | 17 and 80 | o | $^1$H NMR (400 MHz, DMSO-d$_6$) δ: 1.17 (t, J = 7.0 Hz, 3 H), 1.34-1.54 (m, 3 H), 1.54-1.72 (m, 5 H), 1.72-1.92 (m, 6 H), 2.39-2.47 (m, 1 H), 2.54-2.57 (m, 1H), 2.60 (t, J = 5.8 Hz, 2 H), 2.93-3.08 (m, 1 H), 3.20 (s, 2 H), 3.95-4.10 (m, 2 H), 4.10-4.16 (m, 2 H), 7.41 (s, 1 H) | E | m/z 352 (M + H)$^+$ (ES+), at 2.96 min, UV inactive |

TABLE 3-continued

| Ex. No. | Name | Intermediate | Synthetic method | ¹H NMR | LCMS Method | LCMS data |
|---|---|---|---|---|---|---|
| 9-2 | Isomer 2: ethyl 3-(2-oxo-1-oxa-3,8-diazaspiro[4.6]undec-8-yl)-8-azabicyclo[3.2.1]octane-8-carboxylate | 17 and 80 | o | ¹H NMR (400 MHz, DMSO-d₆) δ: 1.17 (t, J = 7.0 Hz, 3 H), 1.36-1.54 (m, 3 H), 1.57-1.72 (m, 5 H), 1.72-1.93 (m, 6 H), 2.38-2.46 (m, 1 H), 2.53-2.57 (m, 1 H), 2.57-2.64 (m, 2 H), 2.94-3.07 (m, 1 H), 3.20 (s, 2 H), 4.04 (t, J = 7.2 Hz, 2 H), 4.09-4.19 (m, 2 H), 7.40 (s, 1 H) | E | m/z 352 (M + H)⁺ (ES⁺), at 2.96 min, UV inactive |
| 9-2 | Isomer 3: ethyl 3-(2-oxo-1-oxa-3,8-diazaspiro[4.6]undec-8-yl)-8-azabicyclo[3.2.1]octane-8-carboxylate | 17 and 80 | o | ¹H NMR (400 MHz, DMSO-d₆) δ: 1.17 (t, J = 7.0 Hz, 3 H), 1.46-1.64 (m, 3 H), 1.67-1.79 (m, 2 H), 1.79-2.04 (m, 9 H), 2.42-2.48 (m, 2 H), 2.64-2.75 (m, 3 H), 3.22 (s, 2 H), 3.97-4.06 (m, 2 H), 4.07-4.15 (m, 2 H), 7.43 (s, 1 H) | E | m/z 352 (M + H)⁺ (ES⁺), at 3.03 min, UV inactive |
| 9-2 | Isomer 4: ethyl 3-(2-oxo-1-oxa-3,8-diazaspiro[4.6]undec-8-yl)-8-azabicyclo[3.2.1]octane-8-carboxylate | 17 and 80 | o | ¹H NMR (400 MHz, DMSO-d₆) δ: 1.17 (t, J = 7.0 Hz, 3 H), 1.49-1.66 (m, 3 H), 1.66-1.88 (m, 9 H), 1.88-2.00 (m, 2 H), 2.42-2.47 (m, 1 H), 2.55-2.67 (m, 2H), 2.68-2.75 (m, 2 H), 3.22 (s, 2 H), 3.98-4.08 (m, 2 H), 4.09-4.16 (m, 2 H), 7.43 (s, 1 H) | E | m/z 352 (M + H)⁺ (ES⁺), at 3.04 min, UV inactive |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen,* 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader.

$pEC_{50}$ and $E_{max}$ figures were calculated from the resulting data for each receptor subtype.

For most examples two diastereomers exist which have been separated, unless stated otherwise, Analytical data for active isomers is reported in Table 3. In examples 3-1 and 9-2 the four enantiomers have been separated, data is provided for all isomers.

The results are set out in Table 4 below.

TABLE 4

| | Muscarinic Activity | | | |
|---|---|---|---|---|
| Ex. No. | $pEC_{50}$ $M_1$ (% Emax cf. ACh) | $pEC_{50}$ $M_2$ (% Emax cf. ACh) | $pEC_{50}$ $M_3$ (% Emax cf. ACh) | $pEC_{50}$ $M_4$ (% Emax cf. ACh) |
| ACh | 8.3 (102) | 7.8 (105) | 8.1 (115) | 8.1 (110) |
| 2-1 Isomer 2 | 6.2 (72) | NT | NT | 5.8 (25) |
| 2-2 Isomer 1 | 7.1 (99) | <4.7 (0) | <4.7 (17) | 6.7 (53) |
| 2-2 Isomer 2 | 7.9 (86) | <4.7 (0) | <4.7 (0) | 7.6 (31) |
| 2-3 Isomer 1 | 6.4 (85) | NT | NT | 5.7 (47) |
| 2-3 Isomer 2 | 7.1 (49) | <4.7 (4) | <4.7 (0) | <4.7 (16) |
| 2-4 Isomer 1 | 7.0 (92) | <4.7 (27) | <4.7 (7) | 6.9 (64) |
| 2-4 Isomer 2 | 7.7 (86) | <4.7 (8) | <4.7 (0) | 7.6 (53) |
| 2-5 Isomer 1 | 7.6 (98) | 6.8 (39) | <4.7 (7) | 7.6 (87) |
| 2-6 Isomer 2 | 6.3 (35) | NT | NT | 4.8 (32) |
| 2-8 Isomer 1 | 7.7 (52) | <4.7 (4) | 4.9 (50) | <4.7 (23) |
| 2-8 Isomer 2 | 7.0 (89) | <4.7 (6) | <4.7 (12) | 7.5 (59) |
| 2-9 Isomer 1 | 8.3 (91) | <4.7 (2) | <4.7 (22) | 8.6 (78) |
| 2-10 Isomer 1 | 7.7 (74) | <4.7 (1) | <4.7 (5) | 7.1 (21) |
| 2-10 Isomer 2 | 7.2 (77) | <4.7 (11) | <4.7 (13) | 6.9 (50) |
| 2-11 Isomer 1 | 6.2 (95) | NT | NT | 6.0 (53) |
| 2-11 Isomer 2 | 6.6 (101) | <4.7 (18) | <4.7 (22) | 6.7 (55) |
| 2-13 Isomer 2 | 6.8 (76) | <4.7 (11) | <4.7 (57) | 7.0 (49) |
| 2-14 Isomer 1 | 6.7 (108) | NT | NT | 6.3 (55) |
| 2-14 Isomer 2 | 7.4 (92) | <4.7 (0) | <4.7 (0) | 7.1 (60) |
| 2-15 Isomer 1 | 7.0 (101) | NT | NT | <4.7 (10) |
| 2-16 Isomer 1 | 7.3 (36) | <4.7 (3) | <4.7 (9) | 7.1 (19) |
| 2-16 Isomer 2 | 6.2 (68) | NT | NT | 6.7 (51) |
| 2-17 Isomer 1 | 7.5 (58) | <4.7 (2) | <4.7 (51) | 7.7 (25) |
| 2-17 Isomer 2 | 6.7 (117) | <4.7 (3) | <4.7 (12) | 7.0 (72) |
| 2-18 Isomer 1 | 6.6 (55) | NT | NT | <4.7 (11) |
| 2-19 Isomer 2 | 6.0 (94) | NT | NT | 5.4 (74) |
| Mixture of distereomers 2-23 | 6.3 (86) | NT | NT | <4.7 (12) |
| 2-24 | 7.2 (88) | <4.7 (4) | <4.7 (4) | <4.7 (29) |
| 2-25 Isomer 2 | 6.6 (53) | <4.7 (15) | <4.7 (12) | 6.6 (25) |
| 2-26 Isomer 2 | 6.2 (43) | NT | NT | 6.2 (22) |
| 2-27 Isomer 2 | 6.4 (38) | NT | NT | <4.7 (14) |
| 2-28 Isomer 2 | 6.3 (57) | NT | NT | 6.5 (27) |
| 2-30 Isomer 1 | 6.9 (107) | NT | NT | 6.7 (49) |
| 2-30 Isomer 2 | 7.5 (66) | <4.7 (9) | <4.7 (16) | 7.1 (29) |
| 2-31 Isomer 1 | 6.9 (112) | NT | NT | 6.6 (53) |
| 2-31 Isomer 2 | 7.6 (76) | <4.7 (11) | <4.7 (8) | 7.6 (26) |
| 2-32 Isomer 1 | 7.1 (92) | <4.7 (16) | <4.7 (10) | 6.9 (40) |
| 2-32 Isomer 2 | 7.5 (77) | <4.7 (15) | <4.7 (1) | 7.3 (48) |
| 2-33 Isomer 1 | 7.5 (37) | NT | NT | 6.7 (20) |
| 2-33 Isomer 2 | 6.4 (62) | NT | NT | 6.5 (25) |
| 2-34 Isomer 1 | 6.3 (50) | NT | NT | <4.7 (8) |
| 2-35 Isomer 1 | 7.4 (24) | NT | NT | <4.7 (7) |
| 2-35 Isomer 2 | 6.1 (50) | NT | NT | <4.7 (10) |
| 3-1 Isomer 1 | 8.9 (111) | 8.0 (63) | <4.7 (6) | 8.4 (61) |
| 3-1 Isomer 2 | 7.2 (94) | <4.7 (11) | <4.7 (1) | 6.6 (31) |
| 3-1 Isomer 3 | 7.4 (101) | <4.7 (17) | <4.7 (16) | 6.8 (41) |
| 3-1 Isomer 4 | 5.9 (62) | NT | NT | <4.7 (7) |
| 3-2 Isomer 1 | 6.6 (111) | NT | NT | 5.9 (29) |
| 3-2 Isomer 2 | 7.0 (127) | NT | NT | 6.4 (36) |
| 3-3 Isomer 2 | 6.1 (76) | NT | NT | 6.5 (56) |
| 4-1 Isomer 2 | 6.3 (36) | NT | NT | <4.7 (3) |
| 5-1 Isomer 1 | 6.5 (131) | 5.1 (17) | <4.7 (8) | 6.6 (25) |

TABLE 4-continued

| Ex. No. | pEC$_{50}$ M$_1$ (% Emax cf. ACh) | pEC$_{50}$ M$_2$ (% Emax cf. ACh) | pEC$_{50}$ M$_3$ (% Emax cf. ACh) | pEC$_{50}$ M$_4$ (% Emax cf. ACh) |
|---|---|---|---|---|
| 5-1 Isomer 2 | 6.8 (77) | <4.7 (14) | <4.7 (6) | <4.7 (8) |
| 5-2 Isomer 1 | 7.0 (78) | <4.7 (3) | <4.7 (9) | 7.1 (37) |
| 5-2 Isomer 2 | 7.0 (48) | <4.7 (3) | <4.7 (4) | 7.2 (20) |
| 5-3 Mixture of isomers | 7.5 (80) | <4.7 (7) | 5.2 (19) | 7.5 (37) |
| 5-4 Isomer 1 | 6.4 (76) | NT | NT | <4.7 (39) |
| 5-4 Isomer 2 | 6.8 (72) | <4.7 (2) | <4.7 (0) | <4.7 (8) |
| 6-1 Isomer 1 | 5.6 (78) | NT | NT | <4.7 (53) |
| 6-1 Isomer 2 | 7.7 (104) | <4.7 (18) | <4.7 (5) | 7.2 (33) |
| 6-2 Isomer 2 | 8.7 (118) | 7.8 (30) | <4.7 (18) | 8.4 (78) |
| 6-3 Isomer 2 | 7.6 (112) | 5.9 (24) | <4.7 (48) | 7.4 (81) |
| 7-1 Isomer 1 | 7.4 (46) | <4.7 (1) | <4.7 (2) | <4.7 (5) |
| 9-1 Isomer 2 | 8.4 (103) | <4.7 (12) | <4.7 (22) | 8.6 (60) |
| 9-2 Isomer 1 | <4.7 (23) | NT | NT | <4.7 (13) |
| 9-2 Isomer 2 | <4.7 (18) | NT | NT | <4.7 (8) |
| 9-2 Isomer 3 | 6.3 (113) | NT | NT | 7.1 (81) |
| 9-2 Isomer 4 | 8.0 (103) | NT | NT | 8.3 (66) |

NT—not tested

Example B

Passive Avoidance

Studies were carried out as described previously by Foley et al., (2004) *Neuropsychopharmacology*. In the passive avoidance task scopolamine administration (1 mg/kg, i.p.) at 6 hours following training rendered animals amnesic of the paradigm. A dose range of 3, 10, and 30 mg/kg (po) free base, administered 90 minutes prior to the training period via oral gavage, was examined.

Example 2-2 Isomer 1 was found to reverse scopolamine-induced amnesia of the paradigm in a dose-dependent manner, with an approximate ED$_{50}$ of ca. 10 mg/kg (po). The effect of 30 mg/kg was similar to that produced by the cholinesterase inhibitor donepezil (0.1 mg/kg, ip) which served as a positive control (FIG. 1).

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound which is selected from the group consisting of:
   ethyl 5-(2-oxo-1-oxa-3,8-diazaspiro[4.5]dec-8-yl)-2-azabicyclo[2.2.1]heptane-2-carboxylate;
   methyl 3-(3-oxo-2,8-diazaspiro[4.5]dec-8-yl)-8-azabicyclo[3.2.1]octane-8-carboxylate;
   ethyl 3-(3-oxo-2,8-diazaspiro[4.5]dec-8-yl)-8-azabicyclo[3.2.1]octane-8-carboxylate;
   2-fluoroethyl 3-(3-oxo-2,8-diazaspiro[4.5]dec-8-yl)-8-azabicyclo[3.2.1]octane-8-carboxylate;
   prop-2-yn-1-yl 3-(3-oxo-2,8-diazaspiro[4.5]dec-8-yl)-8-azabicyclo[3.2.1]octane-8-carboxylate;
   but-2-yn-1-yl 3-(3-oxo-2,8-diazaspiro[4.5]dec-8-yl)-8-azabicyclo[3.2.1]octane-8-carboxylate;
   8-(8-butanoyl-8-azabicyclo[3.2.1]oct-3-yl)-2,8-diazaspiro[4.5]decan-3-one;
   ethyl 3-(1-methyl-3-oxo-2,8-diazaspiro[4.5]dec-8-yl)-8-azabicyclo[3.2.1]octane-8-carboxylate;
   ethyl 3-(1-ethyl-3-oxo-2,8-diazaspiro[4.5]dec-8-yl)-8-azabicyclo[3.2.1]octane-8-carboxylate;
   ethyl 3-(3-oxo-1-propyl-2,8-diazaspiro[4.5]dec-8-yl)-8-azabicyclo[3.2.1]octane-8-carboxylate;
   ethyl 3-(1-benzyl-3-oxo-2,8-diazaspiro[4.5]dec-8-yl)-8-azabicyclo[3.2.1]octane-8-carboxylate;
   ethyl 2-fluoro-3-(3-oxo-2,8-diazaspiro[4.5]dec-8-yl)-8-azabicyclo[3.2.1]octane-8-carboxylate;
   ethyl 3-(6-fluoro-3-oxo-2,8-diazaspiro[4.5]dec-8-yl)-8-azabicyclo[3.2.1]octane-8-carboxylate;
   ethyl 3-(2-ethyl-3-oxo-2,8-diazaspiro[4.5]dec-8-yl)-8-azabicyclo[3.2.1]octane-8-carboxylate;
   ethyl 3-(2-oxo-1-oxa-3,8-diazaspiro[4.5]dec-8-yl)-8-azabicyclo[3.2.1]octane-8-carboxylate;
   ethyl 3-(4-methyl-2-oxo-1-oxa-3,8-diazaspiro[4.5]dec-8-yl)-8-azabicyclo[3.2.1]octane-8-carboxylate;
   ethyl 3-(4-ethyl-2-oxo-1-oxa-3,8-diazaspiro[4.5]dec-8-yl)-8-azabicyclo[3.2.1]octane-8-carboxylate;
   ethyl 3-[2-oxo-4-(propan-2-yl)-1-oxa-3,8-diazaspiro[4.5]dec-8-yl]-8-azabicyclo[3.2.1]octane-8-carboxylate;
   ethyl 3-(4,4-dimethyl-2-oxo-1-oxa-3,8-diazaspiro[4.5]dec-8-yl)-8-azabicyclo[3.2.1]octane-8-carboxylate;
   ethyl 2-fluoro-3-(2-oxo-1-oxa-3,8-diazaspiro[4.5]dec-8-yl)-8-azabicyclo[3.2.1]octane-8-carboxylate;
   methyl 3-(2-oxo-1,3,8-triazaspiro[4.5]dec-8-yl)-8-azabicyclo[3.2.1]octane-8-carboxylate;
   ethyl 3-(2-oxo-1,3,8-triazaspiro[4.5]dec-8-yl)-8-azabicyclo[3.2.1]octane-8-carboxylate;
   ethyl 3-(1-benzyl-3-oxo-1,2,8-triazaspiro[4.5]dec-8-yl)-8-azabicyclo[3.2.1]octane-8-carboxylate;
   Ethyl 3-(2-oxo-4-(pyridin-2-ylmethyl)-1-oxa-3,8-diazaspiro[4.5]decan-8-yl)-8-azabicyclo[3.2.1]octane-8-carboxylate;
   Ethyl (3-endo)-3-(2-hydroxy-3-oxo-2,8-diazaspiro[4.5]dec-8-yl)-8-azabicyclo[3.2.1]octane-8-carboxylate;
   ethyl 3-(3-oxo-2-propyl-2,8-diazaspiro[4.5]dec-8-yl)-8-azabicyclo[3.2.1]octane-8-carboxylate;
   ethyl 3-[3-oxo-2-(propan-2-yl)-2,8-diazaspiro[4.5]dec-8-yl]-8-azabicyclo[3.2.1]octane-8-carboxylate;

ethyl 3-[2-(2-methylpropyl)-3-oxo-2,8-diazaspiro[4.5]dec-8-yl]-8-azabicyclo[3.2.1]octane-8-carboxylate;
ethyl 3-[2-(cyclopropylmethyl)-3-oxo-2,8-diazaspiro[4.5]dec-8-yl]-8-azabicyclo[3.2.1]octane-8-carboxylate;
ethyl 3-[2-(2-methoxyethyl)-3-oxo-2,8-diazaspiro[4.5]dec-8-yl]-8-azabicyclo[3.2.1]octane-8-carboxylate;
(1,1-$^2H_2$)ethyl 3-(3-oxo-2,8-diazaspiro[4.5]dec-8-yl)-8-azabicyclo[3.2.1]octane-8-carboxylate;
(2,2,2-$^2H_3$)ethyl 3-(3-oxo-2,8-diazaspiro[4.5]dec-8-yl)-8-azabicyclo[3.2.1]octane-8-carboxylate;
($^2H_5$)ethyl 3-(3-oxo-2,8-diazaspiro[4.5]dec-8-yl)-8-azabicyclo[3.2.1]octane-8-carboxylate;
propan-2-yl 3-(3-oxo-2,8-diazaspiro[4.5]dec-8-yl)-8-azabicyclo[3.2.1]octane-8-carboxylate;
S-methyl 3-(3-oxo-2,8-diazaspiro[4.5]dec-8-yl)-8-azabicyclo[3.2.1]octane-8-carbothioate;
S-ethyl 3-(3-oxo-2,8-diazaspiro[4.5]dec-8-yl)-8-azabicyclo[3.2.1]octane-8-carbothioate;
ethyl 5-(3-oxo-2,8-diazaspiro[4.5]dec-8-yl)-2-azabicyclo[2.2.2]octane-2-carboxylate;
ethyl 5-(2-oxo-1-oxa-3,8-diazaspiro[4.5]dec-8-yl)-2-azabicyclo[2.2.2]octane-2-carboxylate;
ethyl 5-(4-ethyl-2-oxo-1-oxa-3,8-diazaspiro[4.5]dec-8-yl)-2-azabicyclo[2.2.2]octane-2-carboxylate;
ethyl 5-[2-oxo-4-(2,2,2-trifluoroethyl)-1-oxa-3,8-diazaspiro[4.5]dec-8-yl]-2-azabicyclo[2.2.2]octane-2-carboxylate;
ethyl 5-(3-oxo-1-propyl-1,2,8-triazaspiro[4.5]dec-8-yl)-2-azabicyclo[2.2.2]octane-2-carboxylate;
ethyl 8-(3-oxo-2,8-diazaspiro[4.5]dec-8-yl)-3-azabicyclo[3.2.1]octane-3-carboxylate;
ethyl 3-(3-oxo-2,8-diazaspiro[4.5]dec-8-yl)-9-azabicyclo[3.3.1]nonane-9-carboxylate;
prop-2-yn-1-yl 3-(3-oxo-2,8-diazaspiro[4.5]dec-8-yl)-9-azabicyclo[3.3.1]nonane-9-carboxylate;
but-2-yn-1-yl 3-(3-oxo-2,8-diazaspiro[4.5]dec-8-yl)-9-azabicyclo[3.3.1]nonane-9-carboxylate;
ethyl 3-(2-oxo-1-oxa-3,8-diazaspiro[4.5]dec-8-yl)-9-azabicyclo[3.3.1]nonane-9-carboxylate;
methyl 3-(3-oxo-2,8-diazaspiro[4.5]dec-8-yl)-6-azabicyclo[3.2.1]octane-6-carboxylate;
ethyl 3-(3-oxo-2,8-diazaspiro[4.5]dec-8-yl)-6-azabicyclo[3.2.1]octane-6-carboxylate;
ethyl 3-(2-oxo-1-oxa-3,8-diazaspiro[4.5]dec-8-yl)-6-azabicyclo[3.2.1]octane-6-carboxylate;
ethyl 6-(2-oxo-1-oxa-3,8-diazaspiro[4.5]dec-8-yl)-3-azabicyclo[3.2.1]octane-3-carboxylate;
ethyl 6-(3-oxo-2,8-diazaspiro[4.5]dec-8-yl)-3-azabicyclo[3.1.1]heptane-3-carboxylate;
ethyl 3-(3-oxo-2,8-diazaspiro[4.6]undec-8-yl)-8-azabicyclo[3.2.1]octane-8-carboxylate;
ethyl 3-(2-oxo-1-oxa-3,8-diazaspiro[4.6]undec-8-yl)-8-azabicyclo[3.2.1]octane-8-carboxylate;
or a salt thereof.

2. The compound according to claim 1 which is selected from the group consisting of:
ethyl 3-(2-oxo-1-oxa-3,8-diazaspiro[4.5]dec-8-yl)-8-azabicyclo[3.2.1]octane-8-carboxylate;
ethyl 3-(4-methyl-2-oxo-1-oxa-3,8-diazaspiro[4.5]dec-8-yl)-8-azabicyclo[3.2.1]octane-8-carboxylate;
ethyl 3-(4-ethyl-2-oxo-1-oxa-3,8-diazaspiro[4.5]dec-8-yl)-8-azabicyclo[3.2.1]octane-8-carboxylate;
ethyl 3-[2-oxo-4-(propan-2-yl)-1-oxa-3,8-diazaspiro[4.5]dec-8-yl]-8-azabicyclo[3.2.1]octane-8-carboxylate;
ethyl 3-(4,4-dimethyl-2-oxo-1-oxa-3,8-diazaspiro[4.5]dec-8-yl)-8-azabicyclo[3.2.1]octane-8-carboxylate;
ethyl 2-fluoro-3-(2-oxo-1-oxa-3,8-diazaspiro[4.5]dec-8-yl)-8-azabicyclo[3.2.1]octane-8-carboxylate;
methyl 3-(2-oxo-1,3,8-triazaspiro[4.5]dec-8-yl)-8-azabicyclo[3.2.1]octane-8-carboxylate;
ethyl 3-(2-oxo-1,3,8-triazaspiro[4.5]dec-8-yl)-8-azabicyclo[3.2.1]octane-8-carboxylate;
ethyl 3-(1-benzyl-3-oxo-1,2,8-triazaspiro[4.5]dec-8-yl)-8-azabicyclo[3.2.1]octane-8-carboxylate;
Ethyl 3-(2-oxo-4-(pyridin-2-ylmethyl)-1-oxa-3,8-diazaspiro[4.5]decan-8-yl)-8-azabicyclo[3.2.1]octane-8-carboxylate;
propan-2-yl 3-(3-oxo-2,8-diazaspiro[4.5]dec-8-yl)-8-azabicyclo[3.2.1]octane-8-carboxylate;
ethyl 5-(2-oxo-1-oxa-3,8-diazaspiro[4.5]dec-8-yl)-2-azabicyclo[2.2.2]octane-2-carboxylate;
ethyl 5-(4-ethyl-2-oxo-1-oxa-3,8-diazaspiro[4.5]dec-8-yl)-2-azabicyclo[2.2.2]octane-2-carboxylate;
ethyl 5-[2-oxo-4-(2,2,2-trifluoroethyl)-1-oxa-3,8-diazaspiro[4.5]dec-8-yl]-2-azabicyclo[2.2.2]octane-2-carboxylate;
ethyl 5-(3-oxo-1-propyl-1,2,8-triazaspiro[4.5]dec-8-yl)-2-azabicyclo[2.2.2]octane-2-carboxylate;
ethyl 3-(2-oxo-1-oxa-3,8-diazaspiro[4.5]dec-8-yl)-9-azabicyclo[3.3.1]nonane-9-carboxylate;
ethyl 3-(2-oxo-1-oxa-3,8-diazaspiro[4.5]dec-8-yl)-6-azabicyclo[3.2.1]octane-6-carboxylate;
ethyl 3-(3-oxo-2,8-diazaspiro[4.6]undec-8-yl)-8-azabicyclo[3.2.1]octane-8-carboxylate;
ethyl 3-(2-oxo-1-oxa-3,8-diazaspiro[4.6]undec-8-yl)-8-azabicyclo[3.2.1]octane-8-carboxylate;
or a salt thereof.

3. The compound according to claim 1 which is ethyl 3-(3-oxo-2,8-diazaspiro[4.5]dec-8-yl)-8-azabicyclo[3.2.1]octane-8-carboxylate, or a salt thereof.

4. The compound according to claim 1 which is prop-2-yn-1-yl 3-(3-oxo-2,8-diazaspiro[4.5]dec-8-yl)-8-azabicyclo[3.2.1]octane-8-carboxylate, or a salt thereof.

5. The compound according to claim 1 which is ethyl (3-endo)-3-(2-hydroxy-3-oxo-2,8-diazaspiro[4.5]dec-8-yl)-8-azabicyclo[3.2.1]octane-8-carboxylate, or a salt thereof.

6. The compound according to claim 1 which is ethyl 5-(3-oxo-2,8-diazaspiro[4.5]dec-8-yl)-2-azabicyclo[2.2.2]octane-2-carboxylate, or a salt thereof.

7. The compound according to claim 1 which is ethyl 6-(2-oxo-1-oxa-3,8-diazaspiro[4.5]dec-8-yl)-3-azabicyclo[3.2.1]octane-3-carboxylate, or a salt thereof.

8. The compound according to claim 1 which is ethyl 3-(2-oxo-1-oxa-3,8-diazaspiro[4.5]dec-8-yl)-8-azabicyclo[3.2.1]octane-8-carboxylate, or a salt thereof.

9. A pharmaceutical composition comprising a compound as defined in claim 1 and a pharmaceutically acceptable excipient.

10. A method of treating dementia, comprising administering an effective amount of a compound according to claim 1 to a subject in need thereof.

11. The method according to claim 10, wherein the dementia is dementia with Lewy bodies.

12. The method according to claim 10, wherein the dementia is dementia associated with Alzheimer's disease.

13. The method according to claim 10, wherein the dementia is dementia associated with Schizophrenia.

* * * * *